(12) United States Patent
Lampe et al.

(10) Patent No.: US 7,320,974 B2
(45) Date of Patent: Jan. 22, 2008

(54) CYTOSKELETAL ACTIVE COMPOUNDS, COMPOSITIONS AND USE

(75) Inventors: John W. Lampe, Cary, NC (US); Robert Plourde, Jr., Chapel Hill, NC (US); Jin She, Chapel Hill, NC (US); Jason L. Vittitow, Durham, NC (US); Paul S. Watson, Carrboro, NC (US); Michael T. Crimmins, Chapel Hill, NC (US); David J. Slade, Durham, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 11/389,665

(22) Filed: Mar. 23, 2006

(65) Prior Publication Data

US 2006/0217427 A1 Sep. 28, 2006

Related U.S. Application Data

(60) Provisional application No. 60/665,408, filed on Mar. 25, 2005.

(51) Int. Cl.
*A61K 31/351* (2006.01)
*A61K 31/357* (2006.01)
*C07D 309/06* (2006.01)
*C07D 313/02* (2006.01)
*C07D 313/16* (2006.01)

(52) U.S. Cl. ............... 514/211.09; 514/450; 540/451; 540/456; 540/468; 548/182

(58) Field of Classification Search ............ 548/182; 540/451, 456, 468; 514/211.09, 450
See application file for complete search history.

(56) References Cited

U.S. PATENT DOCUMENTS

| | | | |
|---|---|---|---|
| 4,857,538 A | 8/1989 | Kashman et al. | |
| 5,798,380 A | 8/1998 | Kaufman et al. | 514/456 |
| 6,110,912 A | 8/2000 | Kaufman et al. | 514/218 |
| 6,586,425 B2 | 7/2003 | Kaufman et al. | 514/218 |
| 2002/0045585 A1 | 4/2002 | Kaufman et al. | |

FOREIGN PATENT DOCUMENTS

WO WO97/30701 8/1997

OTHER PUBLICATIONS

CA Registry No. 122877-01-4, entry date into Registry file on STN Sep. 29, 1989.*
CA Registry No. 122898-81-1, entry date into Registry file on STN Sep. 29, 1989.*
Blasberger, Dina et al, "On the chemistry of latrunculins A and B," Liebigs Annalen Der Chemie, 1989, (12), pp. 1171-1188.*
A. Fürstner et al., *Angew. Chem. Int. Ed.* 2003, 42, 5358-5360.
A. Fürstner et al., *Proc. Natl. Acad. Sci.* 2005, 102, 8103-8108.
A.B. Smith III et al., *J. Am. Chem. Soc.* 1992, 114, 2995-3007.
J.D. White and M. Kawasaki, *J. Org. Chem.* 1992, 57, 5292-5300.
Blasberger, Dina et al., "On the chemistry of latrunculins A and B", Liebigs Annalen Der Chemie, 1989, (12), 1171-88.
Fuerstner, Alois et al., "Concise and practical synthesis of latrunculin A by ring-closing enyne-yne metathesis", Angewandte Chemie, International Edition, 2005, 44 (22), 3462-3466.

* cited by examiner

*Primary Examiner*—Kamal A. Saeed
*Assistant Examiner*—Janet L Coppins
(74) *Attorney, Agent, or Firm*—Howrey LLP; Viola T. Kung

(57) ABSTRACT

The present invention is directed to synthetic cytoskeletal active compounds that are related to natural Latrunculin A or Latrunculin B. The present invention is also directed to pharmaceutical compositions comprising such compounds and a pharmaceutically acceptable carrier. The invention is additionally directed to a method of preventing or treating diseases or conditions associated with actin polymerization. In one embodiment of the invention, the method treats increased intraocular pressure, such as primary open-angle glaucoma. The method comprises administering to a subject a therapeutically effective amount of a cytoskeletal active compound of Formula I or II, wherein said amount is effective to influence the cytoskeleton, for example by inhibiting actin polymerization.

26 Claims, No Drawings

CYTOSKELETAL ACTIVE COMPOUNDS, COMPOSITIONS AND USE

This application claims priority to U.S. provisional application No. 60/665,408, filed Mar. 25, 2005. The content of which is incorporated herein by reference in its entirety.

TECHNICAL FIELD

This invention relates to synthetic cytoskeletal active compounds, such as latrunculin analog compounds, and the methods of making such compounds. The invention also relates to using such compounds in the prevention or treatment of diseases or disorders that are affected by the integrity of the actin cytoskeleton, for example, treatment of disorders in which intraocular pressure is elevated, such as primary open-angle glaucoma.

BACKGROUND OF THE INVENTION

Glaucoma is an ophthalmic disease that leads to irreversible visual impairment. It is the fourth most common cause of blindness and the second most common cause of visual loss in the United States, and the most common cause of irreversible visual loss among African-Americans. Generally speaking, the disease is characterized by a progressive neuropathy caused at least in part by deleterious effects resulting from increased intraocular pressure on the optic nerve. In normal individuals, intraocular pressures ranges from 12 to 20 mm Hg, averaging approximately 16 mm Hg. However, in individuals suffering from glaucoma, intraocular pressures generally rise above 25 to 30 mm Hg and can sometimes reach 70 mm Hg. Importantly, the loss of vision can result from intraocular pressures only slightly above or even within the statistically normal range, in eyes which are unusually pressure-sensitive, over a period of years. Moreover, extremely high pressures (e.g., 70 mm Hg) may cause blindness within only a few days. [See, e.g., P. L. Kaufman and T. W. Mittag, "Medical Therapy Of Glaucoma," Ch. 9, Sec. II (pp. 9.7-9.30) In P. L. Kaufman and T. W. Mittag (eds.): Glaucoma (Vol. 7 of S. M. Podos and M. Yanoff (eds): Textbook of Ophthalmology Series). London, Mosby-Year Book Europe Ltd. (1994); A. C. Guyton, Textbook of Medical Physiology (W. B. Saunders Co., Sixth Ed.), pp. 386-89 (1981)].

Open-angle glaucoma constitutes approximately 90% of all primary glaucomas and is characterized by abnormally high resistance to fluid (aqueous humor) drainage from the eye. Normal resistance is required to maintain an intraocular pressure sufficient to maintain the shape of the eye for optical integrity. This resistance is provided by the trabecular meshwork, a complex tissue consisting of specialized endothelial cells, connective tissue beams and extracellular matrix. The resistance of the trabecular meshwork normally is such that intraocular pressure is ~16 mm Hg, a pressure at which aqueous humor leaves the eye at the same rate at which it is produced (2.5 µL/minute).

Typical treatments for glaucoma comprise a variety of pharmaceutical approaches for reducing intraocular pressure (IOP) to normal levels. Beta-blockers and carbonic anhydrase inhibitors only reduce aqueous humor production, which is needed to nourish the avascular lens and corneal endothelial cells, and the prostaglandins effect is on the uvealscleral outflow pathway, which only accounts for 10% of the total facility. There are currently no commercially approved therapeutic agents which act directly upon the trabecular meshwork, the site of increased resistance to aqueous humor outflow and thus responsible for elevated IOP. Therefore, a medical need remains for improved IOP-lowering medications that target this structure. Pharmacological agents which target the trabecular meshwork may provide relief to the significant numbers of patients that do not respond adequately to current IOP-lowering medications and/or cannot tolerate the side effects associated with these agents.

U.S. Pat. Nos. 6,586,425; 6,110,912; and 5,798,380 disclose a method for the treatment of glaucoma using compounds that affect the actin filament integrity of the eye to enhance aqueous humor outflow. These patents also specifically disclose kinase inhibitors and latrunculin-A, latrunculin-B, swinholide-A, and jasplakinolide, which cause a perturbation of the actin cytoskeleton in the trabecular meshwork or the modulation of its interactions with the underlying membrane. Perturbation of the cytoskeleton and the associated adhesions reduces the resistance of the trabecular meshwork to fluid flow and thereby reduces intraocular pressure.

Trabeculectomy is the most common form of glaucoma filtration surgery and remains as the first-line therapy for surgical reduction of pharmacologically uncontrolled intraocular pressure in primary open angle glaucoma. This procedure establishes a limbal fistula through which aqueous humor drains into the subconjunctival space establishing a filtering bleb to lower intraocular pressure. The success of the procedure is highly dependent on pharmacological modulation of wound healing.

A major advance in the surgical management of glaucoma has been the use of antimetabolites to prevent scarring after glaucoma filtration surgery. Postoperative scarring of the filtering bleb is the most crucial factor in determining the short and long-term outcome of modem glaucoma filtration surgery. The antimetabolites mitomycin C (MMC) and 5-fluorouracil (5-FU) are the most widely used to suppress scarring and thus failure of the filtering bleb. In a large retrospective study, conventionally performed trabeculectomy, has shown a failure rate of up to 30% within 3 months after surgery. To lower the incidence of this detrimental complication, various methods have been investigated in order to avoid the naturally occurring scarring of the filtering bleb, mostly dealing with the intraoperative or postoperative application of antimetabolic drugs—that is, 5-fluorouracil (5-FU) or mitomycin C (MMC), the two most widely used cytotoxic agents.

Despite their positive long-term effect on prolonged filtration, the application of cytotoxic drugs to a surgically opened eye increases the incidence of severe complications such as concomitant increases in vision threatening complications. MMC exhibits a high incidence of severe post-application complications as does 5-FU although its side effects mainly affect the corneal epithelium and its clinical use is limited by severe pain and discomfort to the patient. No sufficient method has been established to achieve satisfying postoperative long term surgical results with only minimal or no side effects for the patient.

There exists a need for effective and cost-practical cytoskeletal active compounds to treat glaucoma, to modulate wound healing after trabeculectomy, and to treat other diseases or disorders that are affected by the integrity of the actin cytoskeleton. Natural latrunculins, cytoskeletal active macrolides harvested and isolated from marine sponges such as *Latrunculia magnifica, Negombata magnifica,* and *Spongia mycofijiensis,* and from nudibranches, for example *Chromodoris lochi,* are difficult to obtain a large quantity. Latrunculin analogs currently can only be prepared using lengthy, low-yielding, and impractical syntheses (A. B. Smith III et al., *J. Am. Chem. Soc.* 1992, 114, 2995-3007; J. D. White and M. Kawasaki, *J. Org. Chem.* 1992, 57, 5292-5300; A. Fürstner et al., *Angew. Chem. Int. Ed.* 2003, 42, 5358-5360; A. Fürstner et al., *Proc. Natl. Acad. Sci.* 2005, 102, 8103-8108). There exists a need for novel cytoskeletal active compounds that can be prepared using simple and practical synthetic procedures.

SUMMARY OF THE INVENTION

The present invention is directed to compounds of Formula I or Formula II, which are analogs related to the natural products latrunculin A or latrunculin B. The present invention is also directed to pharmaceutical compositions comprising such compounds and a pharmaceutically acceptable carrier.

The invention is additionally directed to a method of preventing or treating diseases or conditions associated with actin polymerization. In one embodiment of the invention, the method treats increased intraocular pressure, such as primary open-angle glaucoma.

The method comprises administering to a subject a therapeutically effective amount of a cytoskeletal active compound of Formula I or II, wherein said amount is effective to alter the actin cytoskeleton, such as by inhibiting actin polymerization.

DETAILED DESCRIPTION OF THE INVENTION

The inventors of the present invention have discovered compounds that are cytoskeletal active agents, which modify the actin cytoskeleton, for example by inhibiting actin polymerization. The compounds described herein bear a relationship to the natural products latrunculin A and B. These compounds contain structural simplifications that result in some aspects of their preparation being more practical, thus they are practical to be used as therapeutic agents. The structural modifications described herein provide new analogs with therapeutic utility.

DEFINITIONS

When present, unless otherwise specified, the following terms are generally defined as, but are not limited to, the following:

Halo substituents are taken from fluorine, chlorine, bromine, and iodine.

Alkyl groups are from 1 to 12 carbon atoms inclusively, either straight chained or branched, are more preferably from 1 to 8 carbon atoms inclusively, and most preferably 1 to 6 carbon atoms inclusively.

Alkylene chains are from 2 to 20 carbon atoms inclusively, have two points of attachment to the molecule to which they belong, are either straight chained or branched, can contain one or more double and/or triple bonds, are more preferably from 4 to 18 atoms inclusively, and are most preferably from 6 to 14 atoms inclusively.

Alkenyl groups are from 1 to 12 carbon atoms inclusively, either straight or branched containing at least one double bond but can contain more than one double bond.

Alkynyl groups are from 1 to 12 carbon atoms inclusively, either straight or branched containing at least one triple bond but can contain more than one triple bond, and additionally can contain one or more double bonded moieties.

"Alkoxy" refers to the group alkyl-O— wherein the alkyl group is as defined above including optionally substituted alkyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl-groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl-groups preferably having from 1 to 6 carbon atoms in the alkenyl moiety and from 6 to 10 carbon atoms inclusively in the aryl moiety.

"Arylalkynyl" refers to aryl-alkynyl-groups preferably having form 1 to 6 carbon atoms inclusively in the alkynyl moiety and from 6 to 10 carbon atoms inclusively in the aryl moiety.

"Aryloxy" refers to the group aryl-O— wherein the aryl group is as defined above including optionally substituted aryl groups as also defined above.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Cycloalkenyl" refers to cyclic alkenyl groups of from 4 to 12 carbon atoms inclusively having a single cyclic ring or multiple condensed rings and at least one point of internal unsaturation, which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Cycloalkylalkyl" refers to cycloalkyl-alkyl-groups preferably having from 1 to 6 carbon atoms inclusively in the alkyl moiety and from 6 to 10 carbon atoms inclusively in the cycloalkyl moiety. Such cycloalkylalkyl groups are exemplified by cyclopropylmethyl, cyclohexylethyl and the like.

"Heteroaryl" refers to a monovalent aromatic carbocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to heteroaryl-alkyl-groups preferably having form 1 to 6 carbon atoms inclusively in the alkyl moiety and from 6 to 10 carbon atoms inclusively in the heteroaryl moiety. Such arylalkyl groups are exemplified by pyridylmethyl and the like.

"Heteroarylalkenyl" refers to heteroaryl-alkenyl-groups preferably having from 1 to 6 carbon atoms inclusively in the alkenyl moiety and from 6 to 10 carbon atoms inclusively in the heteroaryl moiety.

"Heteroarylalkynyl" refers to heteroaryl-alkynyl-groups preferably having from 1 to 6 carbon atoms inclusively in the alkynyl moiety and from 6 to 10 carbon atoms inclusively in the heteroaryl moiety.

"Heterocycle" refers to a saturated or unsaturated group having a single ring or multiple condensed rings, form 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofliryl) or multiple condensed rings (e.g., indolinyl, dihydrobenzofuran or quinuclidinyl). Preferred heterocycles include piperidinyl, pyrrolidinyl and tetrahydrofuryl.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Positions occupied by hydrogen in the foregoing groups can be further substituted with substituents exemplified by, but not limited to, hydroxy, oxo, nitro, methoxy, ethoxy, alkoxy, substituted alkoxy, fluoro, chloro, bromo, iodo, methyl, ethyl, propyl, butyl, alkyl, substituted alkyl, thio, thioalkyl, acyl, carboxyl, alkoxycarbonyl, carboxamido, substituted carboxamido, alkylsulfonyl, alkylsulfinyl, alkylsulfonylamino, sulfonamido, substituted sulfonamide, cyano, amino, substituted amino, acylamino, trifluoromethyl, trifluoromethoxy, phenyl, aryl, substituted aryl, pyridyl, imidazolyl, heteroaryl, substituted heteroaryl, cyclopropyl, cyclobutyl, cyclopentyl, cyclohexyl, cycloalkyl, substituted cycloalkyl, pyrrolidinyl, piperidinyl, morpholino, and heterocycle; and preferred heteroatoms are oxygen, nitrogen, and sulfur. It is understood that where open valences exist on these substituents they can be further substituted with alkyl, cycloalkyl, aryl, heteroaryl, and/or heterocycle groups, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable.

Pharmaceutically acceptable salts are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, malic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$).

Tautomers are compounds that can exist in one or more forms, called tautomeric forms, which can interconvert by way of a migration of one or more hydrogen atoms in the compound accompanied by a rearrangement in the position of adjacent double bonds. These tautomeric forms are in equilibrium with each other, and the position of this equilibrium will depend on the exact nature of the physical state of the compound. It is understood that where tautomeric forms are possible, the current invention relates to all possible tautomeric forms.

Solvates are addition complexes in which a compound of Formula I or II is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toulene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definition of compounds in Formulae I and II encompasses all possible hydrates and solvates, in any proportion, which possess the stated activity.

Novel Compounds

The cytoskeletal active compounds useful for this invention include compounds of general Formulae I and II, and/or tautomers thereof, and/or pharmaceutically-acceptable salts, and/or solvates, and/or hydrates thereof.

A compound according to Formulae I and II can exist in several diastereomeric forms. The general structure of Formulae I and II includes all diastereomeric forms of such materials, when not specified otherwise. Formulae I and II also include mixtures of compounds of these Formulae, including mixtures of enantiomers, diastereomers and/or other isomers in any proportion.

A. Formula I

Compounds of Formula I are as follows:

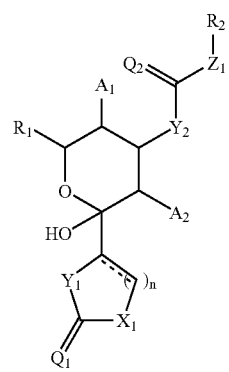

Formula I wherein:
$X_1$=S, O, $NR_3$, or $CR_4R_5$;
$Y_1$=S, O, or $NR_6$;
$Y_2$=S, O, or $NR_7$;
$Z_1$=S, O, $NR_8$, or absent;
$Q_1$ and $Q_2$ are independently O or S;
$A_1$ and $A_2$ are independently hydrogen, halo, alkyl, or alkoxy, optionally substituted;
n=1, 2, or 3;
$R_1$—$R_8$ are independently H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted;
the dashed line indicates that unsaturation is allowed in the ring containing it;
with the first proviso that when $Z_1$=S or O; $R_2$ is not H;

with the second proviso that when n is 1, $X_1$ is S, $Y_1$ is $NR_6$, $Y_2$ is O, $Z_1$ is absent, $Q_1$ and $Q_2$ are O, and if $R_2$ is selected from one of the following groups:

methyl,

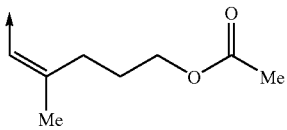

(Z)-5-acetoxy-2-methylpent-1-en-1-yl, or

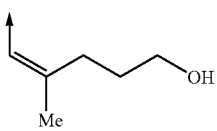

(Z)-5-hydroxy-2-methylpent-1-en-1-yl;

then $R_1$ is not 3-monomethyl-substituted alkyl, or $R_1$ is not selected from among the following groups:

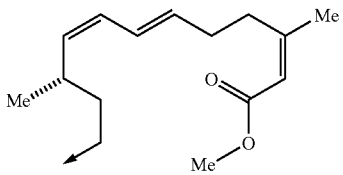

(S,4Z,6E,10Z)-11-methoxycarbonyl-3,10-dimethylundeca-4,6,10-trien-1-yl,

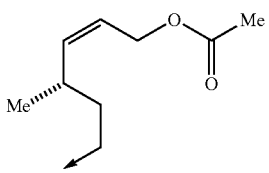

(S,Z)-6-acetoxy-3-methylhex-4-en-1-yl,

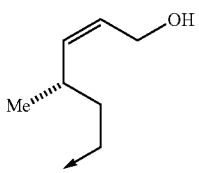

(S,Z)-6-hydroxy-3-methylhex-4-en-1-yl, or

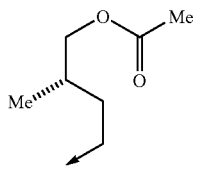

(S)-4-acetoxy-3-methylbutyl;

where in these structures, the bond marked with an arrow denotes the point of attachment of the group $R_1$ or $R_2$ to the rest of the molecule.

In one embodiment of Formula I, $A_1$ and $A_2$ are both hydrogen, and the ring containing $X_1$ is fully saturated, which is described by Formula Ia.

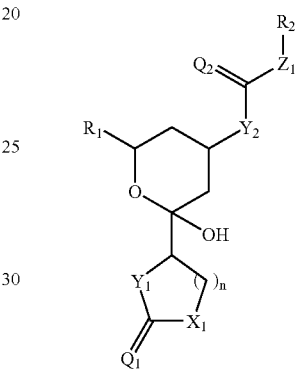

Formula Ia with the remaining Formula Ia substituents as defined above for Formula I.

In Formulae I and Ia, the preferred $X_1$ is S, O, or $NR_3$, the more preferred $X_1$ is S, the preferred $Y_1$ is $NR_6$, the more preferred $Y_1$ is NH, the preferred $Y_2$ is O or $NR_7$, the more preferred $Y_2$ is O, the preferred $Z_1$ is absent, the preferred $Q_1$ and $Q_2$ are O, the preferred n is 1 or 2, the more preferred n is 1, the preferred $R_1$ and $R_2$ are alkenyl, cycloalkenyl, aryl, arylalkyl, arylalkenyl, heteroaryl, heteroarylalkyl, and heteroarylalkenyl, in which both $R_1$ and $R_2$ are independently between 2 and 16 atoms, and both are optionally substituted, and the more preferred $R_1$ and $R_2$ are alkenyl, cycloalkenyl, aryl, arylalkenyl, heteroaryl, and heteroarylalkenyl, in which both $R_1$ and $R_2$ are independently between 4 and 12 atoms, and both are optionally substituted.

A preferred Formula I and Formula Ia compound is wherein:
$X_1$=S, O, or $NR_3$;
$Y_1$=$NR_6$;
$Y_2$=O or $NR_7$;
$Z_1$=absent;
$Q_1$ and $Q_2$ are O;
$A_1$ and $A_2$ are independently hydrogen, halo, alkyl, or alkoxy, optionally substituted;
n=1 or 2;
$R_1$ and $R_2$ are independently H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted; and
$R_3$—$R_8$ are independently H, alkyl, alkenyl, alkynyl, cycloalkyl, cycloalkenyl, or cycloalkylalkyl;
with the second proviso as stated above.

A more preferred Formula I and Formula Ia compound is wherein:

$X_1$=S;
$Y_1$=NH;
$Y_2$=O or $NR_7$;
$Z_1$=absent;
$Q_1$ and $Q_2$ are O;
$A_1$ and $A_2$ are independently hydrogen, halo, alkyl, or alkoxy, optionally substituted;
n=1;
$R_1$ and $R_2$ are independently H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted; and
$R_3$—$R_8$ are independently H, alkyl, alkenyl, alkynyl, cycloalkyl, cycloalkenyl, or cycloalkylalkyl;
with the second proviso as stated above.

In one embodiment of the invention, a Formula I and Formula Ia compound is wherein:

$X_1$=S, O, $NR_3$, or $CR_4R_5$;
$Y_1$=S, O, or $NR_6$;
$Y_2$=S, O, or $NR_7$;
$Z_1$=S, O, $NR_8$, or absent;
$Q_1$ and $Q_2$ are independently O or S;
$A_1$ and $A_2$ are independently hydrogen, halo, alkyl, or alkoxy, optionally substituted;
n=1, 2, or 3;
$R_1$-$R_8$ are independently H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted;
the dashed line indicates that unsaturation is allowed in the ring containing it;
with a first proviso that when $Z_1$=S or O, $R_2$ is not H;
with a second proviso that when n=1, $X_1$ is S, $Y_1$ is $NR_6$, $Y_2$ is O, $Z_1$ is absent, $Q_1$ is O, and $Q_2$ is O,
and in the case that $R_1$ is optionally substituted alkyl or alkenyl and begins with $CH_2CH_2$ from the point of attachment to the pyran ring, then $R_1$ is:

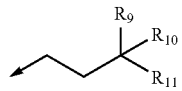

where the bond marked with an arrow denotes the point of attachment of the group $R_1$ to the rest of the molecule,
wherein $R_9$-$R_{10}$ are independently H, halo, alkyl, or alkenyl, optionally substituted, and $R_{11}$ is H, halo, alkyl, alkenyl, or —W—$R_{12}$, optionally substituted, where
W=O, S, SO, $SO_2$, NH, or N-alkyl, and
$R_{12}$ is H, alkyl, or alkenyl,
provided that if $R_9$ is H and $R_{10}$ is methyl, then $R_{11}$ is H, halo, or —W—$R_{12}$.

Specific Compounds illustrative of Formula I and Formula Ia are shown in the following Compounds 1-7. In the following structures, hydrogens are omitted from the drawings for the sake of simplicity. Tautomers drawn represent all tautomers possible. Structures are drawn to indicate the preferred stereochemistry; where diastereomers may be generated in these compounds, structures are taken to mean any of the possible diastereomers alone or a mixture of diastereomers in any ratio.

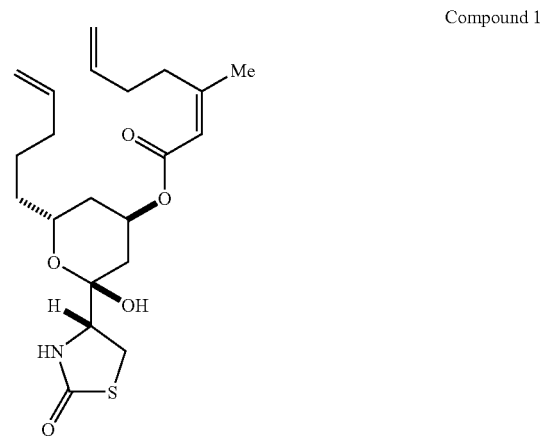

Compound 1

(Z)-((2R,4R,6R)-2-hydroxy-2-((R)-2-oxothiazolidin-4-yl)-6-(pent-4-enyl)-tetrahydro-2H-pyran-4-yl) 3-methylhepta-2,6-dienoate

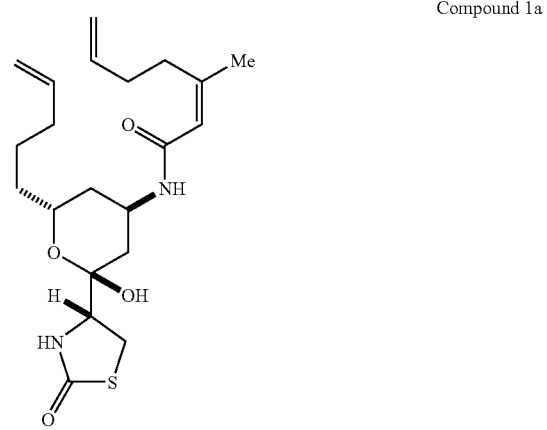

Compound 1a (Z)-N-((2R,4R,6R)-2-hydroxy-2-((R)-2-oxothiazolidin-4-yl)-6-(pent-4-enyl)-tetrahydro-2H-pyran-4-yl)-3-methylhepta-2,6-dienamide

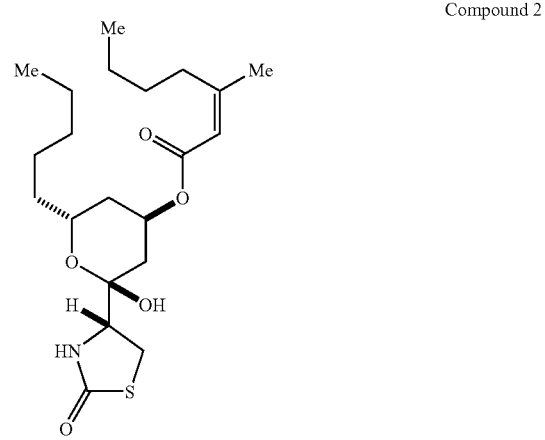

Compound 2

(Z)-((2R,4R,6R)-2-hydroxy-2-((R)-2-oxothiazolidin-4-yl)-6-pentyl-tetrahydro-2H-pyran-4-yl) 3-methylhept-2-enoate

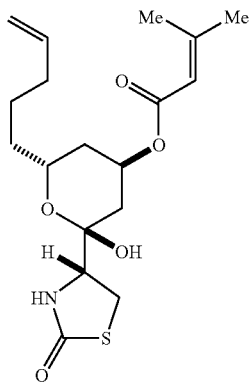

Compound 3

(2R,4R,6R)-2-hydroxy-2-((R)-2-oxothiazolidin-4-yl)-6-(pent-4-enyl)-tetrahydro-2H-pyran-4-yl 3-methylbut-2-enoate

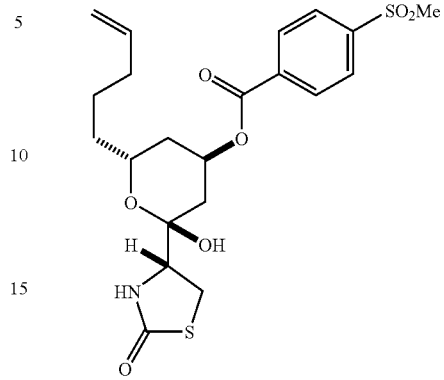

Compound 4b (2R,4R,6R)-2-hydroxy-2-((R)-2-oxothiazolidin-4-yl)-6-(pent-4-enyl)-tetrahydro-2H-pyran-4-yl 4-(methylsulfonyl)benzoate

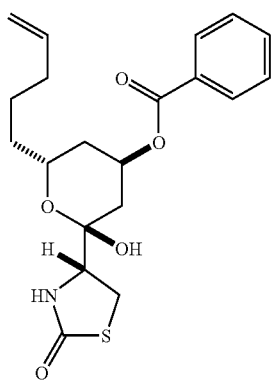

Compound 4

(2R,4R,6R)-2-hydroxy-2-((R)-2-oxothiazolidin-4-yl)-6-(pent-4-enyl)-tetrahydro-2H-pyran-4-yl benzoate

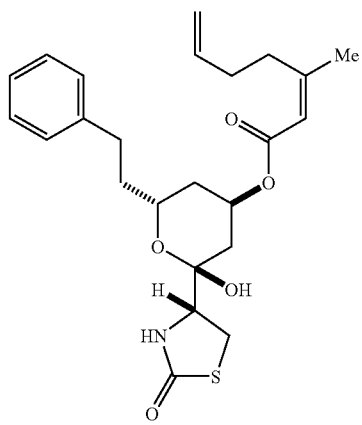

Compound 5

(Z-(2R,4R,6R)-2-hydroxy-2-((R)-2-oxothiazolidin-4-yl)-6-phenethyl-tetrahydro-2H-pyran-4-yl)-3-methylhepta-2,6-dienoate

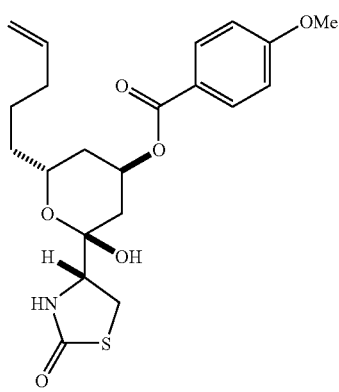

Compound 4a (2R,4R,6R)-2-hydroxy-2-((R)-2-oxothiazolidin-4-yl)-6-(pent-4-enyl)-tetrahydro-2H-pyran-4-yl 4-methoxybenzoate

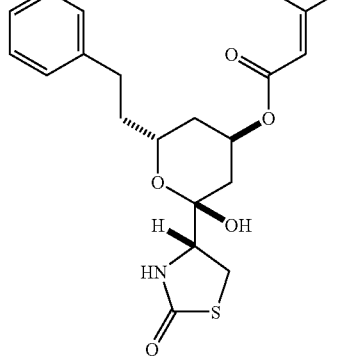

Compound 6

(2R,4R,6R)-2-hydroxy-2-((R)-2-oxothiazolidin-4-yl)-6-phenethyl-tetrahydro-2H-pyran-4-yl 3-methylbut-2-enoate

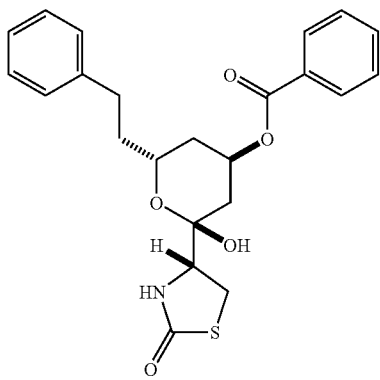

Compound 7

(2R,4R,6R)-2-hydroxy-2-((R)-2-oxothiazolidin-4-yl)-6-phenethyl-tetrahydro-2H-pyran-4-yl benzoate

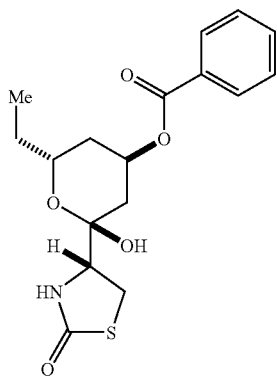

Compound 7a (2R,4R,6R)-6-ethyl-2-hydroxy-2-((R)-2-oxothiazolidin-4-yl)-tetrahydro-2H-pyran-4-yl benzoate B. Formula II
Compounds of Formula II are as follows:

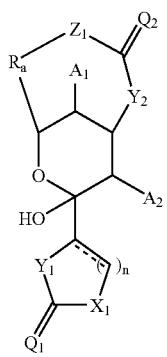

Formula II wherein:
$R_a$ is an alkylene chain, from 4 to 15 atoms in length, wherein the carbon atoms of the alkylene chain are optionally replaced by from 1 to 3 O, S, or N atoms, wherein the alkylene chain optionally contains from 1 to 4 unsaturations, 1 to 2 cycloalkyl, 1 to 2 aryl, 1 to 2 heteroaryl, or 1 to 2 heterocycle rings, and is optionally substituted;

$X_1$=S, O, $NR_3$, or $CR_4R_5$;
$Y_1$=S, O, or $NR_6$;
$Y_2$=S, O, or $NR_7$;
$Z_1$=S, O, $NR_8$; or absent;
$Q_1$ and $Q_2$ are independently O or S;
$A_1$ and $A_2$ are independently hydrogen, halo, alkyl, or alkoxy, optionally substituted;
n =1, 2, or 3;
$R_3$—$R_8$ are independently H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted;
the dashed line indicates that unsaturation is allowed in the ring containing it;
with the proviso that when n is 1, $X_1$ is S, $Y_1$ is $NR_6$, $Y_2$ is O, $Z_1$ is absent, and $Q_1$ and $Q_2$ are O, then either $R_a$ is not 3-monomethyl-susbtituted, as counted from the point of attachment distal to $Z_1$; or $R_a$ is not selected from the following groups:

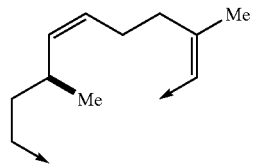

(S,1Z,5Z)-2,7-dimethylnona-1,5-diene-1,9-diyl

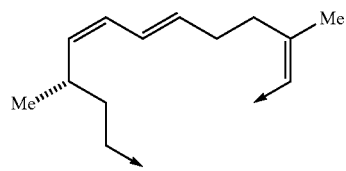

(S,1Z,5E,7Z)-2,9-dimethylundeca-1,5,7-triene-1,11-diyl

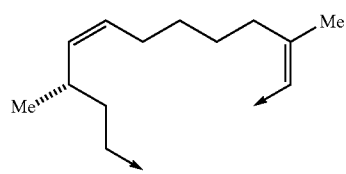

(S,1Z,7Z)-2,9-dimethylundeca-1,7-diene-1,11-diyl, or

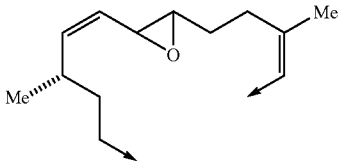

(S,1Z,7Z)-2,9-dimethyl-5,6-epoxyundeca-1,7-diene-
1,11-diyl where in these structures the right-most bond marked with an arrow indicates the point of attachment of $R_a$ to $Z_1$, and the left-most bond marked with an arrow indicates the point of attachment of $R_a$ to the pyran ring of Formula II.

In one embodiment of Formula II, $A_1$ and $A_2$ are both hydrogen, and the ring containing $X_1$ is fully saturated, which is described by Formula IIa.

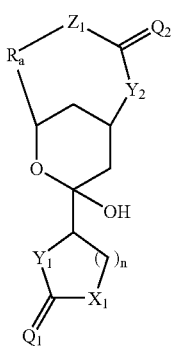

Formula IIa with the remaining Formula IIa substituents as defined above for Formula II.

In Formulae II and IIa, in the description of $R_a$, the terms "optionally containing cycloalkyl, aryl, heteroaryl, or heterocycle rings" indicate replacement of any carbon-carbon bond in $R_a$ with a cycloalkyl, aryl, heteroaryl, or heterocycle ring. Examples of such replacements include, but are not be limited to, the replacement of a carbon-carbon single, double, or triple bond with 1,2-cyclopentyl, 1,3-cyclopentyl, 1,2-cyclohexyl, 1,3-cyclohexyl, 1,4-cyclohexyl, 1,2-phenylene, 1,3-phenylene, 1,4-phenylene, 2,3-pyridyl, 2,4-pyridyl, 3,5-pyridyl, and 2,3-tetrahydrofuranyl.

In Formulae II and IIa, the preferred $X_1$ is S, O, or $NR_3$, the more preferred $X_1$ is S, the preferred $Y_1$ is $NR_6$, the more preferred $Y_1$ is NH, the preferred $Y_2$ is O or $NR_7$, the more preferred $Y_2$ is O, the preferred $Z_1$ is absent, the preferred $Q_1$ and $Q_2$ are O, the preferred n is 1 or 2, the more preferred n is 1, the preferred $R_a$ is an alkylene chain, from 6 to 13 atoms in length, wherein a carbon atom of the alkylene chain is optionally replaced by 1 O, S, or N atom, wherein the alkylene chain optionally contains from 1 to 3 unsaturations, and is optionally substituted, and the more preferred $R_a$ is an alkylene chain, from 8 to 11 atoms in length, wherein the alkylene chain optionally contains from 1 to 3 unsaturations, and is optionally substituted.

A preferred Formula II and Formula IIa compound is wherein:

$R_a$ is an alkylene chain, from 6 to 13 atoms in length, wherein a carbon atom of the alkylene chain is optionally replaced by 1 O, S, or N atom, wherein the alkylene chain optionally contains from 1 to 3 unsaturations, and is optionally substituted;
$X_1$=S, O, or $NR_3$;
$Y_1$=$NR_6$;
$Y_2$=O or $NR_7$;
$Z_1$=absent;
$Q_1$ and $Q_2$ are O;
$A_1$ and $A_2$ are independently hydrogen, halo, alkyl, or alkoxy, optionally substituted;
n=1 or 2; and
$R_3$-$R_8$ are independently H, alkyl, alkenyl, alkynyl, cycloalkyl, cycloalkenyl, or cycloalkylalkyl;
with the same proviso as stated above.

A more preferred Formula II and Formula IIa compound is:

$R_a$ is an alkylene chain, from 8 to 11 atoms in length, wherein the alkylene chain optionally contains from 1 to 3 unsaturations, and is optionally substituted;
$X_1$=S;
$Y_1$=NH;
$Y_2$=O or $NR_7$;
$Z_1$=absent;
$Q_1$ and $Q_2$ are O;
$A_1$ and $A_2$ are independently hydrogen, halo, alkyl, or alkoxy, optionally substituted;
n=1;
$R_3$-$R_8$ are independently H, alkyl, alkenyl, alkynyl, cycloalkyl, cycloalkenyl, or cycloalkylalkyl;
with the same proviso as stated above.

In one embodiment of the invention, a Formula II and Formula IIa compound is wherein:
$X_1$=S, O, $NR_3$, or $CR_4R_5$;
$Y_1$=S, O, or $NR_6$;
$Y_2$=S, O, or $NR_7$;
$Z_1$=absent;
$Q_1$ and $Q_2$ are independently O or S;
$A_1$ and $A_2$ are independently hydrogen, halo, alkyl, or alkoxy, optionally substituted;
n=1, 2, or 3;
$R_3$-$R_8$ are independently H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted;
$R_a$ is:

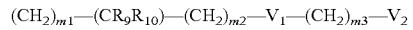
$(CH_2)_{m1}$—$(CR_9R_{10})$—$(CH_2)_{m2}$—$V_1$—$(CH_2)_{m3}$—$V_2$ wherein:
$m_1$, $m_2$, and $m_3$ are independently 0-5 inclusively, and $m_1+m_2+m_3$ is between 2 and 14 inclusively;
$R_9$ and $R_{10}$ are independently H, halo, alkyl, alkenyl, alkynyl, cycloalkyl, cycloalkenyl, cycloalkylalkyl, aryl, arylalkyl, arylalkenyl, heteroaryl, heteroarylalkyl, heteroarylalkenyl, heterocycle, or —W—$R_{12}$, optionally substituted;
W=O, S, SO, $SO_2$, NH, N-alkyl, N-cycloalkyl, N-aryl, or N-heteroaryl;
$R_{12}$ is H, alkyl, alkenyl, cycloalkyl, aryl, or heteroaryl;
$V_1$ is $NR_{13}$, O, S, SO, $SO_2$, cis —C($R_{13}$)=C($R_{14}$)—, trans —C($R_{13}$)=C($R_{14}$)—, —C-(triple bond)-C—, —OC(=O)—, —C(=O)O—, —N($R_{13}$)C(=O)—, —C(=O)N($R_{13}$)—, —N($R_{13}$)C(=O)O—, —OC(=O)N($R_{13}$)—, —N($R_{13}$)SO2—, —SO2N($R_{13}$)—, —N(R$_{13}$)C(=O)N(R$_{14}$)—, cycloalkyl, cycloalkenyl, aryl, heteroaryl, heterocycle, or absent;

V$_2$ is NR$_{13}$, O, cis —C(R$_{13}$)=C(R$_{14}$)—, trans —C(R$_{13}$)=C(R$_{14}$)—, —C-(triple bond)-C—, cycloalkyl, cycloalkenyl, aryl, heteroaryl, heterocycle, or absent;

R$_{13}$ and R$_{14}$ are independently H, alkyl, alkenyl, alkynyl, cycloalkyl, cycloalkenyl, cycloalkylalkyl, aryl, arylalkyl, arylalkenyl, heteroaryl, heteroarylalkyl, heteroarylalkenyl, or heterocycle, optionally substituted;

with the proviso that when m$_1$ is 2, m$_2$ is 0, m$_3$ is 2, V$_1$ is cis —CH=CH—, V$_2$ is —C(Me)=CH—, R$_9$ is H, and R$_{10}$ is alkyl, then R$_{10}$ has at least 2 carbon atoms (e.g. C$_2$-C$_{10}$ alkyl, preferably C$_2$-C$_6$ alkyl).

In the above embodiment, the preferred X$_1$ is S, O, or NR$_3$, the more preferred X$_1$ is S, the preferred Y$_1$ is NR$_6$, the more preferred Y$_1$ is NH, the preferred Y$_2$ is O or NR$_7$, the more preferred Y$_2$ is O, the preferred Q$_1$ and Q$_2$ are O, the preferred n is 1 or 2, the more preferred n is 1, the preferred R$_3$-R$_8$ are independently H, alkyl, alkenyl, alkynyl, cycloalkyl, cycloalkenyl, cycloalkylalkyl, aryl, arylalkyl, arylalkenyl, heteroaryl, heteroarylalkyl, heteroarylalkenyl, optionally substituted, the more preferred R$_3$-R$_8$ are H, alkyl, alkenyl, alkynyl, cycloalkyl, cycloalkenyl, or cycloalkylalkyl, optionally substituted;

the preferred m$_1$, m$_2$, and m$_3$ are 0-4 inclusively, the more preferred m$_1$, m$_2$, and m$_3$ are 0-3, inclusively;

the preferred R$_9$ and R$_{10}$ are independently H, halo, alkyl, alkenyl, cycloalkyl, cycloalkenyl, cycloalkylalkyl, aryl, arylalkyl, heteroaryl, heteroarylalkyl, or —W—R$_{12}$, optionally substituted, the more preferred R$_9$ and R$_{10}$ are H, halo, alkyl, alkenyl, cycloalkyl, cycloalkenyl, cycloalkylalkyl, aryl, or arylalkyl, optionally substituted;

the preferred W=O, S, NH, N-alkyl, N-cycloalkyl, N-aryl, or N-heteroaryl, the more preferred W=O, S, NH, N-alkyl, or N-cycloalkyl;

the preferred R$_{12}$ is H, alkyl, alkenyl, cycloalkyl, aryl, or heteroaryl, the more preferred R$_{12}$ is H, alkyl, cycloalkyl, or aryl;

the preferred V$_1$ is NR$_{13}$, O, S, cis —C(R$_{13}$)=C(R$_{14}$)—, trans —C(R$_{13}$)=C(R$_{14}$)—, N(R$_{13}$)C(=O)—, —C(=O)N(R$_{13}$)—, —N(R$_{13}$)C(=O)O—, —OC(=O)N(R$_{13}$)—, cycloalkyl, cycloalkenyl, aryl, heteroaryl, heterocycle, or absent, the more preferred V$_1$ is O, S, cis —C(R$_{13}$)=C(R$_{14}$)—, trans —C(R$_{13}$)=C(R$_{14}$)—, cycloalkyl, aryl, or absent;

the preferred V$_2$ is NR$_{13}$, cis —C(R$_{13}$)=C(R$_{14}$)—, trans —C(R$_{13}$)=C(R$_{14}$)—, cycloalky cycloalkenyl, aryl, heteroaryl, or absent, the more preferred V$_2$ is cis —C(R$_{13}$)=C(R$_{14}$)—, trans —C(R$_{13}$)=C(R$_{14}$)—, cycloalkenyl, or aryl;

the preferred R$_{13}$ and R$_{14}$ are H, alkyl, alkenyl, cycloalkyl, cycloalkenyl, cycloalkylalkyl, aryl, arylalkyl, arylalkenyl, heteroaryl, heteroarylalkyl, or heteroarylalkenyl, optionally substituted, the more preferred R$_{13}$ and R$_{14}$ are H, alkyl, cycloalkyl, cycloalkenyl, cycloalkylalkyl, aryl, arylalkyl, or heteroaryl, optionally substituted.

In one embodiment of the invention, a Formula II and Formula IIa compound is wherein:

R$_a$ is an alkylene chain, from 4 to 15 atoms in length, wherein the carbon atoms of the alkylene chain are optionally replaced by from 1 to 3 O, S, or N atoms, wherein the alkylene chain optionally contains from 1 to 4 unsaturations, 1 to 2 cycloalkyl, 1 to 2 aryl, 1 to 2 heteroaryl, or 1 to 2 heterocycle rings, and is optionally substituted;

X$_1$=S, O, NR$_3$, or CR$_4$R$_5$;

Y$_1$=S, O, or NR$_6$;

Y$_2$=S, O, or NR$_7$;

Z$_1$=S, O, NR$_8$, or absent;

Q$_1$ and Q$_2$ are independently O or S;

A$_1$ and A$_2$ are independently hydrogen, halo, alkyl, or alkoxy, optionally substituted;

n=1, 2, or 3;

R$_3$-R$_8$ are independently H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted;

the dashed line indicates that unsaturation is allowed in the ring containing it;

with the proviso that when n is 1, X$_1$ is S, Y$_1$ is NR$_6$, Y$_2$ is O, Z$_1$ is absent, Q$_1$ is O, Q$_2$ are O, and in the case that R$_a$ is 9 or 11 carbons in length, begins with CH$_2$CH$_2$ from the point of attachment to the pyran ring, and does not contain aryl or heteroaryl, then R$_a$ is:

then R$_a$ is:

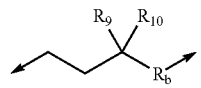

wherein R$_b$ is an alkylene chain, C$_6$-C$_8$ in length, optionally containing from 1 to 4 unsaturations, optionally containing a cycloalkyl ring and optionally substituted, and R$_9$ and R$_{10}$ are independently H, halo, alkyl, alkenyl, alkynyl, cycloalkyl, cycloalkenyl, cycloalkylalkyl, aryl, arylalkyl, arylalkenyl, heteroaryl, heteroarylalkyl, heteroarylalkenyl, heterocycle, or —W—R$_{12}$, optionally substituted, where W=O, S, SO, SO$_2$, NH, N-alkyl, N-cycloalkyl, N-aryl, or N-heteroaryl, and R$_{12}$ is H, alkyl, alkenyl, cycloalkyl, aryl, or heteroaryl, such that if R$_9$ is H, and R$_{10}$ is alkyl, then R$_{10}$ has at least 2 carbon atoms (e.g. C$_2$-C$_{10}$ alkyl, preferably C$_2$-C$_6$ alkyl);

where in this structure the right-most bond marked with an arrow indicates the point of attachment of R$_a$ to Z$_1$, and the left-most bond marked with an arrow indicates the point of attachment of R$_a$ to the pyran ring of FIG. II.

Specific compounds illustrative of Formula II are shown in the following Compounds 8-27. In the following structures, hydrogens have been omitted from the drawings for the sake of simplicity. Tautomers drawn represent all tautomers possible. Structures are drawn to indicate the preferred stereochemistry; where diastereomers may be generated in these compounds, structures are taken to mean any of the possible diastereomers alone or a mixture of diastereomers in any ratio.

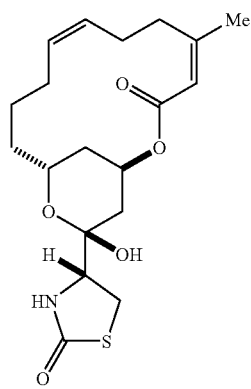

(R)-4-((1R,4Z,8Z,13R,15R)-15-hydroxy-5-methyl-3-oxo-2,14-dioxa-bicyclo[11.3.1]heptadeca-4,8-dien-15-yl)thiazolidin-2-one

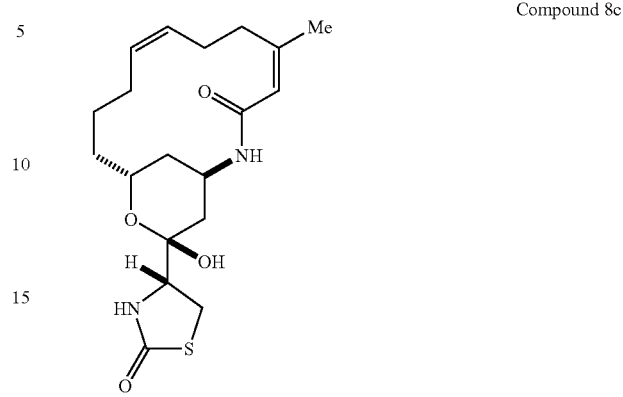

(1R,4Z,8Z,13R,15R)-15-hydroxy-5-methyl-15-((R)-2-oxothiazolidin-4-yl)-14-oxa-2-aza-bicyclo[11.3.1]heptadeca-4,8-dien-3-one Compound 8a (R)-4-((1R,4Z,8E,13R,15R)-15-hydroxy-5-methyl-3-oxo-2,14-dioxa-bicyclo[11.3.1]heptadeca-4,8-dien-15-yl)thiazolidin-2-one

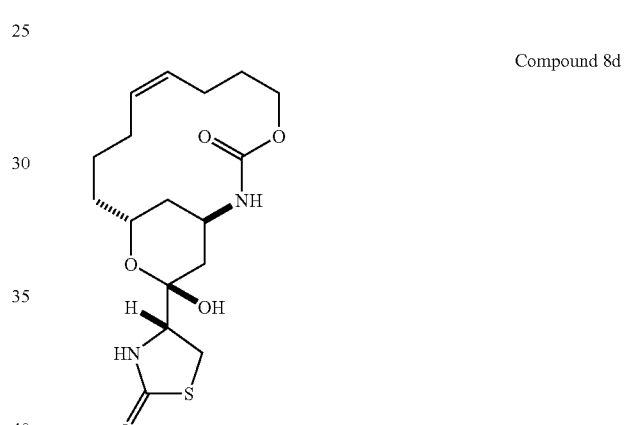

(1R,13R,15R,Z)-15-hydroxy-15-((R)-2-oxothiazolidin-4-yl)-4,14-dioxa-2-aza-bicyclo[11.3.1]heptadec-8-en-3-one Compound 8b

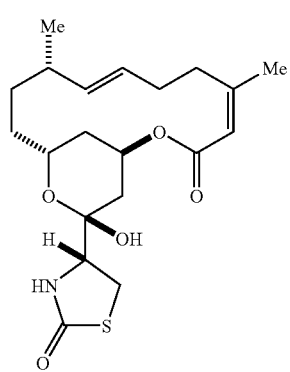

(R)-4-((1R,4Z,8E,10S,13R,15R)-15-hydroxy-5,10-dimethyl-3-oxo-2,14-dioxa-bicyclo[11.3.1]heptadeca-4,8-dien-15-yl)thiazolidin-2-one

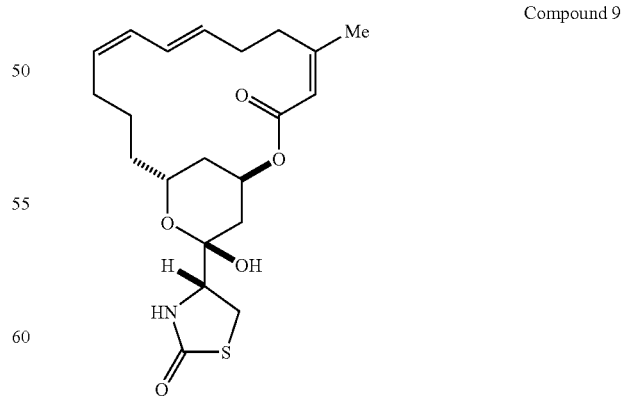

(R)-4-((1R,4Z,8E,10Z,15R,17R)-17-hydroxy-5-methyl-3-oxo-2,16-dioxa-bicyclo[13.3.1]nonadeca-4,8,10-trien-17-yl)thiazolidin-2-one

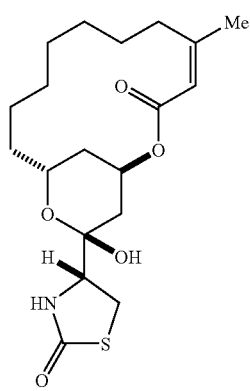

Compound 10

(R)-4-((1R,13R,15R,Z)-15-hydroxy-5-methyl-3-oxo-2,14-dioxa-bicyclo[11.3.1]heptadec-4-en-15-yl)thiazolidin-2-one

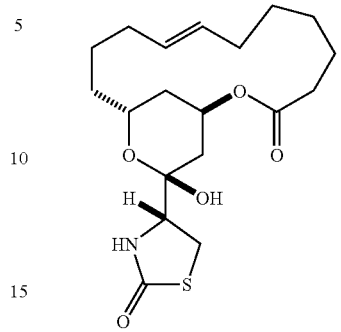

Compound 10c (R)-4-((1R,14R,16R,E)-16-hydroxy-3-oxo-2,15-dioxa-bicyclo[12.3.1]octadec-9-en-16-yl)thiazolidin-2-one Compound 10a (R)-4-((1R,13R,15R,Z)-15-hydroxy-3-oxo-2,14-dioxa-bicyclo[11.3.1]heptadec-8-en-15-yl)thiazolidin-2-one

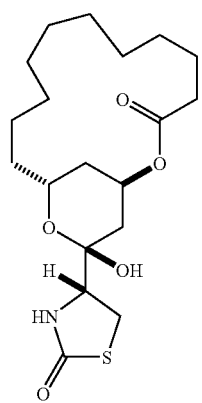

Compound 10d (R)-4-((1R,14R,16R)-16-hydroxy-3-oxo-2,15-dioxa-bicyclo[12.3.1]octadecan-16-yl)thiazolidin-2-one Compound 10b (R)-4-((1R,13R,15R)-15-hydroxy-3-oxo-2,14-dioxa-bicyclo[11.3.1]heptadecan-15-yl)thiazolidin-2-one

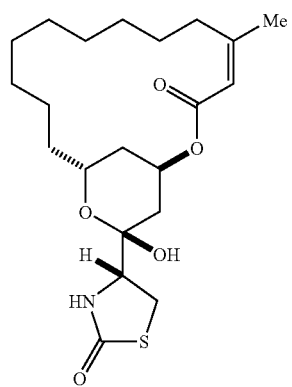

Compound 11

(R)-4-((1R,15R,17R,Z)-17-hydroxy-5-methyl-3-oxo-2,16-dioxa-bicyclo[13.3.1]nonadec-4-en-17-yl)thiazolidin-2-one

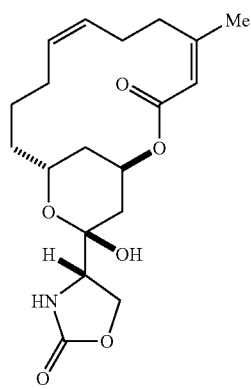

(S)-4-((1R,4Z,8Z,13R,15R)-15-hydroxy-5-methyl-3-oxo-2,14-dioxa-bicyclo[11.3.1]heptadeca-4,8-dien-15-yl)oxazolidin-2-one

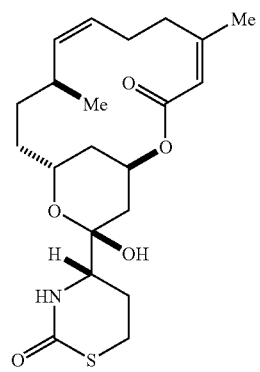

(S)-4-((1R,4Z,8Z,10S,13R,15R)-15-hydroxy-5,10-dimethyl-3-oxo-2,14-dioxa-bicyclo[11.3.1]heptadeca-4,8-dien-15-yl)-1,3-thiazinan-2-one

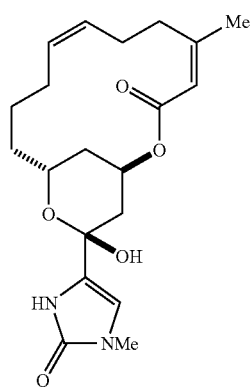

4-((1R,4Z,8Z,13R,15R)-15-hydroxy-5-methyl-3-oxo-2,14-dioxa-bicyclo[11.3.1]heptadeca-4,8-dien-15-yl)-1-methyl-1H-imidazol-2(3H)-one

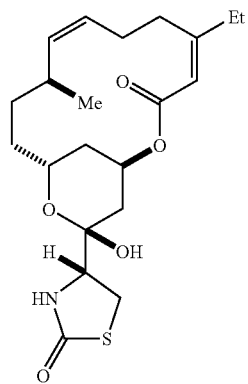

(R)-4-((1R,4Z,8Z,10S,13R,15R)-5-ethyl-15-hydroxy-10-methyl-3-oxo-2,14-dioxa-bicyclo[11.3.1]heptadeca-4,8-dien-15-yl)thiazolidin-2-one

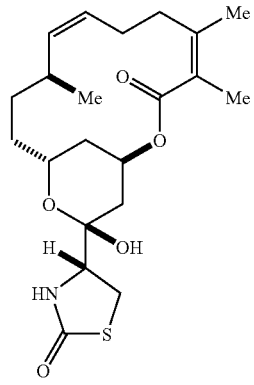

(R)-4-((1R,4Z,8Z,10S,13R,15R)-15-hydroxy-4,5,10-trimethyl-3-oxo-2,14-dioxa-bicyclo[11.3.1]heptadeca-4,8-dien-15-yl)thiazolidin-2-one

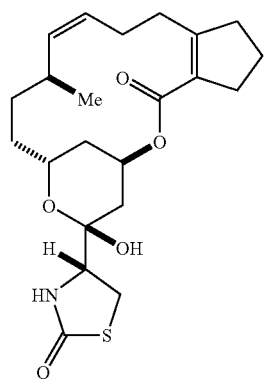

(R)-4-((1R,11Z,13S,16R,18R)-18-hydroxy-13-methyl-3-oxo-2,17-dioxatricyclo[14.3.1.0$^{4,8}$]icosa-4(8),11-dien-18-yl)thiazolidin-2-one

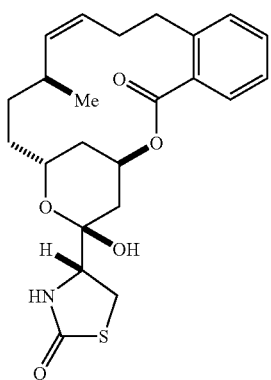

(R)-4-((1R,12Z,14S,17R,19R)-19-hydroxy-14-methyl-3-oxo-2,18-dioxatricyclo[15.3.1.0$^{4,9}$]henicosa-4,6,8,12-tetraen-19-yl)thiazolidin-2-one

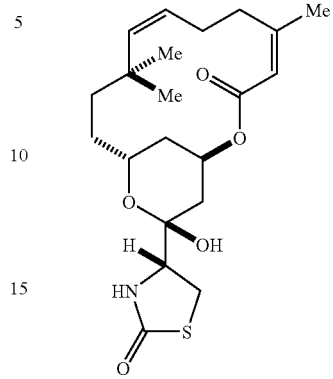

Compound 21

(R)-4-((1R,4Z,8Z,13R,15R)-15-hydroxy-5,10,10-trimethyl-3-oxo-2,14-dioxa-bicyclo[11.3.1]heptadeca-4,8-dien-15-yl)thiazolidin-2-one Compound 19

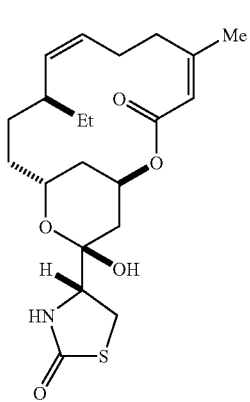

(R)-4-((1R,10Z,15R,17R)-17-hydroxy-3-oxo-2,16-dioxatricyclo[13.3.1.1$^{4,8}$]icosa-4(20),5,7,10-tetraen-17-yl)thiazolidin-2-one

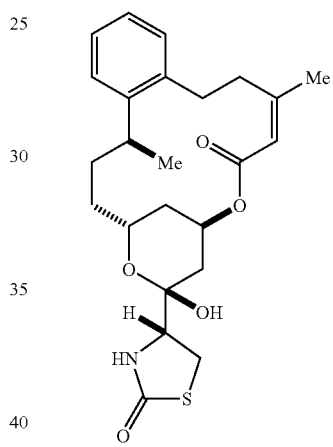

Compound 22

(R)-4-((1R,4S,13Z,17R,19R)-19-hydroxy-4,13-dimethyl-15-oxo-16,20-dioxatricyclo[15.3.1.0$^{5,10}$]henicosa-5,7,9,13-tetraen-19-yl)thiazolidin-2-one Compound 20

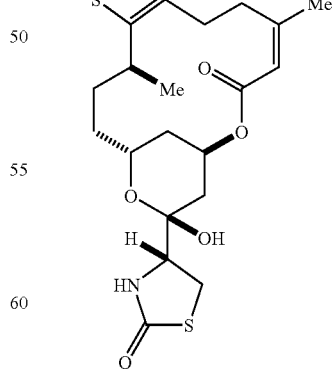

(R)-4-((1R,4Z,8Z,10S,13R,15R)-10-ethyl-15-hydroxy-5-methyl-3-oxo-2,14-dioxa-bicyclo[11.3.1]heptadeca-4,8-dien-15-yl)thiazolidin-2-one Compound 23

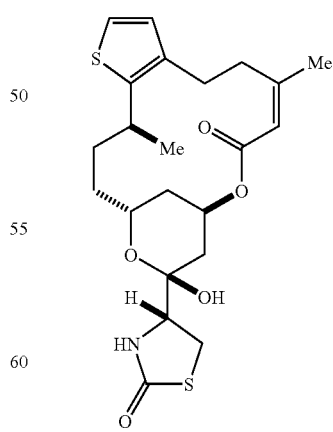

(R)-4-((1R,4S,12Z,16R,18R)-18-hydroxy-4,12-dimethyl-14-oxo-15,19-dioxa-6-thiatricyclo[14.3.1.0$^{5,9}$]icosa-5(9),7,12-trien-18-yl)thiazolidin-2-one Compound 24

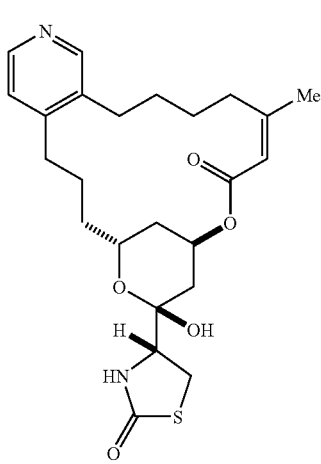

(R)-4-((1R,15E,19R,21R)-21-hydroxy-15-methyl-17-oxo-18,22-dioxa-8-azatricyclo[17.3.1.0^{5,10}]tricosa-5,7,9,15-tetraen-21-yl)thiazolidin-2-one Compound 25

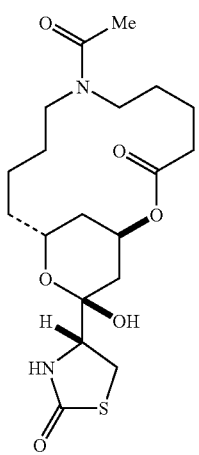

(1R,13R,15R)-8-acetyl-15-hydroxy-15-((R)-2-oxothiazolidin-4-yl)-2,14-dioxa-8-aza-bicyclo[11.3.1]heptadecan-3-one Compound 26

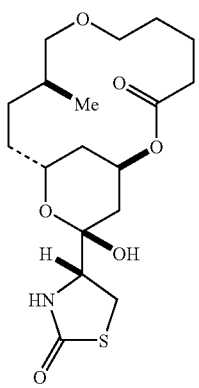

(R)-4-((1R,10S,13R,15R)-15-hydroxy-10-methyl-3-oxo-2,8,14-trioxa-bicyclo[11.3.1]heptadecan-15-yl)thiazolidin-2-one Compound 27

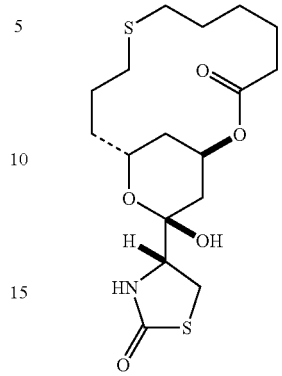

(R)-4-((1R,13R,15R)-15-hydroxy-3-oxo-2,14-dioxa-9-thia-bicyclo[11.3.1]heptadecan-15-yl)thiazolidin-2-one Preparation of Compounds of Formula I and Formula II The present invention is additionally directed to procedures for preparing compounds of Formulae I and II. General approaches for preparations of the compounds of Formulae I and II are described in Schemes 1 and 2. Those having skill in the art will recognize that the starting materials can be varied and additional steps can be employed to produce compounds encompassed by the present invention. In some cases, protection of certain reactive functionalities may be necessary to achieve some of the above transformations. In general, the need for such protecting groups as well as the conditions necessary to attach and remove such groups will be apparent to those skilled in the art of organic synthesis.

Those skilled in the art will recognize various synthetic methodologies that can be employed to prepare non-toxic pharmaceutically acceptable prodrugs, for example acylated prodrugs, of the compounds of this invention.

Scheme 1

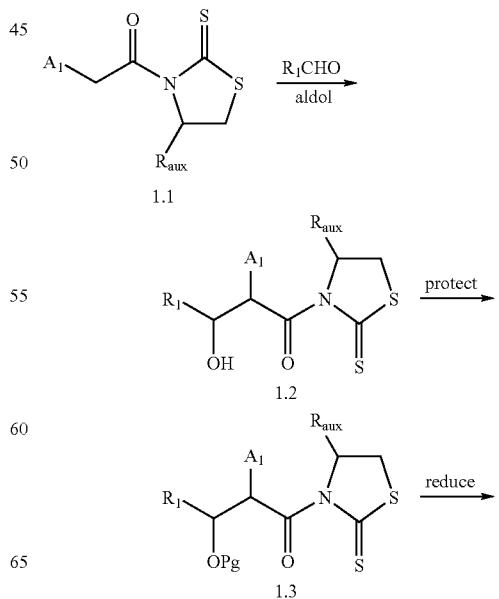

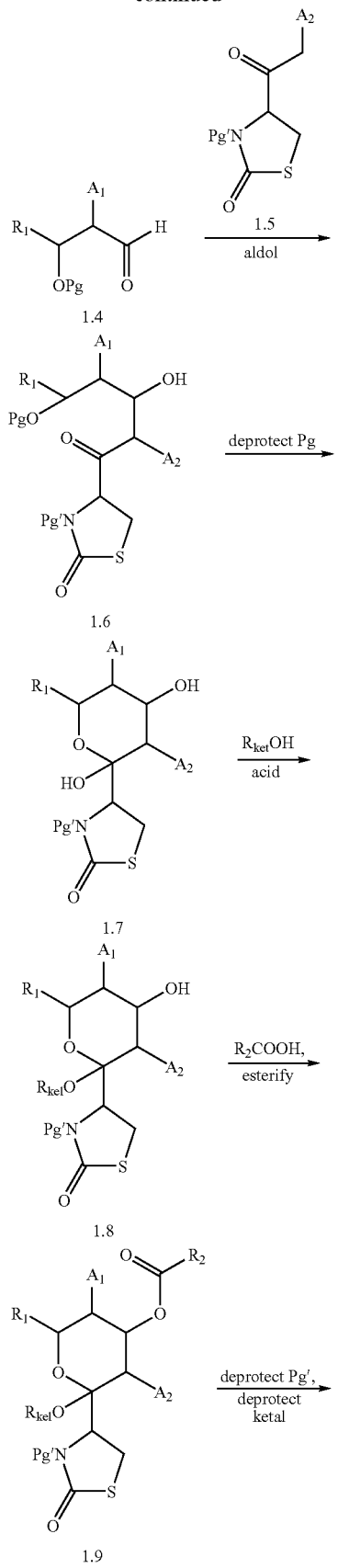
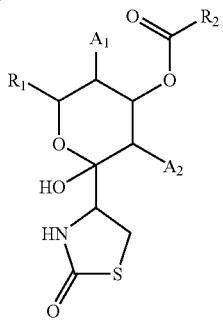

The preparation of materials described by Formula I is shown in Scheme 1. In this scheme, an acyl compound bearing a chiral auxiliary (1.1) is reacted in an aldol condensation with an aldehyde to yield an aldol product (1.2). This aldol condensation may be carried out using titanium enolate conditions; alternatively, other aldol conditions such as lithium or boron enolate or Mukaiyama aldol conditions may be used. This aldol reaction provides stereoisomers, which may be separated at this point. The aldol product is protected, typically with an acid-labile protecting group such as a silyl protecting group, to yield the protected aldol (1.3). Reduction of this protected compound, typically with diisobutylaluminum hydride (DIBAL-H), provides the aldehyde (1.4). Protected heterocyclic ketones 1.5 are prepared using methods analogous to those reported by Smith et al. (A. B. Smith III et al., *J. Am. Chem. Soc.* 1992, 114, 2995-3007), or more preferably using a method in which the protecting group "Pg" is introduced in a two step condensation-reduction sequence, followed by cyclization to form the heterocyclic ring and elaboration of the ketone moiety, as described below in Examples 1 through 5. Aldol reaction of aldehyde 1.4 with the heterocyclic ketone 1.5, under aldol conditions such as titanium, lithium, or boron enolate conditions or Mukaiyama aldol conditions, gives the aldol product (1.6). This aldol may yield diastereomeric products, which may be separated at this point in the synthesis or at later points. Removal of the protecting group "Pg" typically by treatment with mild acid, provides the deprotected material (1.7), as the hemiketal. Under some conditions, the protecting group is removed directly in the aldol reaction during the reaction itself or during its workup. This material is protected as the ketal (1.8), typically the methyl ketal, by treatment with an alcohol and acid, typically a sulfonic acid, optionally in the presence of a cosolvent. The compounds 1.7 and 1.8 provide convenient points for the separation of stereoisomers in some cases. The alcohol 1.8 is converted to the ester (1.9) either by direct acylation, such as with a carboxylic acid and a suitable activating agent such as a carbodiimide or carbonyldiimidazole, or by acylation with an acid halide, or by an inversion process such as by a Mitsunobu reaction or by preparation of an active leaving group such as a sulfonate ester and displacement with a suitably activated form of a carboxylic acid nucleophile. Final deprotection of the ester 1.9 provides compound 1.10, an example of the substances described by Formula I. It will be seen that modifications of this synthetic scheme using well-known procedures will allow the preparation of other members in the scope of Formula I.

Scheme 2

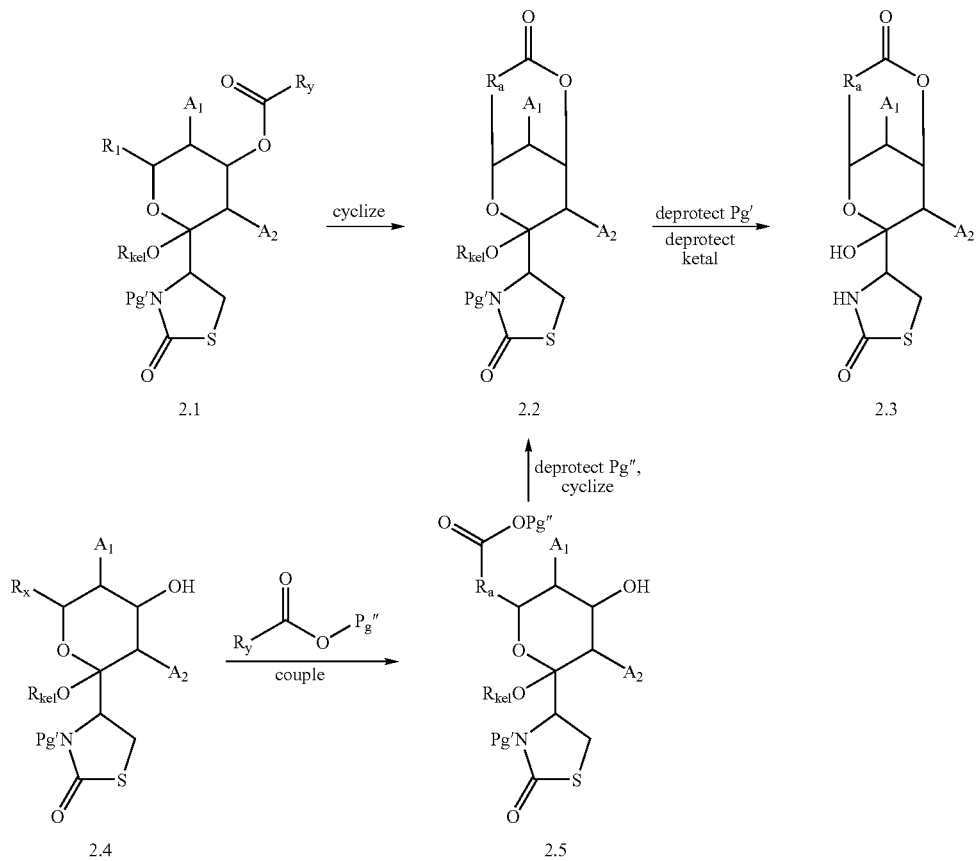

The preparation of materials described by Formula II is shown in Scheme 2. In this Scheme, a compound of general form 2.1 is prepared using the methods described in Scheme 1. In this compound, the substituents "$R_x$" and "$R_y$" are substituents that bear functionality that will allow a macrocyclization reaction to take place, yielding a macrocycle (2.2) with a newly formed substituent "$R_a$" incorporated in the new ring. Suitable macrocyclization reactions in this case include, for example, ring forming metathesis reactions, olefination, lactonization, lactamization, etherification, and amination reactions. Deprotection of the macrocyclic compound gives compound 2.3, an example of the substances described by Formula II. In an alternative method, a compound of general form 2.4, also prepared using the methods described in Scheme 1, is elaborated using one of the same reactions listed above for macrocyclization to yield a non-macrocyclic precursor (2.5). The protecting group "Pg'''" is then removed from 2.5 and the resulting product is cyclized, for example using a macrolactonization reaction, to provide compound 2.2, which is deprotected as was previously described. It will be seen that modifications of this synthetic scheme using other suitable procedures will allow the preparation of other members in the scope of Formula II.

Pharmaceutical Composition and Use

The present invention also provides novel pharmaceutical compositions. The pharmaceutical compositions are pharmaceutically acceptable formulations comprising a pharmaceutically acceptable carrier and one or more compounds of Formulae I and II, pharmaceutically-acceptable salts, solvates, and/or hydrates thereof. The pharmaceutically acceptable carrier can be selected by those skilled in the art using conventional criteria. Pharmaceutically acceptable carriers include, but are not limited to, saline and aqueous electrolyte solutions, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In one embodiment of the invention, the compositions are formulated as topical ophthalmic suspensions or solutions, with a pH of about 4-9, preferably 5 to 8. The compounds of the invention are generally contained in these formulations in an amount of at least 0.001 or 0.005% by weight, for example, 0.001% to 5% by weight, preferably about 0.01% to about 2% by weight, with an amount of about 0.03% to about 1% by weight being most preferred. For topical administration, one to two drops of these formulations are delivered to the surface of the eye one to four times per day according to the routine discretion of a skilled clinician.

In one embodiment of the invention, the compositions are formulated as aqueous pharmaceutical formulations comprising at least one compound of Formula I or II in an amount of 0.001-2% w/v, and a tonicity agent to maintain a tonicity between 200-400 mOsm/kG, wherein the pH of the formulation is 4-8, and the formulation does not contain a substantial amount of dimethyl sulfoxide. As used herein, "a substantial amount" refers to more than 0.1%, preferably 0.01%, and more preferably 0.001%. The aqueous pharmaceutical formulation of the present invention does not contain more than 0.1%, preferably not more than 0.01%, and more preferably not more than 0.001% v/v of DMSO. In a preferred embodiment, the aqueous pharmaceutical formulation of the present invention does not contain any dimethyl sulfoxide.

In one embodiment, the aqueous pharmaceutical formulation comprises at least one compound of Formula I or II in an amount of 0.001-2% w/v, 1-100 mM buffer suitable to maintain the pH between 4-6, 0.01-2% surfactant, and a tonicity agent to maintain a tonicity between 200-400 mOsm/kG. A preferred buffer is citrate buffer. Preferred tonicity agents are mannitol and dextrose.

In another embodiment, the aqueous pharmaceutical formulation comprises at least one compound of Formula I or II in an amount of 0.001-2% w/v, 5-10% ethanol and a tonicity agent to maintain a tonicity between 200-400 mOsm/kG. The formulation optionally comprises 1-100 mM buffer to maintain the pH between 4-8.

In yet another embodiment, the aqueous pharmaceutical formulation comprises at least one compound of Formula I or II in an amount of 0.001-2% w/v, 1-10% polypropylene glycol, 0.02-0.25% polaxamer, 0.1-1% polysorbate, and a tonicity agent to maintain a tonicity between 200-400 mOsm/kG, wherein the pH of the formulation is 4-8.

In yet another embodiment, the aqueous pharmaceutical formulation comprises at least one compound of Formula I or II in an amount of 0.001-2% w/v, a cyclodextrin, 0.01-0.5% preservative, and a tonicity agent to maintain a tonicity between 200-400 mOsm/kG, wherein the pH of the formulation is 4-8.

Glaucoma is an ophthalmic disease that leads to irreversible visual impairment. Open-angle glaucoma is characterized by abnormally high resistance to fluid (aqueous humor) drainage from the eye. Adhesions between cells of the trabecular meshwork are major determinants of the resistance to flow. The compounds of the present invention in general cause a transient, pharmacological perturbation of cell adhesions, mainly via disruption of the associated cytoskeletal structures or the modulation of their interactions with the membrane. Perturbation of these adhesions reduces the resistance of the trabecular meshwork to fluid flow and thereby reduces intraocular pressure in a therapeutically useful manner.

The compounds of the present invention are useful for modulation of wound healing after trabeculectomy. The compounds in general are less toxic to corneal endothelial cells than the antimetabolites such as 5-fluorouracil or mitomycin C. The compounds inhibit actomyosin-driven contractility, leading to deterioration of the actin microfilament system and perturbation of its membrane anchorage, which weakens the cell-extracellular matrix adhesions. These properties inhibit wound healing and thereby reduce bleb failure following the surgery.

Angiogenesis is characterized by the development of new vasculature from pre-existing vessels and plays a central role in physiological processes such as embryogenesis, wound healing and female reproductive function, as well as pathophysiologic events including cancer, rheumatoid arthritis and diabetic retinopathy. The growth and metastasis of tumors is critically dependent upon angiogenesis. Angiogenesis is a multistep process involving the endothelial cell (EC) cytoskeleton in migration, proliferation, and barrier stabilization. Applicants believe that interactions between the cytoskeleton and apoptosis are involved in the intracellular pathways by which angiogenic tube formation occurs. The compounds of the present invention are useful in inhibiting angiogenesis and treating tumors.

Antimitotic drugs markedly interfere with antidiuretic response, strongly implying that cytoskeleton integrity is essential to this function. This role of the cytoskeleton in controlling the epithelial transport is a necessary step in the translocation of the water channel containing particle aggregates and in their delivery to the apical membrane. Regulation of the actin cytoskeleton is important in the modulation of fluid transport. Osmolality-dependent reorganization of the cytoskeleton and expression of specific stress proteins are important components of the regulatory systems involved in the adaptation of medullary cells to osmotic stress. The compounds of the present invention are useful in directing epithelial function and modulating fluid transport.

The present invention provides a method of reducing intraocular pressure, a method of treating glaucoma, a method of inhibiting wound healing after trabeculectomy, a method of inhibiting angiogenesis, a method of treating cancer, and a method of directing epithelial function and modulating fluid transport. The method comprises the step of administering to a subject in need of treatment a pharmaceutical composition comprising a compound of Formula I or Formula II, in an amount effective to alter the actin cytoskeleton, such as by inhibiting actin polymerization.

In one embodiment, the pharmaceutical composition of the present invention is administered locally to the eye (e.g., topically, intracamerally, or via an implant) in the form of ophthalmic formulations. The compounds of the invention can be combined with ophthalmologically acceptable preservatives, surfactants, viscosity enhancers, penetration enhancers, buffers, sodium chloride, and water to form an aqueous or oily, sterile ophthalmic suspension or solution to form the compositions of the invention.

The active compounds disclosed herein can be administered to the eyes of a patient by any suitable means, but are preferably administered by administering a liquid or gel suspension of the active compound in the form of drops, spray or gel. Alternatively, the active compounds can be applied to the eye via liposomes. Further, the active compounds can be infused into the tear film via a pump-catheter system. Another embodiment of the present invention involves the active compound contained within a continuous or selective-release device, for example, membranes such as, but not limited to, those employed in the Ocusert™ System (Alza Corp., Palo Alto, Calif.). As an additional embodiment, the active compounds can be contained within, carried by, or attached to contact lenses that are placed on the eye. Another embodiment of the present invention involves the active compound contained within a swab or sponge that can be applied to the ocular surface. Another embodiment of the present invention involves the active compound contained within a liquid spray that can be applied to the ocular surface. Another embodiment of the present invention involves an injection of the active compound directly into the lacrimal tissues or onto the eye surface.

In addition to the topical administration of the compounds to the eye, when the present compounds are used in a method of inhibiting angiogenesis, a method of treating cancer, or a method of directing epithelial function and modulating fluid transport, the compounds can be administered systematically by any methods known to a skilled person.

The compounds of the present invention can also be used to treat asthma, COPD, emphysema, bladder dysfunction, and high blood pressure by means and route of administration known to those skilled in the art. Further uses of the present compounds can be in the area of cosmetics for reducing wrinkles, in the area of preserving blood platelets, and in the area of vasospasm and smooth muscle spasm by means and route of administration known to those skilled in the art.

The invention is illustrated further by the following examples that are not to be construed as limiting the invention in scope to the specific procedures described in them.

EXAMPLES

Example 1

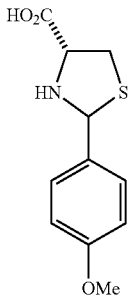

(4R)-2-(4-Methoxyphenyl)thiazolidine-4-carboxylic Acid

A 22 L three-necked round bottom flask fitted with an internal temperature probe and a mechanical stirrer was charged with L-cysteine hydrochloride monohydrate (500.0 g, 2.85 mol), sodium acetate (260.0 g, 3.17 mol) and water (4 L). The mixture was stirred until all of the L-cysteine dissolved. A solution of 4-methoxybenzaldehyde (426.0 g, 3.13 mol) in ethanol (3.5 L) was prepared and added to the reaction dropwise such that the internal reaction temperature was kept below 30° C. The reaction went from a clear solution to a thick white slurry during the addition of the 4-methoxybenzaldehyde solution. After 30 minutes, ethanol (3.5 L) was added to the reaction and the slurry thickened. Stirring was continued for 1 hour and then the solid was isolated by filtration, and the solid was washed with additional ethanol. The solid was dried in a vacuum oven at 50° C. over 48 hours to afford the title compound (610 g, 90%).

1H NMR (DMSO, 300 MHz): δ3.16-3.00 (m, 2H), 3.37-3.23 (m, 2H), 3.71 (s, 3H), 3.73 (s, 3H), 3.84 (dd, J=7.6, 7.1 Hz, 1H), 4.23 (dd, J=6.7, 4.4 Hz, 1H), 5.42 (s, 1H), 5.56 (s, 1H), 6.93-6.83 (m, 4H), 7.41-7.31 (m, 4H).

Example 2

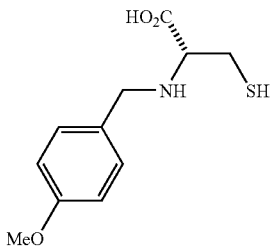

(R)-3-Mercapto-2-(4-methoxybenzylamino)propanoic Acid

A 22 L three-necked round bottom flask fitted with an internal temperature probe and a mechanical stirrer was charged with sodium borohydride (221.3 g, 5.85 mol). Aqueous sodium hydroxide (1.75 L, 0.25 M) was added and the mixture was stirred until homogeneous. The solution was cooled to 0-5° C. The title compound from Example 1 (350.0 g, 1.46 mol) was dissolved in aq $K_2CO_3$ (2.1 L, 0.62 M). This solution was added to the solution of sodium borohydride over 1 h while stirring. The temperature of the reaction was kept below 30° C. during the addition. The reaction was stirred for an additional 1 h period, at which time HPLC analysis showed no remaining starting material. The reaction was cooled to 0° C. and glacial acetic acid (700 mL) was added dropwise with gentle constant stirring (CAUTION: The reaction mixture becomes foamy and evolves gas, and may overflow the reaction flask if acetic acid is not added slowly). The final pH of the reaction mixture was 5. The white solid was collected by filtration, washed with water and ethanol, and dried in a vacuum oven at 50° C. overnight to afford the title compound (240 g, 68%).

$^1$H NMR (DMSO, 300 MHz): δ 2.76 (d, J=5.7 Hz, 2H), 3.24 (dd, J=5.3, 5.3 Hz, 1H), 3.72 (s, 3H), 3.87 (AB, $J_{AB}$=13.1 Hz, $\Delta v_{AB}$=18.5 Hz, 2H), 6.91 (d, 8.9 Hz, 2H), 7.32 (d, 8.9 Hz, 2H).

Example 3

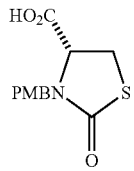

(R)-3-(4-Methoxybenzyl)-2-oxothiazolidine-4-carboxylic Acid

A 22 L three-necked round bottom flask fitted with an internal temperature probe and a mechanical stirrer was charged with the title compound from Example 2 (400.0 g, 1.66 mol), $K_2CO_3$ (480.0 g, 3.47 mol) and water (2.8 L). The mixture was heated at 40° C. while stirring until it became homogeneous and was then cooled to room temperature. A solution of N,N-carbonyldiimidazole (400.0 g, 222.47 mol) in acetonitrile (2.8 L) was added dropwise at a rate that maintained an internal reaction temperature less than 30° C. The reaction was monitored by HPLC and was complete upon the disappearance of the starting material (about 15 minutes). The acetonitrile was removed by heating at 40° C. and 80-100 torr. Isopropyl acetate (200 mL) was added and the pH of the mixture was adjusted to 2 with 3 M $H_2SO_4$. The biphasic mixture was filtered, and the organic phase was isolated. Additional isopropyl acetate was added and the solution was dried by azeotropic distillation. The reaction volume was reduced further until a precipitate began to form. The yellow precipitate was isolated by filtration and dried at 50° C. overnight to afford the title compound (310 g, 70%).

$^1$H NMR (DMSO, 300 MHz): δ 3.36-3.28 (m, 1H), 3.67-3.59 (m, 1H), 3.71 (s, 3H), 4.31-4.24 (m, 1H), 4.52 (AB, $J_{AB}$=15.5 Hz, $\Delta v_{AB}$=238.4 Hz, 2H), 6.88 (d, 8.3 Hz, 2H), 7.15 (d, 8.3 Hz, 2H).

Example 4

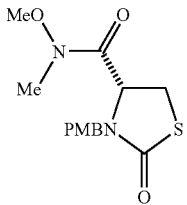

(R)-N-Methoxy-3-(4-methoxybenzyl)-N-methyl-2-oxothiazolidine-4-carboxamide

A 22 L three-necked round bottom flask fitted with an internal temperature probe and a mechanical stirrer was charged with the title compound from Example 3 (310.0 g, 1.16 mol) and isopropyl acetate (2.4 L). The vessel was purged with nitrogen and cooled to 0° C. N-methylmorpholine (130.0 g, 1.29 mol) was added dropwise such that the internal reaction temperature never increased above 5° C. The reaction became cloudy. Pivaloyl chloride (150.0 g, 1.24 mol) was added dropwise such that the internal reaction temperature never increased above 5° C. The reaction was stirred at 0° C. for 45 minutes. N-methoxy-methanamine (78.0 g, 1.28 mol) was added dropwise, again keeping the internal reaction temperature below 5° C. The reaction was monitored by HPLC and was worked up when the ratio of the product to starting material was 4:1 (approximately 30 minutes after amine addition). The mixture was then washed with 0.1 M HCl and satd aq $NaHCO_3$. The organic phase was separated and concentrated to a final volume of 1.0 L by distillation. Upon stirring, a precipitate began to form. A 250 mL portion of n-heptane was added, and the mixture was stirred vigorously. The solid was filtered and dried in a vacuum oven at 40° C. to afford the title compound (250 g, 70%).

$^1$H NMR (DMSO, 300 MHz): δ 3.15 (dd, J=11.0, 5.5 Hz, 1H), 3.21 (s, 3H), 3.38 (s, 3H), 3.46 (dd, J=11.0, 8.5 Hz, 1H), 3.79 (s, 3H), 4.40 (dd, J=8.8, 5.2 Hz, 1H), 4.49 (AB, $J_{AB}$=14.4 Hz, $\Delta v_{AB}$=387.9 Hz, 2H), 6.86 (d, 8.9 Hz, 2H), 7.15 (d, 8.9 Hz, 2H).

Example 5

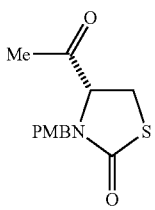

(R)-4-Acetyl-3-(4-methoxybenzyl)thiazolidin-2-one

A dry three-necked round bottom flask fitted with an internal temperature probe and a mechanical stirrer was charged with a solution of methylmagnesium chloride in THF (0.805 L, 3 M). The solution was purged with nitrogen and cooled to 0° C. In a separate flask, the title compound from Example 4 (250.0 g, 0.805 mol) was dissolved in dry THF (1.0 L). This solution was added to the solution of methylmagnesium chloride at a rate that maintained an internal reaction temperature less than 5° C. The reaction was monitored by HPLC and was complete upon the disappearance of the starting material (approx. 20 minutes after completing the addition). The reaction mixture was slowly added into a 10% citric acid solution (1 L) at a rate that maintained a temperature of less than 25° C. The mixture was diluted with water, and the THF was removed by distillation at 70° C. (80° C. external) and 1 atm. The product was extracted with ethyl acetate, and the organic phase was separated and concentrated by distillation at 76° C. (95° C. external) and 1 atm to a final volume of ~800 mL. The solution was allowed to cool to room temperature, and n-heptane was added to give a precipitate. The suspension was stirred for 30 minutes, and the solid was isolated by filtration and dried in a vacuum oven at 40° C. overnight to afford the title compound (170 g, 80%).

$^1$H NMR (DMSO, 300 MHz): δ 2.19 (s, 3H), 3.37 (dd, J=11.8, 2.6 Hz, 1H), 3.62 (dd, J=11.9, 10.0 Hz, 1H), 3.72 (s, 3H), 4.27 (AB, $J_{AB}$=15.2 Hz, $\Delta v_{AB}$=267.3 Hz, 2H), 4.48 (dd, J=

Example 6

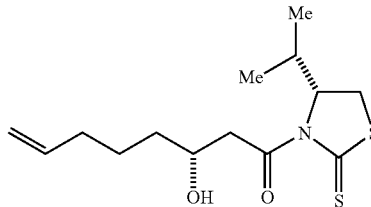

(R)-3-Hydroxy-1-((R)-4-isopropyl-2-thioxothiazolidin-3-yl)oct-7-en-1-one

A solution of (R)-1-(4-isopropyl-2-thioxothiazolidin-3-yl)ethanone (11.8 g, 58.1 mmol) in dichloromethane (380 mL) under an atmosphere of nitrogen was cooled to −78° C., titanium tetrachloride (6.37 mL, 58.1 mmol) was added, and the mixture was stirred for 10 min. Diisopropylethylamine (10.12 mL, 58.1 mmol) was added, and the mixture was stirred for 1 h at −78° C. A 1 M solution of hex-5-enal (58.1 mL, 58.1 mmol) in dichloromethane was added, and the mixture was stirred for 2 h at −78° C. The reaction was quenched by addition of half-saturated $NH_4Cl$ (30 mL) and warmed to room temperature. The mixture was extracted twice with dichloromethane, and the organic phase was dried and evaporated to provide a residue. Chromatography on silica gel afforded the title compound (12.92 g, 74%). This procedure has also been carried out using the (R)-1-(4-benzyl-2-thioxothiazolidin-3-yl)ethanone auxiliary, with a similar result.

Example 7

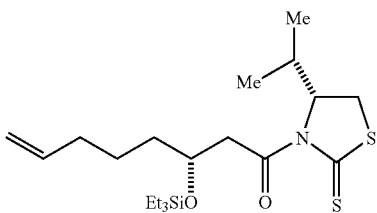

(R)-1-((R)-4-Isopropyl-2-thioxothiazolidin-3-yl)-3-(triethylsflyloxy)oct-7-en-1-one The title compound from Example 6 (4.27 g, 14.2 mmol) was dissolved in DMF (28 mL) under an atmosphere of nitrogen, and diisopropylethylamine (4.94 mL, 28.3 mmol) was added. The mixture was cooled to 0° C., and triethylsilyl chloride (2.57 mL, 14.9 mmol) was added. After stirring for 30 min at 0° C., an additional portion of diisopropylethylamine (1.48 mL, 8.50 mmol) and triethylsilyl chloride (0.73 mL, 4.25 mmol) was added, and the mixture was stirred for 1 h. The mixture was poured onto 10% aq citric acid and extracted with 1:9 ethyl acetate/hexanes. The organic phases were dried and evaporated, and the residue was filtered through a silica plug to provide the title compound (6.08 g, 100%).

$^1$H NMR (CDCl$_3$, 300 MHz): δ 0.60 (q, 6H), 0.92 (t, 9H), 0.96 (d, 3H), 1.08 (d, 3H), 1.64 (m, 4H), 2.04 (m, 2H), 2.40 (sept, 1H), 3.04 (d, 1H), 3.16 (dd, 1H), 3.40-3.60 (m, 2H), 4.32 (m, 1H), 4.92-5.08 (m, 3H), 5.80 (m, 1H).

Example 8

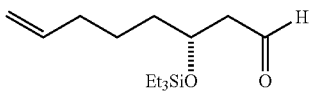

(R)-3-(Triethylsilyloxy)oct-7-enal

The title compound from Example 7 (6.08 g, 14.2 mmol) was dissolved in toluene (70 mL) under an atmosphere of nitrogen and the mixture was cooled to −78° C. DIBAL (1 M in hexane, 32 mL, 32 mmol) was added over 10 min, and the mixture was stirred at −78° C. for 30 min. The reaction mixture was poured onto half-saturated sodium potassium tartrate solution at 0° C. and stirred for 3 h. The phases were separated and the aqueous phase was extracted twice with 1:9 ethyl acetate/hexanes. The combined organic phases were dried and evaporated, and the residue was diluted with hexane. The resulting solid was filtered off and the filtrate was concentrated and filtered through a silica plug to provide the title compound (3.40 g, 93%) as an oil.

$^1$H NMR (CDCl$_3$, 300 MHz): δ 0.60 (q, J=8 Hz, 6H), 0.95 (t, J=8 Hz, 9H), 1.39-1.47 (m, 2H), 1.51-1.63 (m, 2H), 2.05 (q, J=7 Hz, 2H), 2.52 (m, 2H), 4.20 (quint, J=6 Hz, 1H), 4.95-5.04 (m, 2H), 5.78 (m, 1H), 9.81 (t, J=2 Hz, 1H).

Example 9

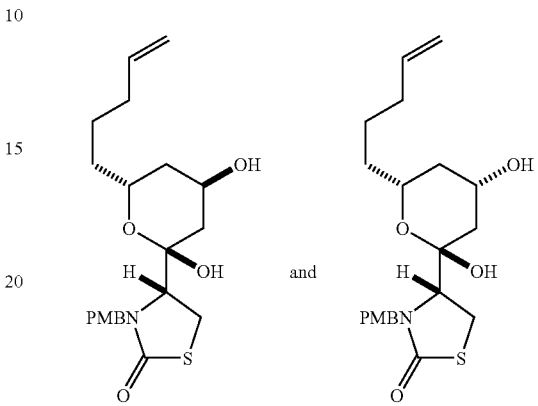

(R)-4-((2R,4R,6R)-2,4-Dihydroxy-6-(pent-4-enyl)-tetrahydro-2H-pyran-2-yl)-3-(4-methoxybenzyl) thiazolidin-2-one and (R)-4-((2R,4S,6R)-2,4-Dihydroxy-6-(pent4-enyl)-tetrahydro-2H-pyran-2-yl)-3-(4-methoxybenzyl)thiazolidin-2-one A solution of the product of Example 5 (4.98 g, 18.8 mmol) in dichloromethane (60 mL) under a nitrogen atmosphere was cooled to −40° C., titanium tetrachloride (2.06 mL, 18.8 mmol) was added, and the mixture was stirred for 5 min. Diisopropylethylamine (3.27 mL, 18.8 mmol) was added, and the reaction was stirred at −40° C. for 5 min, giving a deep red homogeneous solution. A solution of the product of Example 8 (4.81 g, 18.8 mmol) in dichloromethane (3 mL) was added, the mixture was stirred for 15 min at −40° C. The reaction was quenched by the addition of satd aq ammonium chloride solution, warmed to room temperature, and the organic phase was dried and evaporated. Chromatography of the residue on silica gel gave the 4R-isomer (1.9 g, 25%) and the 4S-isomer (2.3 g, 30%) of the title compound.

4R-isomer $^1$H NMR (CDCl$_3$, 300 MHz): δ 1.45-1.69 (m, 5H), 1.77-1.85 (m, 2H), 2.05-2.15 (m, 3H), 2.95 (br s, 1H), 3.30 (dd, J=9, 12, 1H), 3.38 (dd, J=2, 12, 1H), 3.60 (dd, J=2, 9, 1H), 3.79 (s, 3H), 4.21 (m, 1H), 4.34 (d, J=14, 1H), 4.43 (br m, 1H), 4.96-5.07 (m, 2H), 5.07 (d, J=14, 1H), 5.49 (s, 1H), 5.83 (m, 1H), 6.84 (d, J=9, 2H), 7.18 (d, J=9, 2H).
4S-isomer $^1$H NMR (CDCl$_3$, 300 MHz): δ 1.20 (m, 1H), 1.46-1.68 (m, 6H), 2.04-2.16 (m, 2H), 2.22-2.31 (m, 1H), 3.31 (dd, J=9, 12, 1H), 3.39 (dd, J=2, 12, 1H), 3.54 (dd, J=2, 9, 1H), 3.81 (s, 3H), 3.90 (m, 1H), 4.13 (m, 1H), 4.28 (d, J=14, 1H), 4.99-5.03 (m, 2H), 5.16 (d, J=14, 1H), 5.84 (m, 1H), 6.86 (d, J=9, 2H), 7.18 (d, J=9, 2H).

Example 10

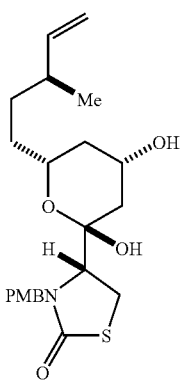

(R)-4-((2R,4S,6R)-2,4-Dihydroxy-6-((S)-3-methyl-pent-4-enyl)-tetrahydro-2H-pyran-2-yl)-3-(4-methoxybenzyl)thiazolidin-2-one Application of the method shown in Example 9, with the modification that (3R,6S)-6-methyl-3-(triethylsilyloxy)oct-7-enal was substituted for (R)-3-(triethylsilyloxy)oct-7-enal, afforded the title compound.

Example 11

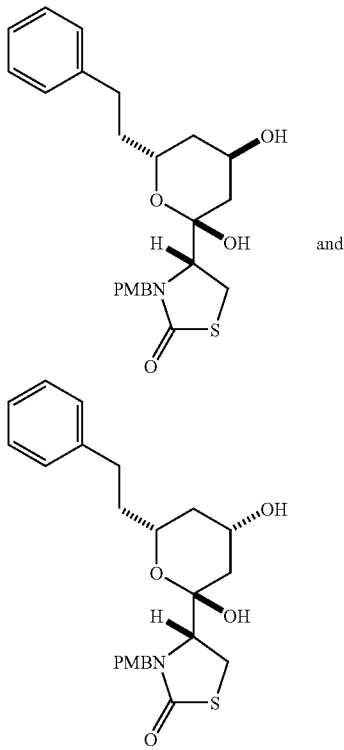

(R)-4-((2R,4R,6R)-2,4-Dihydroxy-6-phenethyl-tetrahydro-2H-pyran-2-yl)-3-(4-methoxybenzyl)thiazolidin-2-one and (R)-4-((2R,4S,6R)-2,4-Dihydroxy-6-phenethyl-tetrahydro-2H-pyran-2-yl)-3-(4-methoxybenzyl)thiazolidin-2-one Application of the method shown in Example 9, with the modification that (R)-5-phenyl-3-(triethylsilyloxy)pentanal was substituted for (R)-3-(triethylsilyloxy)oct-7-enal, affords the title compounds.

Example 12

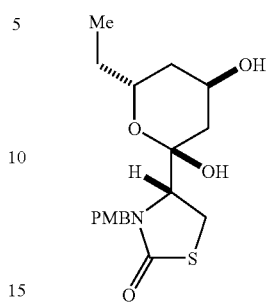

(R)-4-((2R,4R,6R)-6-Ethyl-2,4-dihydroxy-tetrahydro-2H-pyran-2-yl)-3-(4-methoxybenzyl)thiazolidin-2-one Application of the method shown in Example 9, with the modification that (R)-3-(tert-butyldimethylsilyloxy)pentanal was substituted for (R)-3-(triethylsilyloxy)oct-7-enal, afforded the title compound after acid treatment of the intermediate silylated aldol product.

Example 13

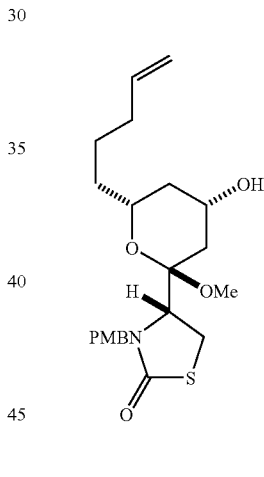

(R)-4-((2R,4S,6R)-4-Hydroxy-2-methoxy-6-(pent-4-enyl)-tetrahydro-2H-pyran-2-yl)-3-(4-methoxybenzyl)thiazolidin-2-one The title compound from Example 9, 4S-isomer (606 mg, 1.49 mmol) was dissolved in toluene (31.5 mL) and methanol (6.02 mL), and a catalytic amount of 10-camphorsulfonic acid (105 mg) was added. The resulting homogeneous solution was stirred at room temperature under a nitrogen atmosphere for 3 hours. The reaction was quenched with satd aq NaHCO$_3$ (20 mL), extracted with 1:1 ethyl acetate/heptane, dried, and concentrated. Chromatography of the residue on silica gel gave the title compound (522 mg, 83%) as an oil.

$^1$H NMR (CDCl$_3$, 300 MHz): δ 1.20 (m, 1H), 1.48-1.59 (m, 4H), 1.61-1.74 (m, 2H), 2.01 (m, 1H), 2.12-2.26 (m, 2H), 3.07 (s, 3H), 3.23-3.28 (m, 2H), 3.60 (m, 1H), 3.81 (s, 3H), 3.83-3.87 (m, 1H), 4.04-4.12 (m, 1H), 4.24 (d, J=14, 1H), 5.01-5.15 (m, 3H), 5.86 (m, 1H), 6.87 (d, J=9, 2H), 7.22 (d, J=9, 2H).

Example 14

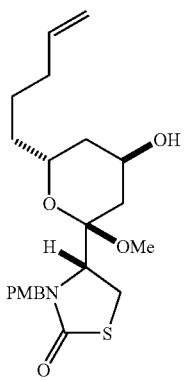

(R)-4-((2R,4R,6R)-4-Hydroxy-2-methoxy-6-(pent-4-enyl)-tetrahydro-2H-pyran-2-yl)-3-(4-methoxybenzyl)thiazolidin-2-one Application of the method shown in Example 13, with the modification that (R)-4-((2R,4R,6R)-2,4-dihydroxy-6-(pent-4-enyl)-tetrahydro-2H-pyran-2-yl)-3-(4-methoxybenzyl)thiazolidin-2-one was substituted for (R)-4-((2R,4S,6R)-2,4-dihydroxy-6-(pent-4-enyl)-tetrahydro-2H-pyran-2-yl)-3-(4-methoxybenzyl)thiazolidin-2-one, afforded the title compound.

Example 15

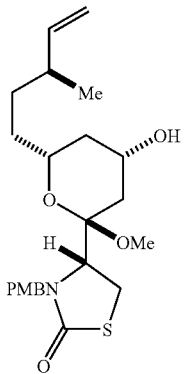

(R)-4-((2R,4S,6R)-4-Hydroxy-2-methoxy-6-((S)-3-methylpent-4-enyl)-tetrahydro-2H-pyran-2-yl)-3-(4-methoxybenzyl)thiazolidin-2-one Application of the method shown in Example 13, with the modification that (R)-4-((2R,4S,6R)-2,4-dihydroxy-6-((S)-3-methylpent-4-enyl)-tetrahydro-2H-pyran-2-yl)-3-(4-methoxybenzyl)thiazolidin-2-one was substituted for (R)-4-((2R,4S,6R)-2,4-dihydroxy-6-(pent-4-enyl)-tetrahydro-2H-pyran-2-yl)-3-(4-methoxybenzyl)thiazolidin-2-one, afforded the title compound.

Example 16

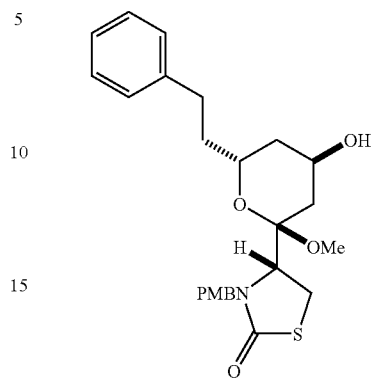

(R)-4-((2R,4R,6R)-4-Hydroxy-2-methoxy-6-phenethyl-tetrahydro-2H-pyran-2-yl)-3-(4-methoxybenzyl)thiazolidin-2-one Application of the method shown in Example 13, with the modification that (R)-4-((2R,4R,6R)-2,4-dihydroxy-6-phenethyl-tetrahydro-2H-pyran-2-yl)-3-(4-methoxybenzyl)thiazolidin-2-one is substituted for (R)-4-((2R,4S,6R)-2,4-dihydroxy-6-(pent-4-enyl)-tetrahydro-2H-pyran-2-yl)-3-(4-methoxybenzyl)thiazolidin-2-one, affords the title compound.

Example 17

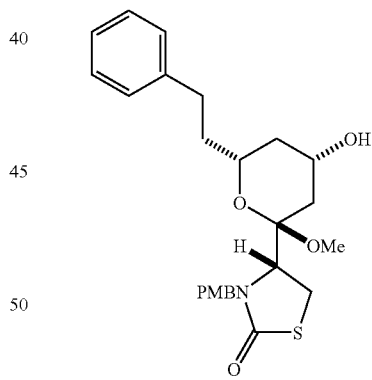

(R)-4-((2R,4S,6R)-4-Hydroxy-2-methoxy-6-phenethyl-tetrahydro-2H-pyran-2-yl)-3-(4-methoxybenzyl)thiazolidin-2-one Application of the method shown in Example 13, with the modification that (R)-4-((2R,4S,6R)-2,4-dihydroxy-6-phenethyl-tetrahydro-2H-pyran-2-yl)-3-(4-methoxybenzyl)thiazolidin-2-one is substituted for (R)-4-((2R,4S,6R)-2,4-dihydroxy-6-(pent-4-enyl)-tetrahydro-2H-pyran-2-yl)-3-(4-methoxybenzyl)thiazolidin-2-one, affords the title compound.

Example 18

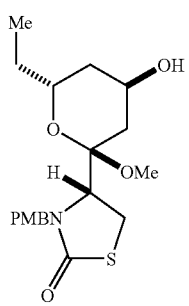

(R)-4-((2R,4R,6R)-6-Ethyl-4-hydroxy-2-methoxy-tetrahydro-2H-pyran-2-yl)-3-(4-methoxybenzyl)thiazolidin-2-one Application of the method shown in Example 13, with the modification that (R)-4-((2R,4R,6R)-6-ethyl-2,4-dihydroxy-tetrahydro-2H-pyran-2-yl)-3-(4-methoxybenzyl)thiazolidin-2-one was substituted for (R)-4-((2R,4S,6R)-2,4-dihydroxy-6-(pent-4-enyl)-tetrahydro-2H-pyran-2-yl)-3-(4-methoxybenzyl)thiazolidin-2-one, afforded the title compound.

Example 19

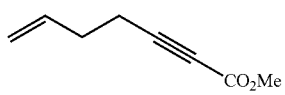

Methyl Hept-6-en-2-ynoate

A solution of allylmagnesium bromide (1M, 150 mL, 150 mmol) in ether under a nitrogen atmosphere was cooled to −10° C., and propargyl chloride (5.4 mL, 75 mmol) was added dropwise. The solution was stirred for 24 h at room temperature, and then cooled to 0° C. Methyl chloroformate was added dropwise, and the solution was allowed to stir at room temperature for 4 h. The reaction was quenched by cautious addition of satd aq NH₄Cl (100 mL) at 0° C. The organic layer was washed with brine, dried, and evaporated to a residue. Chromatography on silica gel provided the title compound (4.5 g, 44%) as a pale yellow liquid.

$^1$H NMR (CDCl$_3$, 300 MHz): δ 2.36 (q, J=7 Hz, 2H), 2.46 (t, J=7 Hz, 2H), 3.79 (s, 3H), 5.08-5.17 (m, 2H), 5.80-5.92 (m, 1H).

Example 20

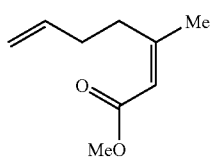

(Z)-Methyl 3-Methylhepta-2,6-dienoate

A suspension of copper(I) iodide (12.38 g, 65 mmol) in 150 mL of dry THF under a nitrogen atmosphere was cooled to −20° C., and methyllithium (1.6 M in ether, 81.5 mL, 130 mmol) was added dropwise over 15 min. The solution was cooled to −78° C., and 4.49 g (32.5 mmol) of the compound from Example 19 in 15 mL of dry THF was added gradually, keeping the temperature below −70° C. After 1 h, 40 mL of ethanol was added cautiously, and the mixture was allowed to warm to room temperature. The mixture was diluted with ether, and washed with satd aq NH₄Cl (200 mL), 5N NH$_3$ (4×250 mL), water (200 mL), and brine (200 mL), dried, and the bulk of the solvent was evaporated to give the title compound (6.8 g, 100%) as an oil. The material had only minor solvent contamination and was adequate for use in the next reaction.

$^1$H NMR (CDCl$_3$, 300 MHz): δ 1.92 (s, 3H), 2.26 (q, J=7 Hz, 2H), 2.76 (t, J=7 Hz, 2H), 3.71 (s, 3H), 4.98-5.10 (m, 2H), 5.71 (s, 1H), 5.80-5.92 (m, 1H).

Example 21

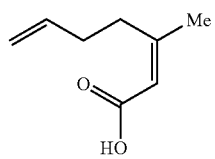

(Z)-3-Methylhepta-2,6-dienoic Acid

A solution of the title compound from Example 20 (6.8 g, 32.5 mmol) in THF (150 mL) was treated with 1 N LiOH (100 mL) and water (125 mL) and stirred vigorously for 4 days. The mixture was diluted with water and washed twice with ether. The aqueous phase was taken to pH 1.5 by addition of 2N HCl and extracted three times with ether. The organic extracts were dried and the solvents evaporated to give the title compound (2.57 g, 56%) as a pale yellow oil.

$^1$H NMR (CDCl$_3$, 300 MHz): δ 1.96 (s, 3H), 2.27 (q, J=8 Hz, 2H), 2.77 (t, J=8 Hz, 2H), 5.02-5.10 (m, 2H), 5.74 (s, 1H), 5.80-5.92 (m, 1H).

Example 22

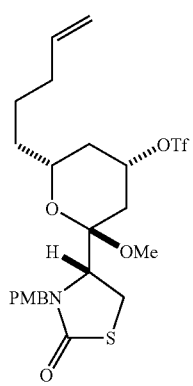

(2R,4S,6R)-2-Methoxy-2-((R)-3-(4-methoxybenzyl)-2-oxothiazolidin-4-yl)-6-(pent-4-enyl)-tetrahydro-2H-pyran-4-yl Trifluoromethanesulfonate To a 50 mL dry flask with Nitrogen and a stir bar was added the title compound from Example 13 (500 mg, 1.19 mmol), 2,6-lutidine (0.687 mL, 5.93 mmol), and dichloromethane (15 mL). After being cooled down to −11° C., trifluoromethanesulfonic anhydride (0.399 mL, 2.37 mmol) was added dropwise via a syringe. The resulted homogeneous solution was stirred at that temperature for 30 minutes. The reaction was quenched with 10% aq citric acid (4 mL), extracted twice with dichloromethane, and dried over Na$_2$SO$_4$ and concentrated. Evaporation of the solvent gave the title compound as an oil, which was used in the next reaction without any further purification.

Example 23

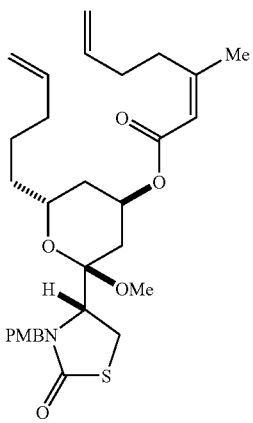

(Z)-((2R,4R,6R)-2-Methoxy-2-((R)-3-(4-methoxybenzyl)-2-oxothiazolidin-4-yl)-6-(pent-4-enyl)-tetrahydro-2H-pyran4-yl)-3-Methylhepta-2,6-dienoate A 100 mL dry flask under a nitrogen atmosphere was charged with NaH (60% in mineral oil, 186 mg, 4.65 mmol). The NaH was washed with pentane (5 mL), THF (2 mL) was added, and the reaction was cooled to 0° C. The title compound from Example 21 (651 mg, 4.65 mmol) in THF (3 mL) was added dropwise, after which 15-crown-5 (1.41 mL, 7.12 mmol) was added. The reaction was allowed to warm to room temperature and stirred for 10 minutes, and then was cooled to 0° C. again. A solution of the title compound from Example 22 (1.19 mmol, used directly from the previous reaction) in THF (2 mL) was added, and the reaction was stirred at room temperature overnight.

The reaction was quenched with satd aq NH$_4$Cl (10 mL), extracted with 1:1 ethyl acetate/heptane, dried over Na$_2$SO$_4$, and concentrated. Chromatography of the residue on silica gel first with 1/4 ethyl acetate/heptane and then with 3/97 ethyl acetate/dichloromethane gave the title compound as an oil (387 mg, 60%).

$^1$H NMR (CDCl$_3$, 300 MHz): δ 1.45-1.96 (m, 7H), 1.90 (d, J=1, 3H), 2.09-2.20 (m, 3H), 2.21-2.28 (m, 2H), 2.75 (t, J=8, 2H), 3.12 (s, 3H), 3.21-3.27 (m, 2H), 3.80-3.89 (m, 1H), 3.82 (s, 3H), 3.93 (m, 1H), 4.28 (d, J=14, 1H), 4.96-5.13 (m, 5H), 5.21 (br m, 1H), 5.70 (s, 1H), 5.78-5.93 (m, 1H), 6.87 (d, J=9, 2H), 7.22 (d, J=9, 2H).

Example 24

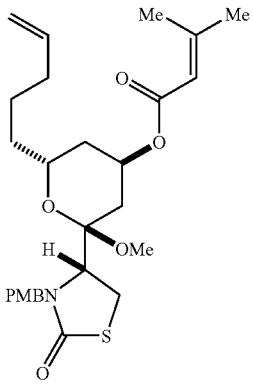

(2R,4R,6R)-2-Methoxy-2-((R)-3-(4-methoxybenzyl)-2-oxothiazolidin-4-yl)-6-(pent-4-enyl)-tetrahydro-2H-pyran-4-yl 3-Methylbut-2-enoate Application of the method shown in Example 23, with the modification that 3-methyl-2-butenoic acid is substituted for (Z)-3-methylhepta-2,6-dienoic acid, affords the title compound.

Example 25

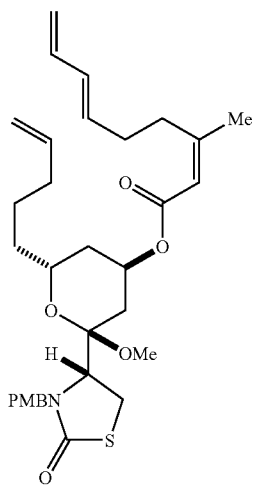

(2Z,6E)-((2R,4R,6R)-2-methoxy-2-((R)-3-(4-methoxybenzyl)-2-oxothiazolidin-4-yl)-6-(pent-4-enyl)-tetrahydro-2H-pyran-4-yl)-3-Methylnona-2,6,8-trienoate Application of the method shown in Example 23, with the modification that (2Z,6E)-3-methylnona-2,6,8-trienoic acid is substituted for (Z)-3-methylhepta-2,6-dienoic acid, affords the title compound.

Example 26

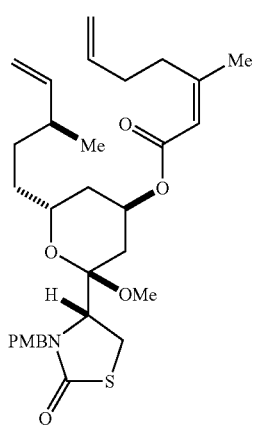

(Z)-((2R,4R,6R)-2-Methoxy-2-((R)-3-(4-methoxybenzyl)-2-oxothiazolidin-4-yl)-6-((S)-3-methylpent-4-enyl)-tetrahydro-2H-pyran-4-yl)-3-Methylhepta-2,6-dienoate Triflate formation using the method shown in Example 22, with the modification that (R)-4-((2R,4S,6R)-4-hydroxy-2-methoxy-6-((S)-3-methylpent-4-enyl)-tetrahydro- 2H-pyran-2-yl)-3-(4-methoxybenzyl)thiazolidin-2-one was substituted for (R)-4-((2R,4S,6R)-4-hydroxy-2-methoxy-6-(pent-4-enyl)-tetrahydro-2H-pyran-2-yl)-3-(4-methoxybenzyl)thiazolidin-2-one, followed by triflate displacement using the method shown in Example 23, afforded the title compound.

Example 27

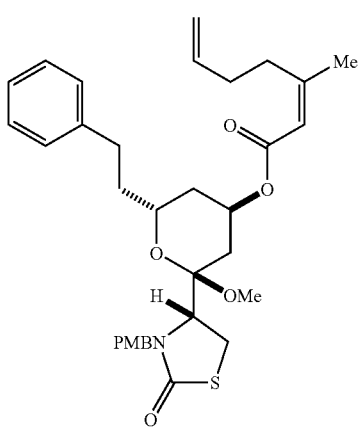

(Z)-((2R,4R,6R)-2-Methoxy-2-((R)-3-(4-methoxybenzyl)-2-oxothiazolidin-4-yl)-6-phenethyl-tetrahydro-2H-pyran4-yl)-3-Methylhepta-2,6-dienoate Triflate formation using the method shown in Example 22, with the modification that (R)-4-((2R,4S,6R)-4-hydroxy-2-methoxy-6-phenethyl-tetrahydro-2H-pyran-2-yl)-3-(4-methoxybenzyl)thiazolidin-2-one is substituted for (R)-4-((2R,4S,6R)-4-hydroxy-2-methoxy-6-(pent-4-enyl)-tetrahydro-2H-pyran-2-yl)-3-(4-methoxybenzyl)thiazolidin-2-one, followed by triflate displacement using the method shown in Example 23, affords the title compound.

Example 28

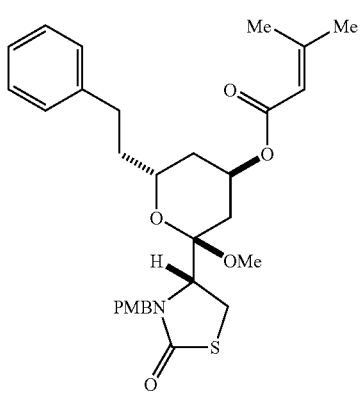

(2R,4R,6R)-2-Methoxy-2-((R)-3-(4-methoxybenzyl)-2-oxothiazolidin-4-yl)-6-phenethyl-tetrahydro-2H-pyran4-yl 3-Methylbut-2-enoate Triflate formation using the method shown in Example 22, with the modification that (R)-4-((2R,4S,6R)-4-hydroxy-2-methoxy-6-phenethyl-tetrahydro-2H-pyran-2-yl)-3-(4-methoxybenzyl)thiazolidin-2-one is substituted for (R)-4-((2R,4S,6R)-4-hydroxy-2-methoxy-6-(pent-4-enyl)-tetrahydro-2H-pyran-2-yl)-3-(4-methoxybenzyl)thiazolidin-2-one, followed by triflate displacement using the method shown in Example 23, with the modification that 3-methyl-2-butenoic acid is substituted for (Z)-3-methylhepta-2,6-dienoic acid, affords the title compound.

Example 29

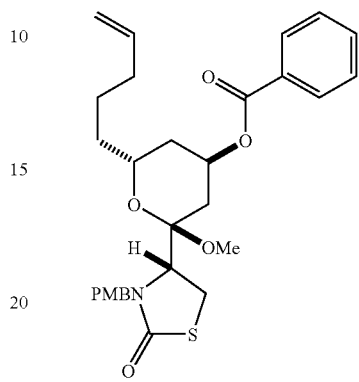

(2R,4R,6R)-2-Methoxy-2-((R)-3-(4-methoxybenzyl)-2-oxothiazolidin-4-yl)-6-(pent-4-enyl)-tetrahydro-2H-pyran-4-yl Benzoate To a solution of benzoic acid (31.7 mg, 0.260 mmol) in dry toluene (5 mL) under a nitrogen atmosphere was added diisopropylethylamine (0.0435 mL, 0.250 mmol) and 2,4,6-trichlorobenzoyl chloride (0.0391 mL, 0.250 mmol). The mixture was stirred at room temperature for 3 h, after which the title compound from Example 14 (21.5 mg, 0.051 mmol) and DMAP (32.9 mg, 0.269 mmol) were added. This mixture was stirred at room temperature for 18 h, after which it was diluted with ether and washed with satd aq $NH_4Cl$ and brine, and the organic phase was dried and evaporated. Chromatography of the residue on silica gel, eluting with an ethyl acetate/dichloromethane gradient, afforded the title compound (21.7 mg, 81%) as an oil.

Example 30

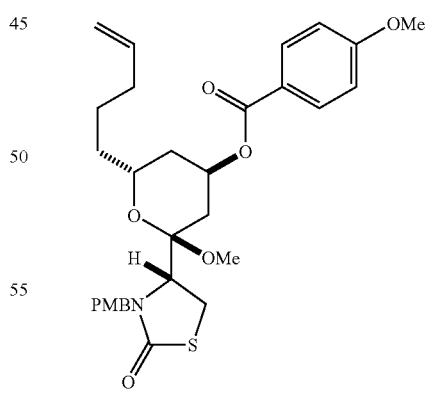

(2R,4R,6R)-2-Methoxy-2-((R)-3-(4-methoxybenzyl)-2-oxothiazolidin4-yl)-6-(pent-4-enyl)-tetrahydro-2H-pyran4-yl 4-Methoxybenzoate Application of the method shown in Example 29, with the modification that 4-methoxybenzoic acid was substituted for benzoic acid, afforded the title compound.

Example 31

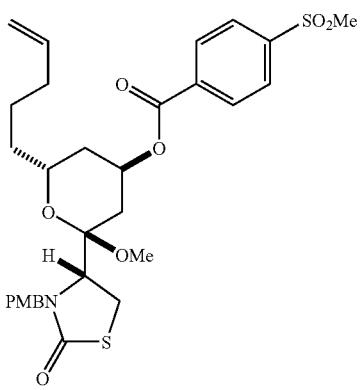

(2R,4R,6R)-2-Methoxy-2-((R)-3-(4-methoxybenzyl)-2-oxothiazolidin-4-yl)-6-(pent-4-enyl)-tetrahydro-2H-pyran4-yl 4-(Methylsulfonyl)benzoate Application of the method shown in Example 29, with the modification that 4-methylsulfonylbenzoic acid was substituted for benzoic acid, afforded the title compound.

Example 32

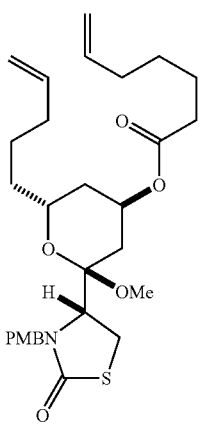

(2R,4R,6R)-2-Methoxy-2-((R)-3-(4-methoxybenzyl)-2-oxothiazolidin-4-yl)-6-(pent-4-enyl)-tetrahydro-2H-pyran-4-yl Hept-6enoate Application of the method shown in Example 29, with the modification that 6-heptenoic acid was substituted for benzoic acid, afforded the title compound.

Example 33

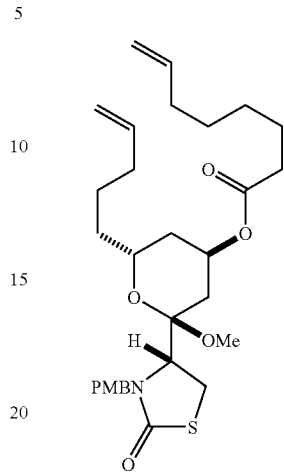

(2R,4R,6R)-2-Methoxy-2-((R)-3-(4-methoxybenzyl)-2-oxothiazofidin-4-yl)-6-(pent-4-enyl)-tetrahydro-2H-pyran4-yl Oct-7-enoate Application of the method shown in Example 29, with the modification that 6-octenoic acid was substituted for benzoic acid, afforded the title compound.

Example 34

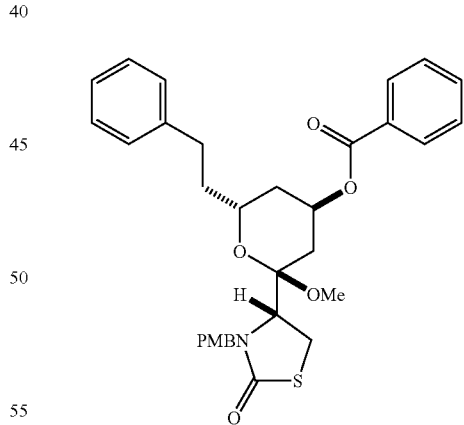

(2R,4R,6R)-2-Methoxy-2-((R)-3-(4-methoxybenzyl)-2-oxothiazolidin-4-yl)-6-phenethyl-tetrahydro-2H-pyran-4-yl Benzoate Application of the method shown in Example 29, with the modification that (R)-4-((2R,4R,6R)-4-hydroxy-2-methoxy- 6-phenethyl-tetrahydro-2H-pyran-2-yl)-3-(4-methoxybenzyl)thiazolidin-2-one is substituted for (R)-4-((2R,4R,6R)-4-hydroxy-2-methoxy-6-(pent-4-enyl)-tetrahydro-2H-pyran-2-yl)-3-(4-methoxybenzyl)thiazolidin-2-one, affords the title compound.

Example 35

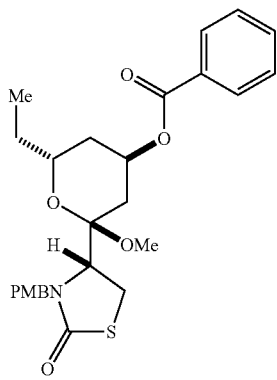

(2R,4R,6R)-6-Ethyl-2-methoxy-2-((R)-3-(4-methoxybenzyl)-2-oxothiazolidin-4-yl)-tetrahydro-2H-pyran-4-yl Benzoate Application of the method shown in Example 29, with the modification that (R)-4-((2R,4R,6R)-6-ethyl-4-hydroxy-2-methoxy-tetrahydro-2H-pyran-2-yl)-3-(4-methoxybenzyl)thiazolidin-2-one was substituted for (R)-4-((2R,4R,6R)-4-hydroxy-2-methoxy-6-(pent-4-enyl)-tetrahydro-2H-pyran-2-yl)-3-(4-methoxybenzyl)thiazolidin-2-one, afforded the title compound.

Example 36

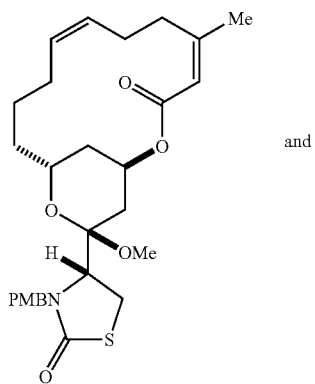

and

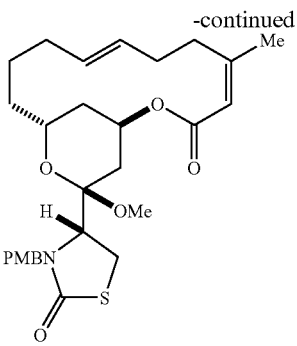

-continued (R)-4-((1R,4Z,8Z,13R,15R)-15-Methoxy-5-methyl-3-oxo-2,14-dioxa-bicyclo[11.3.1]heptadeca-4,8-dien-15-yl)-3-(4-methoxybenzyl)thiazolidin-2-one and (R)-4-((1R,4Z,8E,13R,15R)-15-Methoxy-5-methyl-3-oxo-2,14-dioxa-bicyclo[11.3.1]heptadeca4,8-dien-15-yl)-3-(4-methoxybenzyl)thiazolidin-2-one To a 250 mL dry flask was added the title compound from Example 23 (387 mg, 0.712 mmol) and dichloromethane (70 mL). Nitrogen was bubbled through the mixture for 30 minutes to degas the solution. The bubbling was continued while the solution was heated 20 briefly to reflux and then cooled to room temperature. The bubbling was stopped, a solution of second generation Grubbs catalyst (30.2 mg, 0.036 mmol) in dichloromethane (4 mL), was added, and the reaction was stirred at room temperature for 14 hours. The reaction was then quenched by the addition of DMSO (0.1 mL) followed by stirring open to the atmosphere for 24 hours. Concentration of the mixture and chromatography of the residue on silica gel, eluting with 3/49/49 ethyl acetate/dichloromethane/heptane gave the title compound (290 mg, 79%) as a 1:1 mixture of its E- and Z-isomers, as an white solid.

The mixture of E- and Z-isomers was separated through supercritical fluid chromatography (SFC) on a CHIRAL-PAK AS—H column. Concentration gave the individual title compounds as white solids.

8Z-isomer $^1$H NMR (CDCl$_3$, 300 MHz): δ 1.20-1.35 (m, 3H), 1.42-1.74 (m, 5H), 1.80-1.92 (m, 2H), 1.92 (s, 3H), 2.20-2.32 (m, 3H), 2.88 (m, 1H), 3.08 (s, 3H), 3.14-3.24 (m, 2H), 3.74-3.81 (m, 1H), 3.81 (s, 3H), 4.21-4.29 (m, 1H), 4.30 (d, J=14, 1H), 5.08 (d, J=14, 1H), 5.26 (m, 1H), 5.42 (m, 2H), 5.65 (s, 1H), 6.87 (d, J=9, 2H), 7.24 (d, J=9, 2H).

8E-isomer $^1$H NMR (CDCl$_3$, 300 MHz): δ 1.21-1.44 (m, 3H), 1.54-1.78 (m, 5H), 1.83-2.07 (m, 2H), 1.90 (s, 3H), 2.08-2.41 (m, 3H), 3.11 (s, 3H), 3.14-3.25 (m, 3H), 3.69-3.81 (m, 1H), 3.82 (s, 3H), 4.29 (d, J=14, 1H), 4.51 (m, 1H), 5.08 (d, J=14, 1H), 5.22 (m, 1H), 5.46 (m, 2H), 6.23 (s, 1H), 6.87 (d, J=9, 2H), 7.24 (d, J=9, 2H).

Example 37

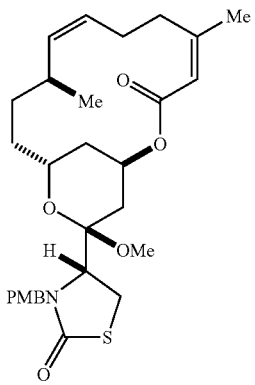

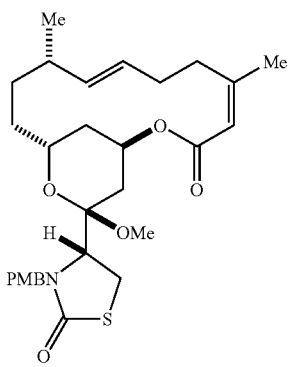

(R)-4-((1R,4Z,8Z,10S,13R,15R)-15-Methoxy-5,10-dimethyl-3-oxo-2,14-dioxa-bicyclo[11.3.1]heptadeca-4,8-dien-15-yl)-3-(4-methoxybenzyl)thiazolidin-2-one and (R)-4-((1R,4Z,8E,10S,13R,15R)-15-Methoxy-5,10-dimethyl-3-oxo-2,14-dioxa-bicyclo[11.3.1]heptadeca-4,8-dien-15-yl)-3-(4-methoxybenzyl)thiazolidin-2-one Application of the method shown in Example 36, with the modification that (Z)-((2R,4R,6R)-2-methoxy-2-((R)-3-(4-methoxybenzyl)-2-oxothiazolidin-4-yl)-6-((S)-3-methyl-pent-4-enyl)-tetrahydro-2H-pyran-4-yl)-3-methylhepta-2,6-dienoate was substituted for (Z)-((2R,4R,6R)-2-methoxy-2-((R)-3-(4-methoxybenzyl)-2-oxothiazolidin-4-yl)-6-(pent-4-enyl)-tetrahydro-2H-pyran-4-yl)-3-methylhepta-2,6-dienoate, afforded the title compounds.

Example 38

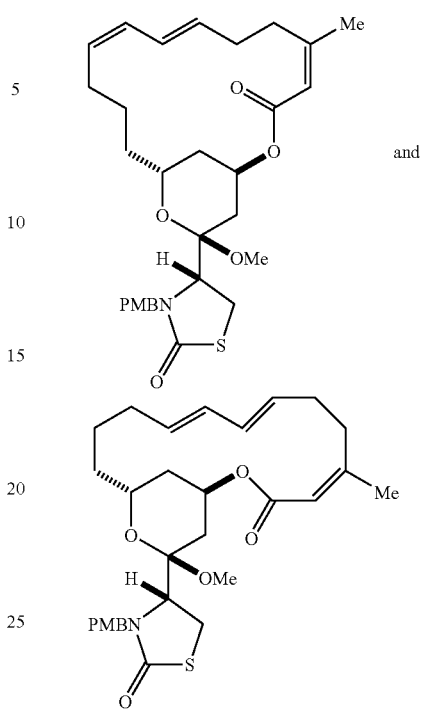

(R)4-((1R,4Z,8E,10Z,15R,17R)-17-Methoxy-5-methyl-3-oxo-2,16-dioxa-bicyclo[13.3.1]nonadeca-4,8,10-trien-17-yl)-3-(4-methoxybenzyl)thiazolidin-2-one and (R)-4-((1R,4Z,8E,10E,15R,17R)-17-Methoxy-5-methyl-3-oxo-2,16-dioxa-bicyclo[13.3.1]nonadeca4,8,10-trien-17-yl)-3-(4-methoxybenzyl)thiazolidin-2-one Application of the method shown in Example 36, with the modification that (2Z,6E)-((2R,4R,6R)-2-methoxy-2-((R)-3-(4-methoxybenzyl)-2-oxothiazolidin-4-yl)-6-(pent-4-enyl)-tetrahydro-2H-pyran-4-yl)-3-methylnona-2,6,8-trienoate is substituted for (Z)-((2R,4R,6R)-2-methoxy-2-((R)-3-(4-methoxybenzyl)-2-oxothiazolidin-4-yl)-6-(pent-4-enyl)-tetrahydro-2H-pyran-4-yl)-3-methylhepta-2,6-dienoate, affords the title compounds.

Example 39

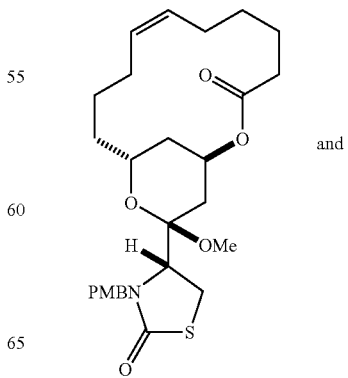

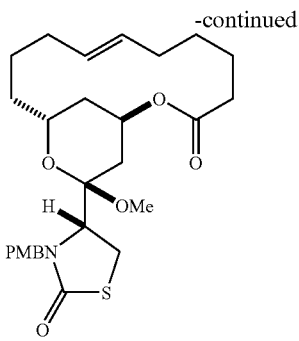

(R)-4-((1R,13R,15R,Z)-15-Methoxy-3-oxo-2,14-dioxa-bicyclo[11.3.1]heptadec-8-en-15-yl)-3-(4-methoxybenzyl)thiazolidin-2-one and (R)4-((1R,13R,15R,E)-15-Methoxy-3-oxo-2,14-dioxa-bicyclo[11.3.1]heptadec-8-en-15-yl)-3-(4-methoxybenzyl)thiazolidin-2-one Application of the method shown in Example 36, with the modification that (2R,4R,6R)-2-methoxy-2-((R)-3-(4-methoxybenzyl)-2-oxothiazolidin-4-yl)-6-(pent-4-enyl)-tetrahydro-2H-pyran-4-yl hept-6-enoate was substituted for (Z)-((2R,4R,6R)-2-methoxy-2-((R)-3-(4-methoxybenzyl)-2-oxothiazolidin-4-yl)-6-(pent-4-enyl)-tetrahydro-2H-pyran-4-yl) 3-methylhepta-2,6-dienoate, afforded the title compounds.

Example 40

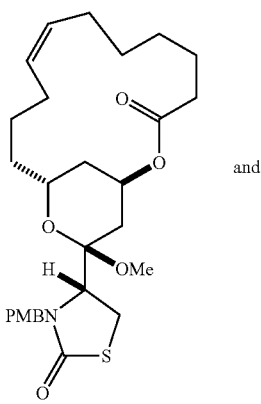

and

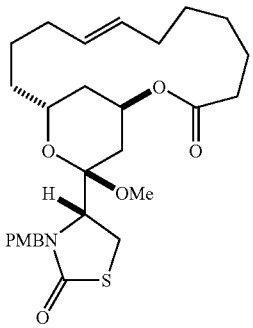

(R)-4-((1R,14R,16R,Z)-16-Methoxy-3-oxo-2,15-dioxa-bicyclo[12.3.1]octadec-9-en-16-yl)-3-(4-methoxybenzyl)thiazolidin-2-one and (R)4-((1R,14R,16R,E)-16-Methoxy-3-oxo-2,15-dioxa-bicyclo[12.3.1]octadec-9-en-16-yl)-3-(4-methoxybenzyl)thiazolidin-2-one Application of the method shown in Example 36, with the modification that (2R,4R,6R)-2-methoxy-2-((R)-3-(4-methoxybenzyl)-2-oxothiazolidin-4-yl)-6-(pent-4-enyl)-tetrahydro-2H-pyran-4-yl oct-7-enoate was substituted for (Z)-((2R,4R,6R)-2-methoxy-2-((R)-3-(4-methoxybenzyl)-2-oxothiazolidin-4-yl)-6-(pent-4-enyl)-tetrahydro-2H-pyran-4-yl) 3-methylhepta-2,6-dienoate, afforded the title compounds.

Example 41

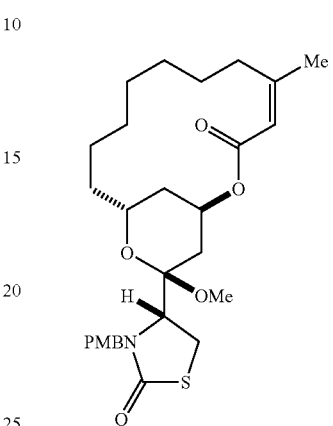

(R)-4-((1R,13R,15R,Z)-15-Methoxy-5-methyl-3-oxo-2,14-dioxa-bicyclo[11.3.1]heptadec-4-en-15-yl)-3-(4-methoxybenzyl)thiazolidin-2-one A solution of the title compound from Example 36 (12.4 mg, 0.024 mmol, a mixture 20 of E- and Z-isomers) in ethanol (1 mL) and ethyl acetate (3 mL) was flushed with nitrogen, and 10% Pd/C (8.1 mg) was added as a slurry in a small volume of water. The atmosphere was replaced with hydrogen, and the mixture was stirred for 22 h. The mixture was filtered and evaporated. Chromatography of the residue on a C18 reversed phase column, eluting with acetonitrile/water, afforded the title compound (5.0 mg, 40%) as a solid.

Example 42

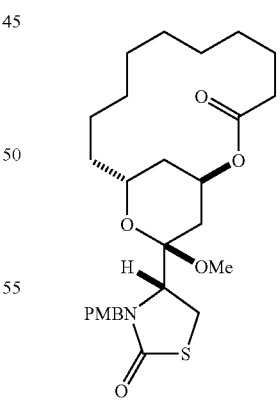

(R)-4-((1R,13R,15R)-15-Methoxy-3-oxo-2,14-dioxa-bicyclo[11.3.1]heptadecan-15-yl)-3-(4-methoxybenzyl)thiazolidin-2-one Application of the method shown in Example 41, with the modification that (R)-4-((1R,13R,15R,Z)-15-methoxy-3- oxo-2,14-dioxa-bicyclo[11.3.1]heptadec-8-en-15-yl)-3-(4-methoxybenzyl)thiazolidin-2-one was substituted for (R)-4-((1R,4Z, 13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

Example 43

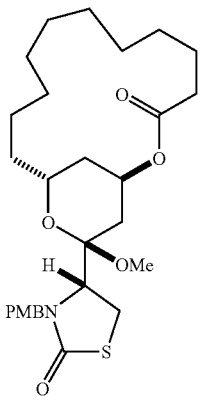

(R)-4-((1R,14R,16R)-16-Methoxy-3-oxo-2,15-di-oxa-bicyclo[12.3.1]octadecan-16-yl)-3-(4-methoxy-benzyl)thiazolidin-2-one Application of the method shown in Example 41, with the modification that (R)-4-((1R,14R,16R,E)-16-methoxy-3-oxo-2,15-dioxa-bicyclo[12.3.1]octadec-9-en-16-yl)-3-(4-methoxybenzyl)thiazolidin-2-one was substituted for (R)-4-((1R,4Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

Example 44

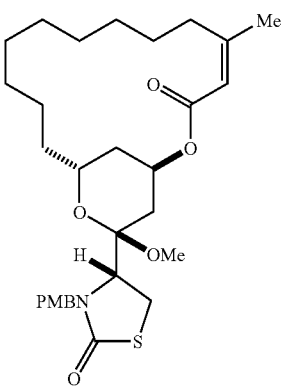

(R)-4-((1R,15R,17R,Z)-17-Methoxy-5-methyl-3-oxo-2,16-dioxa-bicyclo[13.3.1]nonadec-4-en-17-yl)-3-(4-methoxybenzyl)thiazolidin-2-one Application of the method shown in Example 41, with the modification that (R)-4-((1R,4Z,8E,10Z,15R,17R)-17-methoxy-5-methyl-3-oxo-2, 16-dioxa-bicyclo[13.3.1]nonadeca-4,8,10-trien-17-yl)-3-(4-methoxybenzyl)thiazolidin-2-one is substituted for (R)-4-((1R,4Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, affords the title compound.

Example 45

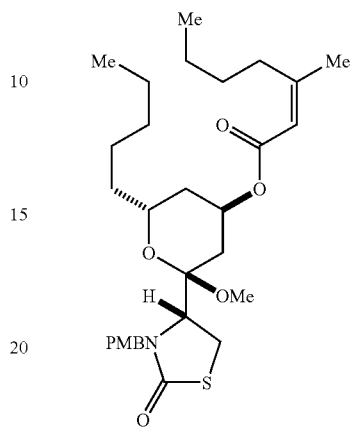

(Z)-((2R,4R,6R)-2-Methoxy-2-((R)-3-(4-methoxy-benzyl)-2-oxothiazolidin-4-yl)-6-pentyl-tetrahydro-2H-pyran4-yl)-3-Methylhept-2-enoate Application of the method shown in Example 41, with the modification that (Z)-((2R,4R,6R)-2-methoxy-2-((R)-3-(4-methoxybenzyl)-2-oxothiazolidin-4-yl)-6-(pent-4-enyl)-tetrahydro-2H-pyran-4-yl)-3-methylhepta-2,6-dienoate is substituted for (R)-4-((1R,4Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, affords the title compound.

Example 46

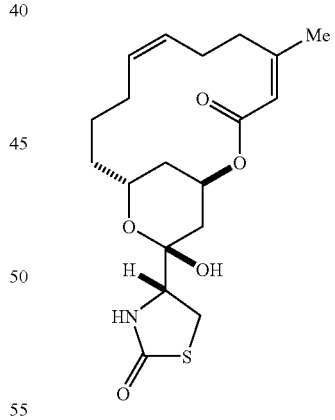

(R)-4-((1R,4Z,8Z,13R,15R)-15-Hydroxy-5-methyl-3-oxo-2,14-dioxa-bicyclo[11.3.1]heptadeca-4,8-dien-15-yl)thiazolidin-2-one, Compound 8

To a solution of the title compound from Example 36, 8Z-isomer (13.3 mg, 0.026 mmol) in acetonitrile (0.266 mL) was added a solution of ceric ammonium nitrate (36 mg, 0.064 mmol) in water (0.133 mL). The reaction was stirred at room temperature for 2 hours, after which the mixture was diluted with dichloromethane, washed with satd aq NaHCO$_3$, and the organic phase was dried and concentrated. Chromatography of the residue on silica gel eluting with an ethyl acetate/heptane gradient gave the title compound (6.2 mg, 63%) of as a white solid.

¹H NMR (CDCl₃, 300 MHz): δ 1.22-1.34 (m, 2H), 1.38-1.61 (m, 3H), 1.75-1.85 (m, 2H), 1.93 (s, 3H), 2.00-2.14 (m, 2H), 2.20-2.28 (m, 3H), 2.31-2.46 (m, 1H), 2.49-2.62 (m, 1H), 3.36-3.50 (m, 2H), 3.65 (br s, 1H), 3.82 (m, 1H), 4.28 (m, 1H), 5.26-5.41 (m, 2H), 5.46 (m, 1H), 5.69 (m, 2H).

Example 47

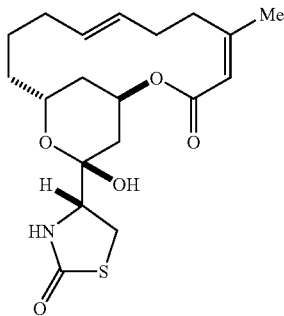

(R)-4-((1R,4Z,8E,13R,15R)-15-Hydroxy-5-methyl-3-oxo-2,14-dioxa-bicyclo[11.3.1]heptadeca-4,8-dien-15-yl)thiazolidin-2-one, Compound 8a Application of the method shown in Example 46, with the modification that (R)-4-((1R,4Z,8E,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one was substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

¹H NMR (CDCl₃, 300 MHz): δ 1.25-1.48 (m, 3H), 1.56-1.77 (m, 3H), 1.89 (d, J-1 Hz, 3H), 2.01-2.12 (m, 3H), 2.13-2.25 (m, 3H), 2.46 (quin, J=6 Hz, 3H), 2.75 (dt, J=12, 8 Hz, 1H), 3.40 (dd, J=6, 12 Hz, 1H), 3.49 (dd, J=9, 12 Hz, 1H), 3.82 (dd, J=6, 9 Hz, 1H), 3.94 (br s, 1H), 4.40 (m, 1H), 5.30-5.48 (m, 3H), 5.66 (s, 1H), 5.72 (s, 1H).

Example 48

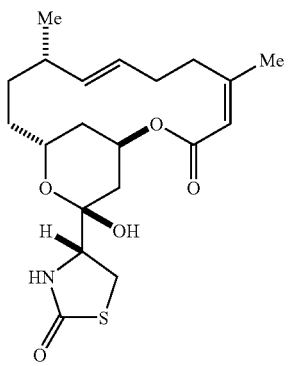

(R)-4-((1R,4Z,8E,10S,13R,15R)-15-Hydroxy-5,10-dimethyl-3-oxo-2,14-dioxa-bicyclo[11.3.1]heptadeca-4,8-dien-15-yl)thiazolidin-2-one, Compound 8b Application of the method shown in Example 46, with the modification that (R)-4-((1R,4Z,8E,10S,13R,15R)-15-methoxy-5,10-dimethyl-3-oxo-2,14-dioxa-bicyclo[11.3.1]heptadeca-4,8-dien-15-yl)-3-(4-methoxybenzyl)thiazolidin-2-one was substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

¹H NMR (CDCl₃, 300 MHz): δ 0.96 (d, J=7 Hz, 3H), 1.20-1.47 (m, 3H), 1.55-1.68 (m, 3H), 1.89 (d, J=1 Hz, 3H), 2.01-2.17 (m, 3H), 2.22-2.35 (m, 2H), 2.39-2.48 (m, 1H), 2.64-2.72 (m, 1H), 3.40 (dd, J=6, 12 Hz, 1H), 3.49 (dd, J=9, 12 Hz, 1H), 3.82 (dd, J=6, 9 Hz, 1H), 4.04 (s, 1H), 4.35 (m, 1H), 5.22-5.39 (m, 3H), 5.67 (s, 1H), 5.75 (s, 1H).

Example 49

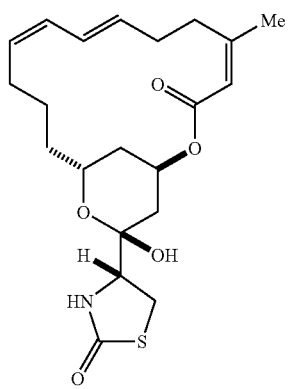

(R)4-((1R,4Z,8E,10Z,15R,17R)-17-Hydroxy-5-methyl-3-oxo-2,16-dioxa-bicyclo[13.3.1]nonadeca-4,8,10-trien-17-yl)thiazolidin-2-one, Compound 9

Application of the method shown in Example 46, with the modification that (R)-4-((1R,4Z,8E,10Z,15R,17R)-17-methoxy-5-methyl-3-oxo-2,16-dioxa-bicyclo[13.3.1]nonadeca-4,8,10-trien-17-yl)-3-(4-methoxybenzyl)thiazolidin-2-one is substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, affords the title compound.

Example 50

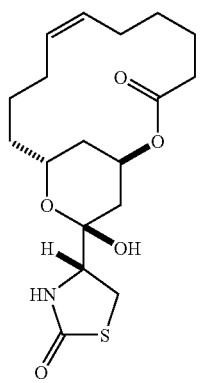

(R)4-((1R,13R,15R,Z)-15-Hydroxy-3-oxo-2,14-dioxa-bicyclo[11.3.1]heptadec-8-en-15-yl)thiazolidin-2-one, Compound 10a Application of the method shown in Example 46, with the modification that (R)-4-((1R,13R,15R,Z)-15-methoxy-3- oxo-2,14-dioxa-bicyclo[11.3.1]heptadec-8-en-15-yl)-3-(4-methoxybenzyl)thiazolidin-2-one was substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

$^1$H NMR (CDCl$_3$, 300 MHz): δ 1.30-1.75 (m, 8H), 1.75-2.10 (m, 6H), 2.15-2.50 (m, 3H), 2.55-2.65 (m, 1H), 3.41 (dd, J=6, 12 Hz, 1H), 3.52 (dd, J=9, 12 Hz, 1H), 3.87 (dd, J=6, 9 Hz, 1H), 4.11 (m, 1H), 4.25 (br s, 1H), 5.23 (m, 1H), 5.41 (m, 2H), 5.62 (br s, 1H).

Example 51

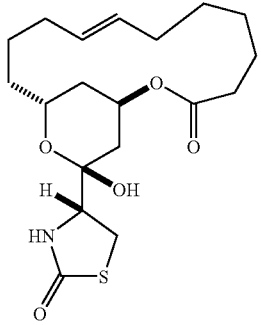

(R)-4-((1R,14R,16R,E)-16-Hydroxy-3-oxo-2,15-dioxa-bicyclo[12.3.1]octadec-9-en-16-yl)thiazolidin-2-one, Compound 10c Application of the method shown in Example 46, with the modification that (R)-4-((1R,14R,16R,E)-16-methoxy-3-oxo-2,15-dioxa-bicyclo[12.3.1]octadec-9-en-16-yl)-3-(4-methoxybenzyl)thiazolidin-2-one was substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

$^1$H NMR (CDCl$_3$, 300 MHz): δ 1.17-1.51 (m, 8H), 1.56-1.73 (m, 4H), 1.91-2.08 (m, 5H), 2.25-2.46 (m, 3H), 3.43 (dd, J=6, 12 Hz, 1H), 3.51 (dd, J=9, 12 Hz, 1H), 3.87 (dd, J=6, 8 Hz, 1H), 4.14 (m, 1H), 4.35 (s, 1H), 5.29 (m, 1H), 5.31-5.46 (m, 2H), 5.82 (s, 1H).

Example 52

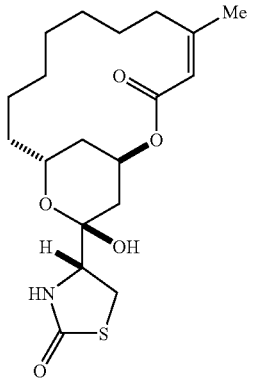

(R)-4-((1R,13R,15R,Z)-15-]Hydroxy-5-methyl-3-oxo-2,14-dioxa-bicyclo[11.3.1]heptadec-4-en-15-yl)thiazolidin-2-one, Compound 10

Application of the method shown in Example 46, with the modification that (R)4-((1R,13R,15R,Z)-15-methoxy-5-methyl-3-oxo-2,14-dioxa-bicyclo[11.3.1]heptadec-4-en-15-yl)-3-(4-methoxybenzyl)thiazolidin-2-one was substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

$^1$H NMR (CDCl$_3$, 300 MHz): δ 1.01-1.35 (m, 5H), 1.47-1.75 (m, 8H), 1.86 (d, J=1 Hz, 3H), 1.98-2.17 (m, 3H), 2.35-2.40 (m, 1H), 3.07-3.17 (m, 1H), 3.40 (dd, J=6, 12 Hz, 1H), 3.51 (dd, J=9, 12 Hz, 1H), 3.85 (m, 1H), 4.14 (m, 1H), 4.37 (br s, 1H), 5.32 (m, 1H), 5.62 (s, 1H), 5.73 (s, 1H).

Example 53

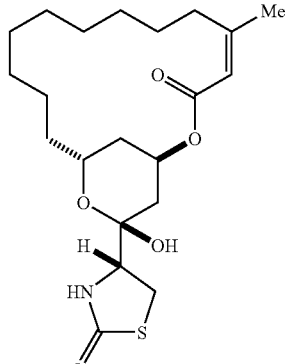

(R)-4-((1R,15R,17R,Z)-17-Hydroxy-5-methyl-3-oxo-2,16-dioxa-bicyclo[13.3.1]nonadec-4-en-17-yl)thiazolidin-2-one, Compound 11

Application of the method shown in Example 46, with the modification that (R)-4-((1R, 15R,17R,Z)-17-methoxy-5-methyl-3-oxo-2,16-dioxa-bicyclo[13.3.1]nonadec-4-en-17-yl)-3-(4-methoxybenzyl)thiazolidin-2-one is substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, affords the title compound.

Example 54

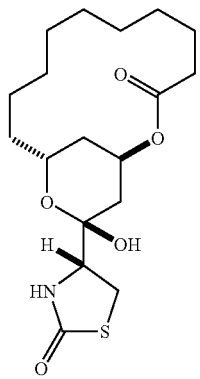

(R)-4-((1R,13R,15R)-15-Hydroxy-3-oxo-2,14-dioxa-bicyclo[11.3.1]heptadecan-15-yl)thiazolidin-2-one, Compound 10b Application of the method shown in Example 46, with the modification that (R)-4-((1R,13R,15R)-15-methoxy-3-oxo-2,14-dioxa-bicyclo[11.3.1]heptadecan-15-yl)-3-(4-methoxybenzyl)thiazolidin-2-one was substituted for (R)-4-((1R, 4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

$^1$H NMR (CDCl$_3$, 300 MHz): δ 1.23-1.48 (m, 8H), 1.48-1.72 (m, 8H), 1.79 (m, 1H), 1.93-2.09 (m, 3H), 2.32-2.42 (m, 1H), 2.49-2.58 (m, 1H), 3.40 (dd, J=6, 12 Hz, 1H), 3.52 (dd, J=9, 12 Hz, 1H), 3.86 (dd, J=6, 9 Hz, 1H), 4.19 (m, 1H), 4.32 (br s, 1H), 5.40 (m, 1H), 5.66 (s, 1H).

Example 55

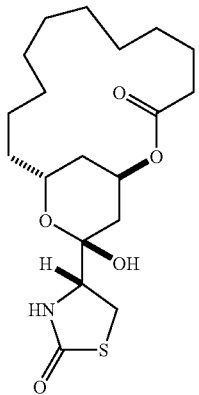

(R)-4-((1R,14R,16R)-16-Hydroxy-3-oxo-2,15-dioxa-bicyclo[12.3.1]octadecan-16-yl)thiazolidin-2-one, Compound 10d Application of the method shown in Example 46, with the modification that (R)-4-((1R,14R,16R)-16-methoxy-3-oxo-2,15-dioxa-bicyclo[12.3.1]octadecan-16-yl)-3-(4-methoxybenzyl)thiazolidin-2-one was substituted for (R)-4-((1R,4Z,8Z,13R,15R)-15-methoxy-5-methyl-3-oxo-2,14-dioxabicyclo[11.3.1]heptadeca-4,8-dien-15-yl)-3-(4-methoxybenzyl)thiazolidin-2-one, afforded the title compound.

$^1$H NMR (CDCl$_3$, 300 MHz): δ 0.85 (m, 2H), 1.23-1.42 (m, 8H), 1.46-1.71 (m, 9H), 1.96-2.07 (m, 3H), 2.40 (t, J=6 Hz, 2H), 3.40 (dd, J=6, 12 Hz, 1H), 3.52 (dd, J=9, 12 Hz, 1H), 3.85 (dd, J=6, 9 Hz, 1H), 4.11 (m, 1H), 4.34 (s, 1H), 5.40 (m, 1H), 5.68 (s, 1H).

Example 56

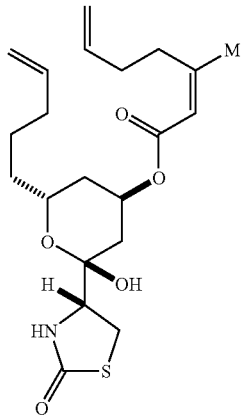

(Z)-((2R,4R,6R)-2-Hydroxy-2-((R)-2-oxothiazolidin-4-yl)-6-(pent-4-enyl)-tetrahydro-2H-pyran-4-yl)-3-Methylhepta-2,6-dienoate, Compound 1

Application of the method shown in Example 46, with the modification that (Z)-((2R,4R,6R)-2-methoxy-2-((R)-3-(4-methoxybenzyl)-2-oxothiazolidin-4-yl)-6-(pent-4-enyl)-tetrahydro-2H-pyran-4-yl)-3-methylhepta-2,6-dienoate was substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

$^1$H NMR (CDCl$_3$, 300 MHz): δ 1.41-1.55 (m, 6H), 1.85-1.96 (m, 2H), 1.94 (d, J=1 Hz, 3H), 2.07 (quar, J=7 Hz, 2H), 2.25 (quar, J=7 Hz, 2H), 2.76 (dt, J=2, 8 Hz, 2H), 3.39 (dd, J=6, 12 Hz, 1H), 3.50 (dd, J=9, 12 Hz, 1H), 3.84 (m, 1H), 4.03 (m, 1H), 4.31 (s, 1H), 4.96-5.09 (m, H), 5.42 (m, 1H), 5.60 (s, 1H), 5.69 (s, 1H), 5.75-5.89 (m, 2H).

Example 57

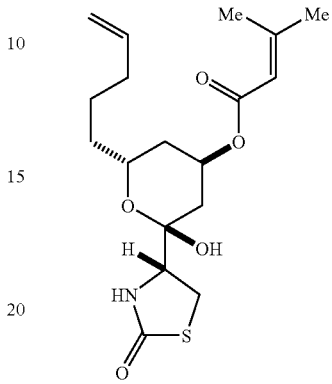

(2R,4R,6R)-2-Hydroxy-2-((R)-2-oxothiazolidin-4-yl)-6-(pent-4-enyl)-tetrahydro-2H-pyran-4-yl 3-Methylbut-2-enoate, Compound 3

Application of the method shown in Example 46, with the modification that (2R,4R,6R)-2-methoxy-2-((R)-3-(4-methoxybenzyl)-2-oxothiazolidin-4-yl)-6-(pent-4-enyl)-tetrahydro-2H-pyran-4-yl 3-methylbut-2-enoate is substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, affords the title compound.

Example 58

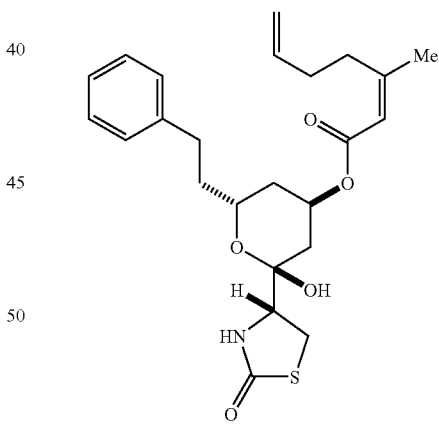

(Z)-((2R,4R,6R)-2-Hydroxy-2-((R)-2-oxothiazolidin-4-yl)-6-phenethyl-tetrahydro-2H-pyran4-yl)-3-Methylhepta-2,6-dienoate, Compound 5

Application of the method shown in Example 46, with the modification that (Z)-((2R,4R,6R)-2-methoxy-2-((R)-3-(4-methoxybenzyl)-2-oxothiazolidin-4-yl)-6-phenethyl-tetrahydro-2H-pyran-4-yl)-3-methylhepta-2,6-dienoate is substituted for (R)-4-((1R,4Z,8Z,13R,15R)-15-methoxy-5-methyl-3-oxo-2,14-dioxa-bicyclo[1.3.1]heptadeca-4,8-dien-15-yl)-3-(4-methoxybenzyl)thiazolidin-2-one, affords the title compound.

Example 59

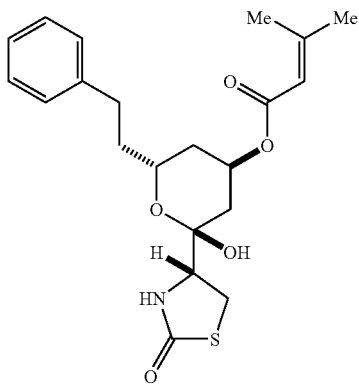

(2R,4R,6R)-2-Hydroxy-2-((R)-2-oxothiazolidin-4-yl)-6-phenethyl-tetrahydro-2H-pyran-4-yl 3-Methyl-but-2-enoate, Compound 6

Application of the method shown in Example 46, with the modification that (2R,4R,6R)-2-methoxy-2-((R)-3-(4-methoxybenzyl)-2-oxothiazolidin-4-yl)-6-phenethyl-tetrahydro-2H-pyran-4-yl 3-methylbut-2-enoate is substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, affords the title compound.

Example 60

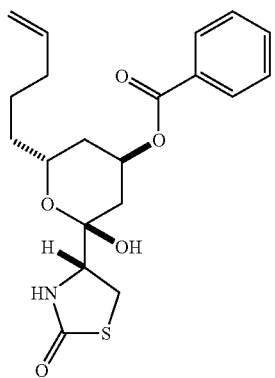

(2R,4R,6R)-2-Hydroxy-2-((R)-2oxothizolidin-4-yl)-6(pent-4-enyl)-tetrahydro-2H-pyran-4-yl Benzoate, Compound 4

Application of the method shown in Example 46, with the modification that (2R,4R,6R)-2-methoxy-2-((R)-3-(4-methoxybenzly)-2-oxothiazolidin-4yl)-6(pent-4-enyl)-tetrahydro-2H-pyran-4-yl benzoate was substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

$^1$H NMR (CDCl$_3$, 300 MHz): δ 1.40-1.63 (m, 6H), 1.99-2.09 (m, 4H), 3.41 (dd, J=6, 12 Hz, 1H), 3.51 (dd, J=9, 12 Hz, 1H), 3.84 (dd, J=6, 9 Hz, 1H), 3.90 (s, 1H), 4.17 (m, 1H), 4.94-5.04 (m, 2H), 5.63 (m, 1H), 5.68 (s, 1H), 5.79 (m, 1H), 7.48 (t, J=7 Hz, 2H), 7.61 (t, J=8 Hz, 1H), 7.99 (d, J=7 Hz, 2H).

Example 61

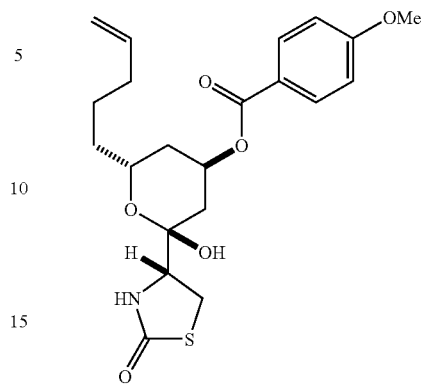

(2R,4R,6R)-2-Hydroxy-2-((R)-2-oxothiazolidin-4-yl)-6-(pent-4-enyl)-tetrahydro-2H-pyran-4-yl 4-Methoxybenzoate, Compound 4a Application of the method shown in Example 46, with the modification that (2R,4R,6R)-2-methoxy-2-((R)-3-(4-methoxybenzyl)-2-oxothiazolidin-4-yl)-6-(pent-4-enyl)-tetrahydro-2H-pyran-4-yl 4-methoxybenzoate was substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

$^1$H NMR (CDCl$_3$, 300 MHz): δ 1.39-1.63 (m, 6H), 1.96-2.13 (m, 4H), 3.41 (dd, J=6, 12 Hz, 1H), 3.50 (dd, J=9, 12 Hz, 1H), 3.83-3.87 (m, 1H), 3.88 (s, 3H), 4.01 (s, 1H), 4.16 (m, 1H), 4.94-5.04 (m, 2H), 5.61 (m, 1H), 5.66 (s, 1H), 5.78 (m, 1H), 6.95 (d, J=9 Hz, 2H), 7.94 (d, J=9 Hz, 2H).

Example 62

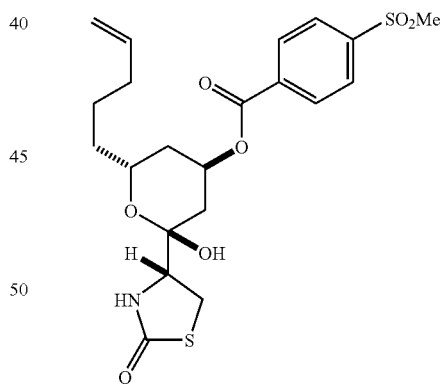

(2R,4R,6R)-2-Hydroxy-2-((R)-2-oxothiazolidin4-yl)-6-(pent-4-enyl)-tetrahydro-2H-pyran-4-yl 4-(Methylsulfonyl)benzoate, Compound 4b Application of the method shown in Example 46, with the modification that (2R,4R,6R)-2-methoxy-2-((R)-3-(4-methoxybenzyl)-2-oxothiazolidin-4-yl)-6-(pent-4-enyl)-tetrahydro-2H-pyran-4-yl 4-(methylsulfonyl)benzoate was substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

¹H NMR (CDCl₃, 300 MHz): δ 1.40-1.66 (m, 5H), 1.98-2.18 (m, 5H), 3.08 (s, 3H), 3.20 (m, 1H), 3.41 (dd, J=6, 12 Hz, 1H), 3.50 (dd, J=9, 12 Hz, 1H), 3.81 (dd, J=6, 9 Hz, 1H), 4.22 (m, 1H), 4.95-5.04 (m, 2H), 5.60 (m, 1H), 5.74-5.83 (m, 2H), 8.04 (d, J=9 Hz, 2H), 8.23 (d, J=9 Hz, 2H).

1H), 3.51 (dd, J=8, 11 Hz, 1H), 3.79-3.92 (m, 2H), 4.10 (m, 1H), 5.64 (m, 1H), 5.87 (s, 1H), 7.48 (t, J=7 Hz, 2H), 7.61 (t, J=6 Hz, 1H), 8.00 (d, J=7 Hz, 2H).

Example 63

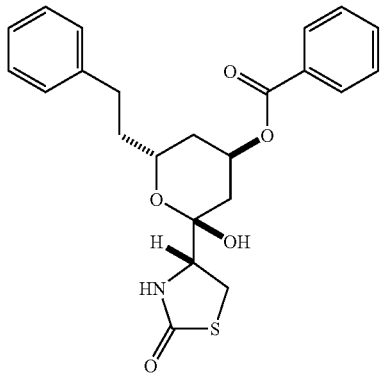

(2R,4R,6R)-2-Hydroxy-2-((R)-2-oxothiazolidin-4-yl)-6-phenethyl-tetrahydro-2H-pyran-4-yl Benzoate, Compound 7

Application of the method shown in Example 46, with the modification that (2R,4R,6R)-2-methoxy-2-((R)-3-(4-methoxybenzyl)-2-oxothiazolidin-4-yl)-6-phenethyl-tetrahydro-2H-pyran-4-yl benzoate is substituted for (R)-4-((1R,4Z,8Z,13R,15R)-15-methoxy-5-methyl-3-oxo-2,14-dioxa-bicyclo[11.3.1]heptadeca4,8-dien-15-yl)-3-(4-methoxybenzyl)thiazolidin-2-one, affords the title compound.

Example 64

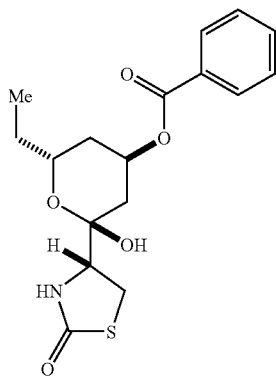

(2R,4R,6R)-6-Ethyl-2-hydroxy-2-((R)-2-oxothiazoldin-4-yl)-tetrahydro-2H-pyran-4-yl Benzoate, Compound 7a Application of the method shown in Example 46, with the modification that (2R,4R,6R)-6-ethyl-2-methoxy-2-((R)-3-(4-methoxybenzyl)-2-oxothiazolidin-4-yl)-tetrahydro-2H-pyran-4-yl benzoate was substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, afforded the title compound.

¹H NMR (CDCl₃, 300 MHz): δ 0.94 (t, J=7 Hz, 3H), 1.49-1.63 (m, 3H), 1.93-2.16 (m, 3H), 3.43 (dd, J=6, 11 Hz,

Example 65

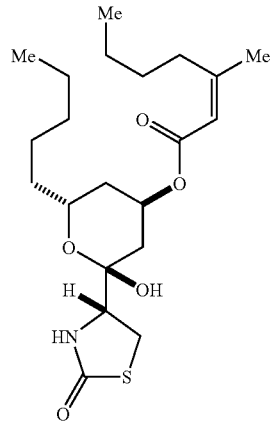

(Z)-((2R,4R,6R)-2-Hydroxy-2-((R)-2-oxothiazolidin 4yl)-6-pentyl-tetrahydro-2H-pyran-4-yl)-3-Methyl-hept-2-enoate, Compound 2

Application of the method shown in Example 46, with the modification that (Z)-((2R,4R,6R)-2-methoxy-2-((R)-3-(4-methoxybenzyl)-2-oxothiazolidin-4-yl)-6-pentyl-tetrahydro-2H-pyran-4-yl)-3-methylhept-2-enoate is substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, affords the title compound.

Example 66

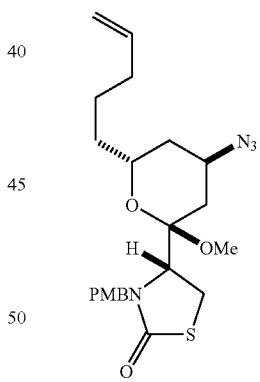

(R)-4-((2R,4R,6R)-4-Azido-2-methoxy-6-(pent-4-enyl)-tetrahydro-2 H-pyran-2-yl)-3-(4-methoxybenzyl)thiazolidin-2-one A solution of the title compound from Example 22 (1.19 mmol, used directly from the previous reaction) in DMF (12 mL) was treated with sodium azide (400 mg, 6.15 mmol), and the mixture was stirred at room temperature for 22 h. The reaction mixture was diluted with ethyl acetate, washed with satd aq NaHCO₃, ice cold 5% aq citric acid, and brine, and the organic phase was dried and concentrated. Chromatography of the residue on silica gel eluting with dichloromethane/ethyl acetate gave the title compound (432 mg, 82%) as an oil.

Example 67

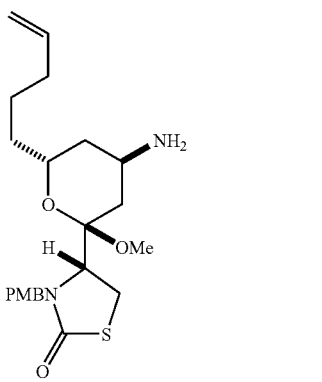

(R)-4-((2R,4R,6R)-4-Amino-2-methoxy-6-(pent 4enyl)-tetrahydro-2H-pyran-2-yl)-3-(4-methoxybenzyl)thiazolidin-2-one A suspension of the title compound from Example 66 (432 mg, 0.967 mmol) in ethanol (3 mL) and water (1 mL) was treated with NH$_4$Cl (122 mg, 2.27 mmol) and zinc dust (85.4 mg, 1.30 mmol), and the mixture was stirred vigorously at room temperature. After 6 h, an additional portion of zinc (100 mg) and NH$_4$Cl (127 mg) was added, together with additional ethanol (4.5 mL) and water (1.5 mL), and stirring was continued for 18 h. Once more portions of zinc (100 mg) and NH$_4$Cl (124 mg) were added, and stirring was continued. After 4 h, the mixture was diluted with ethyl acetate, washed with half-concentrated NH$_4$OH and brine, dried, and concentrated. The residue was treated with NH$_4$Cl (200 mg) in methanol (20 mL), and this mixture was allowed to stir at room temperature for 2 days. The mixture was diluted with ethyl acetate, washed with 1/1-satd aq NaHCO$_3$/brine and then with brine, dried, and concentrated. Chromatography of the residue on silica gel eluting with methanol/dichloromethane gave the title compound (305 mg, 75%) as an oil.

Example 68

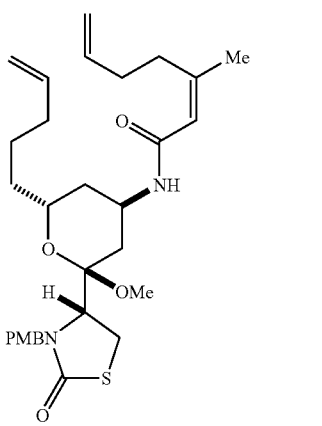

(Z)-N-((2R,4R,6R)-2-Methoxy-2-((R)-3-(4-methoxybenzyl)-2-oxothiazolidin-4-yl)-6-(pent-4-enyl)-tetrahydro-2H-pyran-4-yl)-3-methylhepta-2,6-dienamide A solution of the title compound from Example 67 (155 mg, 0.368 mmol) in dichloromethane (5 mL) was treated with the title compound from Example 21 (58 mg, 0.42 mmol), HOBT (65 mg, 0.42 mmol), and EDC (78 mg, 0.41 mmol), and the mixture was stirred at room temperature for 4 days. The mixture was then concentrated and the residue was chromatographed on silica, eluting with ethyl acetate/hexanes, which afforded the title compound (133 mg, 67%) as a crystalline solid.

Example 69

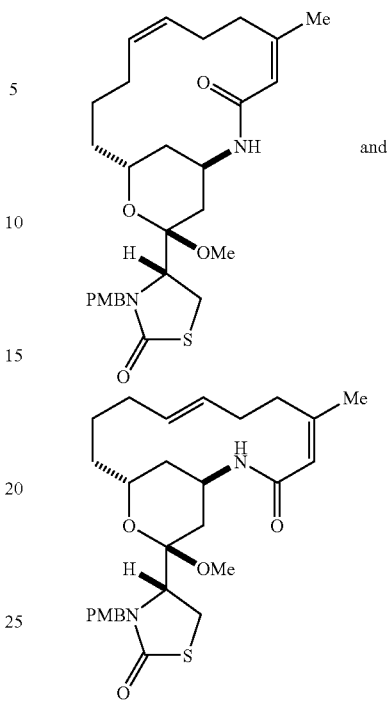

(1R,4Z,8Z,13R,15R)-15-Methoxy-15-((R)-3-(4-methoxybenzyl)-2-oxothiazolidin-4-yl)-5-methyl-14-oxa-2-aza-bicyclo[11.3.1]heptadeca-4,8-dien-3-one and (1R,4Z,8E,13R,15R)-15-Methoxy-15-((R)-3-(4-methoxybenzyl)-2-oxothiazolidin-4-yl)-5-methyl-14-oxa-2-aza-bicyclo[11.3.1]heptadeca-4,8-dien-3-one Application of the method shown in Example 36, with the modification that (Z)-N-((2R,4R,6R)-2-methoxy-2-((R)-3-(4-methoxybenzyl)-2-oxothiazolidin-4-yl)-6-(pent-4-enyl)-tetrahydro-2H-pyran-4-yl)-3-methylhepta-2,6-dienamide was substituted for (Z)-((2R,4R,6R)-2-methoxy-2-((R)-3-(4-methoxybenzyl)-2-oxothiazolidin-4-yl)-6-(pent-4-enyl)-tetrahydro-2H-pyran-4-yl)-3-methylhepta-2,6-dienoate, afforded the title compounds.

Example 70

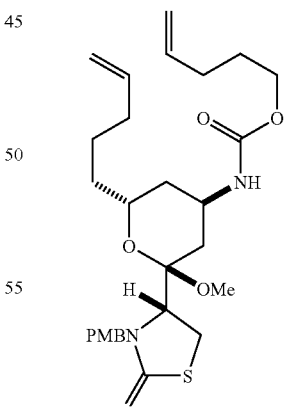

Pent-4-enyl (2R,4R,6R)-2-Methoxy-2-((R)-3-(4-methoxybenzyl)-2-oxothiazolidin4-yl)-6-(pent-4-enyl)-tetrahydro-2H-pyran-4-ylcarbamate A solution of the title compound from Example 67 (113 mg, 0.269 mmol) in dichloromethane (2 mL) was treated with a solution of 4-nitrophenyl pent-4-enyl carbonate (88 mg, 0.35 mmol) in dichloromethane (0.8 mL), diisopropylethylamine (0.061 mL, 0.35 mmol), and a catalytic amount of DMAP (0.2 mg). The mixture was stirred for 24 h, after which it was chromatographed directly on silica gel, eluting with ethyl acetate/dichloromethane, to give the title compound (119 mg, 83%) as an oil.

Example 71

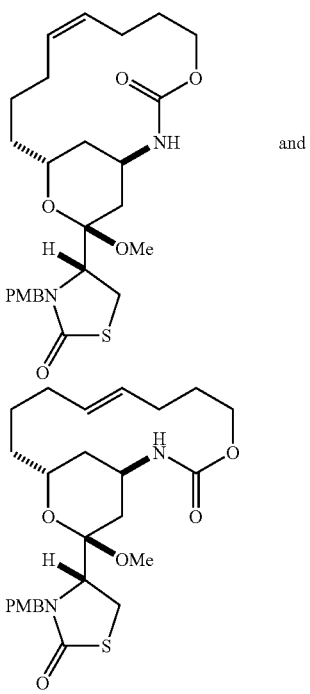

and (1R,13R,15R,Z)-15-Methoxy-15-((R)-3-(4-methoxybenzyl)-2-oxothiazolidin4-yl)-4,14-dioxa-2-aza-bicyclo[11.3.1]heptadec-8-en-3-one and (1R,13R, 15R,E)-15-Methoxy-15-((R)-3-(4-methoxybenzyl)-2-oxothiazolidin-4-yl)4,14-dioxa-2-aza-bicyclo [11.3.1]heptadec-8-en-3-one Application of the method shown in Example 36, with the modification that pent-4-enyl (2R,4R,6R)-2-methoxy-2-((R)-3-(4-methoxybenzyl)-2-oxothiazolidin-4-yl)-6-(pent-4-enyl)-tetrahydro-2H-pyran-4-ylcarbamate was substituted for (Z)-((2R,4R,6R)-2-methoxy-2-((R)-3-(4-methoxybenzyl)-2-oxothiazolidin-4-yl)-6-(pent-4-enyl)-tetrahydro-2H-pyran-4-yl) 3-methylhepta-2,6-dienoate, afforded the title compounds.

Example 72

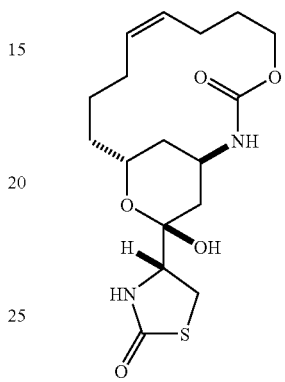

(1R,4Z,8Z,13R,15R)-15-Hydroxy-5-methyl-15-((R)-2-oxothiazolidin-4-yl)-14-oxa-2-aza-bicyclo [11.3.1]heptadeca4,8-dien-3-one, Compound 8c Application of the method shown in Example 46, with the modification that (1R,4Z,8Z,13R,15R)-15-methoxy-15-((R)-3-(4-methoxybenzyl)-2-oxothiazolidin-4-yl)-5-methyl-14-oxa-2-aza-bicyclo[11.3.1]heptadeca-4,8-dien-3-one was substituted for (R)-4-((1R,4Z,8Z,13R,15R)-15-methoxy-5-methyl-3-oxo-2,14-dioxa-bicyclo[11.3.1]heptadeca4,8-dien-15-yl)-3-(4-methoxybenzyl)thiazolidin-2-one, afforded the title compound, together with the 8E-isomer.

$^1$H NMR (CDCl$_3$, 300 MHz): δ 1.30-1.95 (m, 7H), 1.78 (s, 3H), 1.80-2.60 (m, 7H), 3.40-3.51 (m, 3H), 3.77 (m, 1H), 4.15-4.41 (m, 2H), 5.23-5.37 (m, 2H), 5.77 and 5.79 (singlets, 1H), 6.12 and 6.14 (singlets, 1H), 7.08 and 7.30 (doublets, J=8 Hz, 1H).

Example 73

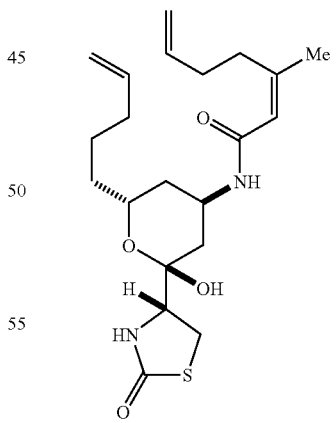

(1R,13R,15R,Z)-15-Hydroxy-15-((R)-2-oxothiazolidin-4-yl)-4,14-dioxa-2-aza-bicyclo[11.3.1]heptadec-8-en-3-one, Compound 8d Application of the method shown in Example 46, with the modification that (1R,13R,15R,Z)-15-methoxy-15-((R)-3-(4-methoxybenzyl)-2-oxothiazolidin-4-yl)-4,14-dioxa-2-aza-bicyclo[11.3.1]heptadec-8-en-3-one is substituted for (R)-4-((1R,4Z,8Z,13R,15R)-15-methoxy-5-methyl-3-oxo-2,14-dioxa-bicyclo[11.3.1]heptadeca-4,8-dien-15-yl)-3-(4-methoxybenzyl)thiazolidin-2-one, affords the title compound.

Example 74

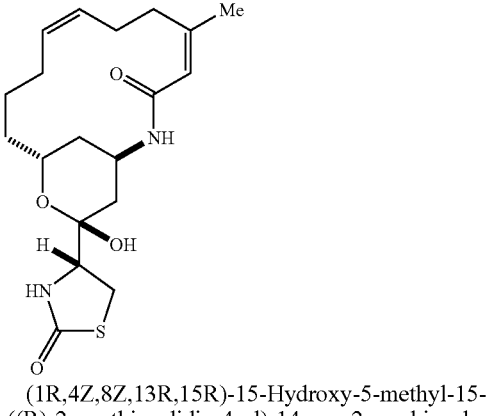

(Z)-N-((2R,4R,6R)-2-Hydroxy-2-((R)-2-oxothiazolidin-4-yl)-6-(pent-4-enyl)-tetrahydro-2H-pyran-4-yl)-3-methylhepta-2,6-dienamide, Compound 1a Application of the method shown in Example 46, with the modification that (Z)-N-((2R,4R,6R)-2-methoxy-2-((R)-3-(4-methoxybenzyl)-2-oxothiazolidin4-yl)-6-(pent-4-enyl)- tetrahydro-2H-pyran-4-yl)-3-methylhepta-2,6-dienamide was substituted for (R)-4-((1R,4Z,8Z,13R,15R)-15-methoxy-5-methyl-3-oxo-2,14-dioxa-bicyclo[11.3.1]heptadexa-4,8-dien-15-yl)-3-(4-methoxybenzyl)thiazolidin-2-one, afforded the title compound.

$^1$H NMR (CDCl$_3$, 300 MHz): δ 1.35-1.74 (m, 6H), 1.79-1.88 (m, 2H), 1.83 (s, 3H), 2.00-2.15 (m, 2H), 2.24 (quar, J=7 Hz, 2H), 2.55 (br s, 1H), 2.62-2.79 (m, 2H), 3.52 (m, 2H), 3.68-3.81 (m, 1H), 4.01 (m, 1H), 4.44 (m, 1H), 4.94-5.07 (m, 4H), 5.56 (s, 1H), 5.71-5.90 (m, 3H), 6.87 (m, 1H).

Example 75

Actin Polymerization Inhibition Assay

The quantative effects of the test compounds on the kinetics of actin polymerization were determined using a non-muscle actin polymerization kit, Actin Polymerization Biochem Kit, according to the instructions of the manufacturer (Cytoskeleton Inc; Denver, Colo.). This assay evaluates the fluorescence intensity of pyrene actin, which is greater for polymeric actin than for monomeric actin. The ability of the test compounds to inhibit actin assembly was determined by measuring their ability to inhibit this increase in the fluorescence intensity of the pyrene-labeled actin. Results were expressed as the percent inhibition measured at a standard test concentration of 10 uM.

| Compound | Percent inhibition at 10 uM |
|---|---|
| 1 | 52.3 |
| 1a | 32.4 |
| 4 | 52.0 |
| 4a | 42.2 |
| 4b | 45.6 |
| 8 | 69.9 |
| 8a | 67.2 |
| 8b | 61.7 |
| 8c | 44.9 |
| 10 | 44.1 |
| 10a | 14.0 |
| 10b | 21.8 |
| 10c | 21.7 |
| 10d | 10.4 |

Example 76

NIH/3T3 Cell Morphology Assay

NIH/3T3 cells were grown in DMEM-H containing glutamine and 10% Colorado Calf Serum. Cells were passaged regularly prior to reaching confluence. Eighteen to 24 hours prior to experimentation, the cells were plated onto Poly-L-Lysine-coated glass coverslips. On the day of experimentation, the cell culture medium was removed and was replaced with medium containing from 10 nM to 100 uM of the test compound, and the cells were incubated for 30 minutes at 37° C. The culture medium was then removed and the cells were washed with warmed PBS and fixed for 10 minutes with warmed 4% paraformaldehyde. The cells were permeabilized with 0.5% Triton-X, stained with TRITC-conjugated phalloidin and imaged using a Nikon Eclipse E600 epifluorescent microscope to determine the degree of actin disruption. Results were expressed as the concentration at which complete disruption of the actin cytoskeleton was observed.

| Compound | Concentration giving complete actin disruption, uM |
|---|---|
| 8 | 5 |
| 8a | 15 |
| 8b | 25 |

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed:

1. A compound of Formula I, or pharmaceutically-acceptable salts, tautomers, solvates, or hydrates thereof:

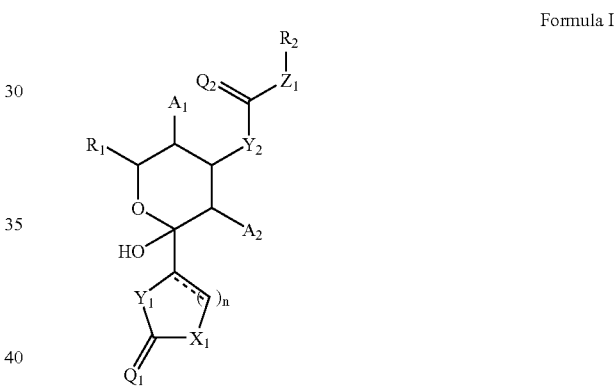

Formula I wherein:
$X_1$=S;
$Y_1$=NR$_6$;
$Y_2$=O;
$Z_1$=absent;
$Q_1$ and $Q_2$ are independently O or S;
$A_1$ and $A_2$ are independently hydrogen, halo, alkyl, or alkoxy, optionally substituted;
n=1;
$R_1$, $R_2$ and $R_6$ are independently H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted;
with a proviso that $R_1$ is not 3-monomethyl-substituted.

2. The compound according to claim 1, wherein:
$Q_1$ and $Q_2$ are O.

3. A compound of Formula I, or pharmaceutically-acceptable salts, tautomers, solvates, or hydrates thereof:

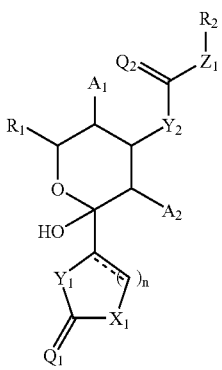

Formula I wherein:
X₁=S;
Y₁=NR₆;
Y₂=O;
Z₁=absent;
Q₁ and Q₂ are independently O or S;
A₁ and A₂ are independently hydrogen, halo, alkyl, or alkoxy, optionally substituted;
n=1;
R₂ and R₆ are independently H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted;
R₁ is:

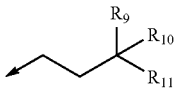

where the bond marked with an arrow denotes the point of attachment of the group R₁ to the rest of the molecule,
wherein R₉-R₁₀ are independently H, halo, alkyl, or alkenyl, optionally substituted, and R₁₁ is H, halo, alkyl, alkenyl, or —W—R₁₂, optionally substituted, where W=O, S, SO, SO₂, NH, or N-alkyl, and
R₁₂ is H, alkyl, or alkenyl,
provided that if R₉ is H and R₁₀ is methyl, then R₁₁ is H, halo, or —W—R₁₂.

4. The compound according to claim 1, wherein A₁ and A₂ are both hydrogen, and the ring containing X₁ is fully saturated.

5. The compound according to claim 1, wherein said compound is selected from the group consisting of (Z)-((2R,4R,6R)-2-hydroxy-2-((R)-2-oxothiazolidin-4-yl)-6-(pent-4-enyl)-tetrahydro-2H-pyran-4-yl) 3-methylhepta-2,6-dienoate, (Z)-((2R,4R,6R)-2-hydroxy-2-((R)-2-oxothiazolidin-4-yl)-6-pentyl-tetrahydro-2H-pyran-4-yl) 3-methylhept-2-enoate, (2R,4R,6R)-2-hydroxy-2-((R)-2-oxothiazolidin-4-yl)-6-(pent-4-enyl)-tetrahydro-2H-pyran-4-yl 3-methylbut-2-enoate, (2R,4R,6R)-2-hydroxy-2-((R)-2-oxothiazolidin-4-yl)-6-(pent-4-enyl)-tetrahydro-2H-pyran-4-yl benzoate, (2R,4R,6R)-2-hydroxy-2-((R)-2-oxothiazolidin-4-yl)-6-(pent-4-enyl)-tetrahydro-2H-pyran-4-yl 4-methoxybenzoate, (2R,4R,6R)-2-hydroxy-2-((R)-2-oxothiazolidin-4-yl)-6-(pent-4-enyl)-tetrahydro-2H-pyran-4-yl 4-(methylsulfonyl)benzoate, (Z)-((2R,4R,6R)-2-hydroxy-2-((R)-2-oxothiazolidin-4-yl)-6-phenethyl-tetrahydro-2H-pyran-4-yl) 3-methylhepta-2,6-dienoate, (2R,4R,6R)-2-hydroxy-2-((R)-2-oxothiazolidin-4-yl)-6-phenethyl-tetrahydro-2H-pyran-4-yl 3-methylbut-2-enoate, (2R,4R,6R)-2-hydroxy-2-((R)-2-oxothiazolidin-4-yl)-6-phenethyl-tetrahydro-2H-pyran-4-yl benzoate, and (2R,4R,6R)-6-ethyl-2-hydroxy-2-((R)-2-oxothiazolidin-4-yl)-tetrahydro-2H-pyran-4-yl benzoate.

6. A compound of Formula II, or pharmaceutically-acceptable salts, tautomers, solvates, or hydrates thereof:

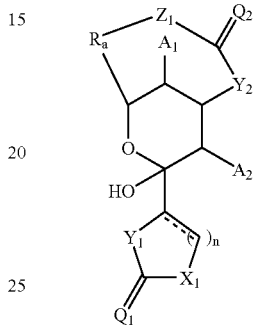

Formula II wherein:
R_a is an alkylene chain, from 4 to 15 atoms in length, the alkylene chain optionally contains from 1 to 4 unsaturations and is optionally substituted;
X₁=S;
Y₁=NR₆;
Y₂=O;
Z₁=absent;
Q₁ and Q₂ are independently O or S;
A₁ and A₂ are independently hydrogen, halo, alkyl, or alkoxy, optionally substituted;
n=1;
R₆ is H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted;
with a proviso that when Q₁ and Q₂ are O, then R_a is not 3-monomethyl-susbtituted, as counted from the point of attachment distal to Z₁.

7. The compound according to claim 6, wherein said R_a is an alkylene chain, from 6 to 13 atoms in length, wherein the alkylene chain optionally contains from 1 to 3 unsaturations, and is optionally substituted.

8. The compound according to claim 7, wherein said R_a is an alkylene chain, from 8 to 11 atoms in length, wherein the alkylene chain optionally contains from 1 to 3 unsaturations, and is optionally substituted.

9. The compound according to claim 6, wherein
R_a is an alkylene chain, from 6 to 13 atoms in length, wherein the alkylene chain optionally contains from 1 to 3 unsaturations, and is optionally substituted; and
Q₁ and Q₂ are O.

10. The compound according to claim 9, wherein
R_a is an alkylene chain, from 8 to 11 atoms in length, wherein the alkylene chain optionally contains from 1 to 3 unsaturations, and is optionally substitute; and
Y₁=NH.

11. The compound according to claim 6, wherein $A_1$ and $A_2$ are both hydrogen, and the ring containing $X_1$ is fully saturated.

12. A compound of Formula II, or pharmaceutically-acceptable salts, tautomers, solvates, or hydrates thereof:

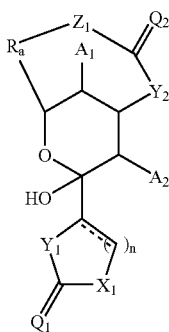

Formula II wherein:
$X_1$=S;
$Y_1$=$NR_6$;
$Y_2$=O;
$Z_1$=absent;
$Q_1$ and $Q_2$ are independently O or S;
$A_1$ and $A_2$ are independently hydrogen, halo, alkyl, or alkoxy, optionally substituted;
n=1;
$R_6$ is H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted;
$R_a$ is:

$(CH_2)_{m1}$—$(CR_9R_{10})$—$(CH_2)_{m2}$—$V_1$—$(CH_2)_{m3}$—$V_2$ wherein:
$m_1$, $m_2$, and $m_3$ are independently 0-5 inclusively, and $m_1+m_2+m_3$ is between 2 and 14 inclusively;
$R_9$ and $R_{10}$ are independently H, halo, alkyl, alkenyl, alkynyl, cycloalkyl, cycloalkenyl, cycloalkylalkyl, aryl, arylalkyl, arylalkenyl, heteroaryl, heteroarylalkyl, heteroarylalkenyl, heterocycle, or —W—$R_{12}$, optionally substituted;
W=O, S, SO, $SO_2$, NH, N-alkyl, N-cycloalkyl, N-aryl, or N-heteroaryl;
$R_{12}$ is H, alkyl, alkenyl, cycloalkyl, aryl, or heteroaryl;
$V_1$ is $NR_{13}$, O, S, SO, SO2, cis —$C(R_{13})$=$C(R_{14})$—, trans —$C(R_{13})$=$C(R_{14})$—, —OC(=O)—, —C(=O)O—, —$N(R_{13})C$(=O)—, —C(=O)$N(R_{13})$, —$N(R_{13})C$(=O)O—, —OC(=O)N($R_{13}$)—, —$N(R_{13})$SO2—, —SO2N($R_{13}$)—, —$N(R_{13})C$(=O)N($R_{14}$)—, cycloalkyl, cycloalkenyl, aryl, heteroaryl, heterocycle, or absent;
$V_2$ is $NR_{13}$, O, cis —$C(R_{13})$=$C(R_{14})$—, trans —$C(R_{13})$=$C(R_{14})$—, —C—(triple bond)—C—, cycloalkyl, cycloalkenyl, aryl, heteroaryl, heterocycle, or absent;
$R_{13}$ and $R_{14}$ are independently H, alkyl, alkenyl, alkynyl, cycloalkyl, cycloalkenyl, cycloalkylalkyl, aryl, arylalkyl, arylalkenyl, heteroaryl, heteroarylalkyl, heteroarylalkenyl, or heterocycle, optionally substituted;
with a proviso that when $m_1$ is 2, $m_2$ is 0, $m_3$ is 2, $V_1$ is cis —CH=CH—, $V_2$ is —C(Me)=CH—, $R_9$ is H, and $R_{10}$ is alkyl,
then $R_{10}$ is a $C_2$-$C_{10}$ alkyl.

13. The compound according to claim 12, wherein
$R_9$ and $R_{10}$ are H, halo, alkyl, alkenyl, cycloalkyl, cycloalkenyl, cycloalkylalkyl, aryl, or arylalkyl, optionally substituted;
$V_1$ is O, S, cis —$C(R_{13})$=$C(R_{14})$—, trans —$C(R_{13})$=$C(R_{14})$—, cycloalkyl, aryl, or absent; and
$V_2$ is cis —$C(R_{13})$=$C(R_{14})$—, trans —$C(R_{13})$=$C(R_{14})$—, cycloalkenyl, or aryl.

14. A compound of Formula II, or pharmaceutically-acceptable salts, tautomers, solvates, or hydrates thereof:

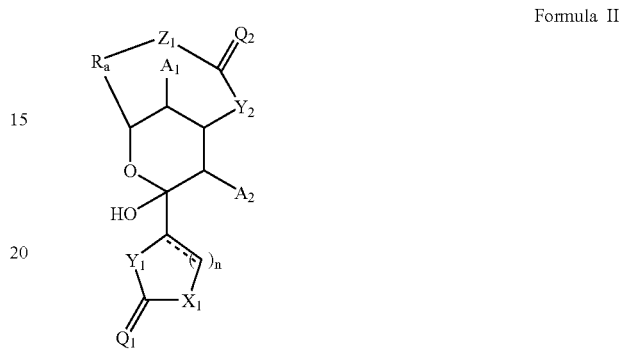

Formula II wherein
$R_a$ is an alkylene chain, from 4 to 15 atoms in length, wherein the alkylene chain optionally contains from 1 to 4 unsaturations, 1 to 2 cycloalkyl, 1 to 2 aryl, or 1 to 2 heteroaryl, and is optionally substituted;
$X_1$=S;
$Y_1$=$NR_6$;
$Y_2$=O;
$Z_1$=absent;
$Q_1$ and $Q_2$ are independently O or S;
$A_1$ and $A_2$ are independently hydrogen, halo, alkyl, or alkoxy, optionally substituted;
n=1;
$R_6$ is H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted;
with a proviso that when $Q_1$ and $Q_2$ are O,
and in the case that $R_a$ is 9 or 11 carbons in length, begins with $CH_2CH_2$ from the point of attachment to the pyran ring, and does not contain aryl or heteroaryl, then $R_a$ is:

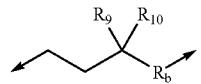

wherein $R_b$ is an alkylene chain, $C_6$-$C_8$ in length, optionally containing from 1 to 4 unsaturations, optionally containing a cycloalkyl ring, and optionally substituted,
$R_9$ and $R_{10}$ are independently H, halo, alkyl, alkenyl, alkynyl, cycloalkyl, cycloalkenyl, cycloalkylalkyl, aryl, arylalkyl, arylalkenyl, heteroaryl, heteroarylalkyl, heteroarylalkenyl, heterocycle, or —W—$R_{12}$, optionally substituted, where W=O, S, SO, $SO_2$, NH, N-alkyl, N-cycloalkyl, N-aryl, or N-heteroaryl, and $R_{12}$ is H, alkyl, alkenyl, cycloalkyl, aryl, or heteroaryl,
such that if $R_9$ is H, and $R_{10}$ is alkyl, then $R_{10}$ is $C_2$-$C_{10}$ alkyl.

15. The compound according to claim 6, wherein said compound is selected from the group consisting of (R)-4-((1R,4Z,8Z,13R,15R)-15-hydroxy-5-methyl-3-oxo-2,14-di-oxa-bicyclo[11.3.1]heptadeca-4,8-dien-15-yl)thiazolidin-2-one, (R)-4-((1R,4Z,8E,13R,15R)-15-hydroxy-5-methyl-3-oxo-2,14-dioxa-bicyclo[11.3.1]heptadeca-4,8-dien-15-yl)

thiazolidin-2-one, (R)-4-((1R,4Z,8E,10Z,15R,17R)-17-hydroxy-5-methyl-3-oxo-2,16-dioxa-bicyclo[13.3.1]nonadeca-4,8,10-trien-17-yl)thiazolidin-2-one, (R)-4-((1R,13R,15R,Z)-15-hydroxy-5-methyl-3-oxo-2,14-dioxa-bicyclo[11.3.1]heptadec-4-en-15-yl)thiazolidin-2-one, (R)-4-((1R,13R,15R,Z)-15-hydroxy-3-oxo-2,14-dioxa-bicyclo[11.3.1]heptadec-8-en-15-yl)thiazolidin-2-one, (R)-4-((1R,13R,15R)-15-hydroxy-3-oxo-2,14-dioxa-bicyclo[11.3.1]heptadecan-15-yl)thiazolidin-2-one, (R)-4-((1R,14R,16R,E)-16-hydroxy-3-oxo-2,15-dioxa-bicyclo[12.3.1]octadec-9-en-16-yl)thiazolidin-2-one, (R)-4-((1R,14R,16R)-16-hydroxy-3-oxo-2,15-dioxa-bicyclo[12.3.1]octadecan-16-yl)thiazolidin-2-one, (R)-4-((1R,15R,17R,Z)-17-hydroxy-5-methyl-3-oxo-2,16-dioxa-bicyclo[13.3.1]nonadec-4-en-17-yl)thiazolidin-2-one, (S)-4-((1R,4Z,8Z,13R,15R)-15-hydroxy-5-methyl-3-oxo-2,14-dioxa-bicyclo[11.3.1]heptadeca-4,8-dien-15-yl)oxazolidin-2-one, (R)-4-((1R,4Z,8Z,10S,13R,15R)-10-ethyl-15-hydroxy-5-methyl-3-oxo-2,14-dioxa-bicyclo[11.3.1]heptadeca-4,8-dien-15-yl)thiazolidin-2-one, and (R)-4-((1R,4Z,8Z,13R,15R)-15-hydroxy-5,10,10-trimethyl-3-oxo-2,14-dioxa-bicyclo[11.3.1]heptadeca-4,8-dien-15-yl)thiazolidin-2-one.

16. The compound according to claim 15, wherein said compound is (R)-4-((1R,4Z,8Z,13R,15R)-15-hydroxy-5-methyl-3-oxo-2,14-dioxa-bicyclo[11.3.1]heptadeca-4,8-dien-15-yl)thiazolidin-2-one, or (R)-4-((1R,4Z,8E,13R,15R)-15-hydroxy-5-methly-3-oxo-2,14-dioxa-bicyclo[11.3.1]heptadeca-4,8-dien-15-yl)thiazolidin-2-one.

17. A pharmaceutical composition comprising a pharmaceutically acceptable carrier and at least one compound according to claim 1.

18. A pharmaceutical composition comprising a pharmaceutically acceptable carrier and at least one compound according to claim 6.

19. A method for reducing intraocular pressure, comprising the step of administering to a subject in need thereof the compound according to claim 1, in an amount effective to alter actin cytoskeleton.

20. The method according to claim 19, wherein said compound is locally administered to the eye in the form of an ophthalmic formulation.

21. A method for reducing intraocular pressure, comprising the step of administering to a subject in need thereof the compound according to claim 6, in an amount effective to alter actin cytoskeleton.

22. The method according to claim 21, wherein said compound is locally administered to the eye in the form of an ophthalmic formulation.

23. The compound according to claim 12, wherein said compound is selected from the group consisting of (R)-4-((1R,4Z,8E,10S,13R,15R)-15-hydroxy-5,10-dimethyl-3-oxo-2,14-dioxa-bicyclo[11.3.1]heptadeca-4,8-dien-15-yl)thiazolidin-2-one, (R)-4-((1R,4Z,8Z,10S,13R,15R)-5-ethyl-15-hydroxy-10-methyl-3-oxo-2,14-dioxa-bicyclo[11.3.1]heptadeca-4,8-dien-15-yl)thiazolidin-2-one, (R)-4-((1R,4Z,8Z,10S,13R,15R)-15-hydroxy-4,5,10-trimethyl-3-oxo-2,14-dioxa-bicyclo[11.3.1]heptadeca-4,8-dien-15-yl)thiazolidin-2-one, (R)-4-((1R,11Z,13S,16R,18R)-18-hydroxy-13-methyl-3-oxo-2,17-dioxatricyclo[14.3.1.0$^{4,8}$]icosa-4(8),11-dien-18-yl)thiazolidin-2-one, (R)-4-((1R,12Z,14S,17R,19R)-19-hydroxy-14-methyl-3-oxo-2,18-dioxatricyclo[15.3.1.0$^{4,9}$]henicosa-4,6,8,12-tetraen-19-yl)thiazolidin-2-one, (R)-4-((1R,10Z,15R,17R)-17-hydroxy-3-oxo-2,16-dioxatricyclo[13.3.1.1$^{4,8}$]icosa-4(20),5,7,10-tetraen-17-yl)thiazolidin-2-one, (R)-4-((1R,4S,13Z,17R,19R)-19-hydroxy-4,13-dimethyl-15-oxo-16,20-dioxatricyclo[15.3.1.0$^{5,10}$]henicosa-5,7,9,13-tetraen-19-yl)thiazolidin-2-one, (R)-4-((1R,4S,12Z,16R,18R)-18-hydroxy-4,12-dimethyl-14-oxo-15,19-dioxa-6-thiatricyclo[14.3.1.0$^{5,9}$]icosa-5(9),7,12-trien-18-yl)thiazolidin-2-one, (R)-4-((1R,15E,19,R 21R)-21-hydroxy-15-methyl-17-oxo-18,22-dioxa-8-azatricyclo[17.3.1.0$^{5,10}$]tricosa-5,7,9,15-tetraen-21-yl)thiazolidin-2-one, (1R,13R,15R)-8-acetyl-15-hydroxy-15-((R)-2-oxothiazolidin-4-yl)-2,14-dioxa-8-azabicyclo[11.3.1]heptadecan-3-one, (R)-4-((1R,10S,13R,15R)-15-hydroxy-10-methyl-3-oxo-2,8,14-trioxa-bicyclo[11.3.1]heptadecan-15-yl)thiazolidin-2-one, and (R)-4-((1R,13R,15R)-15-hydroxy-3-oxo-2,14-dioxa-9-thia-bicyclo[11.3.1]heptadecan-15-yl)thiazolidin-2-one.

24. A compound according to Formula I,

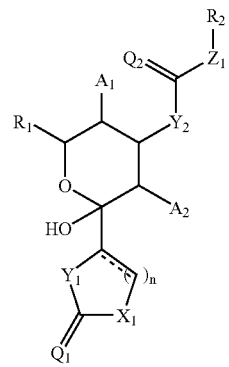

Formula I wherein:
$X_1$=S;
$Y_1$=NR$_6$;
$Y_2$=O;
$Z_1$=absent;
$Q_1$ and $Q_2$ are independently O or S;
$A_1$ and $A_2$ are independently hydrogen, halo, alkyl, or alkoxy, optionally substituted;
n=1;
$R_2$ and $R_6$ are independently H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted; and
$R_1$ is independently H, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted.

25. A compound of Formula II, or pharmaceutically-acceptable salts, tautomers, solvates, or hydrates thereof:

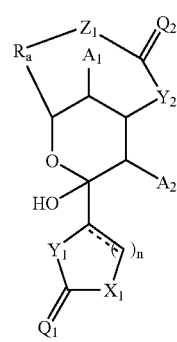

Formula II wherein:
$R_a$ is an alkylene chain, from 4 to 15 atoms in length, wherein the carbon atoms of the alkylene chain are replaced by from 1 to 3 O, S, or N atoms, the alkylene chain optionally contains 1 to 2 cycloalkyl, 1 to 2 aryl, or 1 to 2 heteroaryl, and is optionally substituted;
$X_1$=S;
$Y_1$=NR$_6$;
$Y_2$=O;
$Z_1$=absent;

$Q_1$ and $Q_2$ are independently O or S;

$A_1$ and $A_2$ are independently hydrogen, halo, alkyl, or alkoxy, optionally substituted;

n=1; and $R_6$ is H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted.

26. A compound of Formula II, or pharmaceutically-acceptable salts, tautomers, solvates, or hydrates thereof:

Formula II

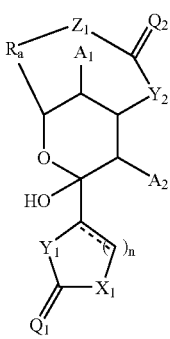

wherein:

$R_a$ is an alkylene chain, from 4 to 15 atoms in length, the alkylene chain contains 1 to 2 cycloalkyl, 1 to 2 aryl, or 1 to 2 heteroaryl, optionally contains from 1 to 4 unsaturations, and is optionally substituted;

$X_1$=S;

$Y_1$=$NR_6$;

$Y_2$=O;

$Z_1$=absent;

$Q_1$ and $Q_2$ are independently O or S;

$A_1$ and $A_2$ are independently hydrogen, halo, alkyl, or alkoxy, optionally substituted;

n=1; and $R_6$ is H, alkyl, alkenyl, alkynyl, cycloalkyl, cycloalkenyl, cycloalkylalkyl, aryl, arylalkyl, arylalkenyl, arylalkynyl, heteroaryl, heteroarylalkyl, heteroarylalkenyl, heteroarylalkynyl, or heterocycle, optionally substituted.

* * * * *